United States Patent [19]
Lasters et al.

[11] Patent Number: 5,807,980
[45] Date of Patent: Sep. 15, 1998

[54] BOVINE PANCREATIC TRYPSIN INHIBITOR DERIVED INHIBITORS OF FACTOR VIIA-TISSUE FACTOR COMPLEX

[75] Inventors: Ignace Lasters, Antwerp; Marc De Maeyer, Groot-Bijgaarden, both of Belgium; William Charles Ripka, San Diego, Calif.

[73] Assignee: Corvas International, Inc., San Diego, Calif.

[21] Appl. No.: 86,328

[22] Filed: Jul. 1, 1993

Related U.S. Application Data

[63] Continuation-in-part of Ser. No. 952,801, Sep. 25, 1992, abandoned, which is a continuation-in-part of Ser. No. 913,232, Jul. 13, 1992, abandoned.

[51] Int. Cl.$^6$ .......................... C07K 14/81; A61K 38/55
[52] U.S. Cl. ............................. 530/324; 530/350; 514/12
[58] Field of Search ................................. 435/69.1, 69.2; 530/350, 324; 514/12

[56] References Cited

U.S. PATENT DOCUMENTS

| | | | |
|---|---|---|---|
| 4,966,852 | 10/1990 | Wun et al. | 435/320.1 |
| 4,994,372 | 2/1991 | Tabor et al. | 435/6 |
| 5,032,573 | 7/1991 | Auerswald et al. | 514/12 |
| 5,096,815 | 3/1992 | Ladner et al. | 435/69.1 |
| 5,106,833 | 4/1992 | Broze, Jr. et al. | 514/12 |
| 5,118,668 | 6/1992 | Auerswald et al. | 514/12 |

FOREIGN PATENT DOCUMENTS

| | | |
|---|---|---|
| 339942A | 11/1989 | European Pat. Off. . |
| 439442A | 7/1991 | European Pat. Off. . |
| 2208511 | 4/1989 | United Kingdom . |
| 9002809 | 3/1990 | WIPO . |

OTHER PUBLICATIONS

Hynes, T.R. et al. (Oct. 1990) "X–ray crystal structure of the protease inhibitor domain of Alzhemier's amyloid beta–protein precursor" Biochem. 29(43):10009–10140.
Hoad and Geczy, 136 *J. Immun. Methods* 269, 1991.
Roberts et al., 89 *Proc. Natl. Acad. Sci. USA* 2429, 1992.
Goldenberg and Creighton, 179 *J. Mol. Biol.* 527, 1984.
Stanssens et al., *Nucleic Acids Research* 17:4441–4454 (1989).
Girard et al., *Nature*, 338:518–520 (1989).
Fritz et al., *Arzneim.–Forsch/Drug Res.*, 33:479–494 (1983).
Bode et al., *Eur. J. Biochem.*, 144:185–190 (1984).
Vedvick et al., *J. Indus. Microbiol.*, vol. 7 (1991), pp. 197–201.
Creighton et al., *Trends in Biochemical Sciences*, vol. 14 (Aug. 1989), pp. 319–324.
Schulz et al., "Principles of Protein Structure", published 1979 by Springer–Verlag (N.Y.), pp. 14–16.
Schecter et al., *Biochem. Biophys. Res. Commun.*, 27:157 (1967).
Laskowski et al., *J. Ann. Rev. Biochem.*, 49:593:626 (1980).
Callander et al., *J. Biol. Chem.*, 267:876–882 (1992).
Parmley et al., *Gene*, 73:305–318 (1988).
Mackie et al., *Blood Reviews*, 3:237–250 (1989).
*Remington's Pharmaceutical Sciences*, Mack Publishing Co. (A.R. Gennaro edit. 1985).
Yanish–Perron et al., *Gene*, 33:103–199 (1985).
Bullock et al., *Biotechniques*, 5:376–379 (1987).
Marks et al., *J. Biol. Chem.*, 261:7115–7118 (1986).
Goldenberg, *Biochemistry*, 27:2481–2489 (1988).
Vieira et al., *Meth. in Enzymol.*, 153:3–11 (1987).
Sambrook et al., Molecular Cloning–A Laboratory Manual, Cold Spring Harbor Laboratory Press, p. 4.29 (1989).
Weislander, *Anal. Biochem.*, 98:305–309 (1979).
Wu et al., Oligonucleotide Synthesis–a Practical Approach, IRL Press Oxford and Washington, D.C., pp. 135–151 (Ed. Gait, M.J. 1984).
Zell et al., *The EMBO Journal*, 6:1809–1815 (1987).
Zacher III et al., *Gene*, 9:127–140 (1980).
Kunkel, *Proc. Natl. Acad. Sci. USA*, 82:488–492 (1985).
Cwirla et al., *Proc. Natl. Acad. Sci. USA*, 87:6378–6382 (1990).
Harlow et al., Antibodies: A Laboratory Manual, Cold Spring Harbor Laboratory (1988).
Clements et al., *Gene*, 106:267–272 (1991).
Béguin et al., *Thromb. Haemost.*, 68:136–142 (1992).

*Primary Examiner*—Robert A. Wax
*Assistant Examiner*—Kawai Lau
*Attorney, Agent, or Firm*—Lyon & Lyon LLP

[57] ABSTRACT

Compounds derived from BPTI which inhibit factor VIIa-TF complex with an inhibition constant of less than 500 nM, their pharmaceutical compositions, and methods of use. Also disclosed are isolated nucleic acid segments encoding for the compounds, vectors comprising the nucleic acid segment and promoter, transformed host cells, and a method for preparing the compounds using transformed host cells.

4 Claims, 8 Drawing Sheets

Pst205 (74-mer)
    GCTCCGGACT TCTGTCTCGA GCCACCGTAT ACCGGCCCCT GCAAGGCTCG
TATTATCCGC TACTTCTACA ACGC Pst206 (78-mer)
    CTTGGCGTTG TAGAAGTAGC GGATAATACG AGCCTTGCAG GGGCCGGTAT
ACGGTGGCTC GAGACAGAAG TCCGGAGC Pst207 (102-mer)
    CAAGGCCGGA CTCTGTCAGA CCTTTGTATA TGGTGGCTGC CGTGCAAAGC
GTAACAATTT CAAGTCGGCC GAGGACTGCA TGCGTACCTG TGGTGGCGCC TA Pst208 (102-mer)
    AGCTTAGGCG CCACCACAGG TACGCATGCA GTCCTCGGCC GACTTGAAAT
TGTTACGCTT TGCACGGCAG CCACCATATA CAAAGGTCTG ACAGAGTCCG GC

```
GAATTCGAGC TCGAGCTTAC TCCCCATCCC CCTGTTGACA ATTAATC
EcoRI                                    -35
ATC GGCTCGTATA ATGTGTGGA ATTGTGAGCG GATAACAATT TCACA
        -10
CAGGA AACAGGATCC GCGGATCCGT GGAGAAAATA AA
              SacII              SD
```

```
ATG-AAA-CAA-AGC-ACT-ATT-GCA-CTG-GCA-CTC-TTA-CCG
Met  Lys Gln Ser Thr Ile Ala Leu Ala Leu Leu Pro
-21  -20 -19 -18 -17 -16 -15 -14 -13 -12 -11 -10
```

```
                                        KpnI
TTA-CTG-TTT-ACC-CCT-GTG-ACA-AAA-GCG GTACC
Leu Leu Phe Thr Pro Val Thr Lys Ala
-9  -8  -7  -6  -5  -4  -3  -2  -1
                              HindIII    XbaI
CGGGGATCCT CTAGAGTCGA CCTGCAGGCA TGCAAGCTTG GTCTAGA
```

FIG. 4B

```
    BspMII                            AccI
GCT CCG GAC TTC TGT CTC GAG CCA CCG TAT ACC GGC
CGA GGC CTG AAG ACA GAG CTC GGT GGC ATA TGG CCG
Ala Pro Asp Phe Cys Leu Glu Pro Pro Tyr Thr Gly
 1   2   3   4   5   6   7   8   9  10  11  12

CCC TGC AAG GCT CGT ATT ATC CGC TAC TTC TAC AAC
GGG ACG TTC CGA GCA TAA TAG GCG ATG AAG ATG TTG
Pro Cys Lys Ala Arg Ile Ile Arg Tyr Phe Tyr Asn
13  14  15  16  17  18  19  20  21  22  23  24

StyI
GCC AAG GCC GGA CTC TGT CAG ACC TTT GTA TAT GGT
CGG TTC CGG CCT GAG ACA GTC TGG AAA CAT ATA CCA
Ala Lys Ala Gly Leu Cys Gln Thr Phe Val Tyr Gly
25  26  27  28  29  30  31  32  33  34  35  36

GGC TGC CGT GCA AAG CGT AAC AAT TTC AAG TCG GCC
CCG ACG GCA CGT TTC GCA TTG TTA AAG TTC AGC CGG
Gly Cys Arg Ala Lys Arg Asn Asn Phe Lys Ser Ala
37  38  39  40  41  42  43  44  45  46  47  48

SphI              KasI
GAG GAC TGC ATG CGT ACC TGT GGT GGC GCC TA
CTC CTG ACG TAC GCA TGG ACA CCA CCG CGG ATT CGA
Glu Asp Cys Met Arg Thr Cys Gly Gly Ala
49  50  51  52  53  54  55  56  57  58
```

BOVINE PANCREATIC TRYPSIN INHIBITOR DERIVED INHIBITORS OF FACTOR VIIA-TISSUE FACTOR COMPLEX

RELATED APPLICATIONS

This application is a continuation-in-part of Ripka et al., "Bovine Pancreatic Trypsin Inhibitor Derived Inhibitors of Factor VIIa-Tissue Factor Complex", U.S. Ser. No. 07/952,801 filed Sep. 25, 1992, now abandonded, which is a continuation-in-part of "Bovine Pancreatic Trypsin Inhibitor Derived Inhibitors of Factor Xa", U.S. Ser. No. 07/913,232 filed Jul. 13, 1992, now abandonded, both of which are hereby incorporated by reference herein.

FIELD OF INVENTION

The present invention relates to Bovine Pancreatic Trypsin Inhibitor-derived inhibitors, and methods for their preparation and therapeutic use.

BACKGROUND OF THE INVENTION

Bovine pancreatic trypsin inhibitor (also referred to as BPTI or Aprotinin) is a polypeptide having 58 amino acid residues, with internal cross linking by three disulfide bridges. Frits, H. and Wunderer, G., Arzneim.-Forsch/Drug Res., 33: 479–494 (1983). The amino acid sequence of mature wild type BPTI is shown in (I).

| 1 | 2 | 3 | 4 | 5 | 6 | 7 | 8 | 9 | 10 | 11 | 12 | (I) |
|---|---|---|---|---|---|---|---|---|----|----|----|----|
| Arg | Pro | Asp | Phe | Cys | Leu | Glu | Pro | Pro | Tyr | Thr | Gly | |
| 13 | 14 | 15 | 16 | 17 | 18 | 19 | 20 | 21 | 22 | 23 | 24 | |
| Pro | Cys | Lys | Ala | Arg | Ile | Ile | Arg | Tyr | Phe | Tyr | Asn | |
| 25 | 26 | 27 | 28 | 29 | 30 | 31 | 32 | 33 | 34 | 35 | 36 | |
| Ala | Lys | Ala | Gly | Leu | Cys | Gln | Thr | Phe | Val | Tyr | Gly | |
| 37 | 38 | 39 | 40 | 41 | 42 | 43 | 44 | 45 | 46 | 47 | 48 | |
| Gly | Cys | Arg | Ala | Lys | Arg | Asn | Asn | Phe | Lys | Ser | Ala | |
| 49 | 50 | 51 | 52 | 53 | 54 | 55 | 56 | 57 | 58 | | | |
| Glu | Asp | Cys | Met | Arg | Thr | Cys | Gly | Gly | Ala | | | |

(SEQ ID NO:1)

In the mature folded protein, disulfide bonds are formed between the following pairs of cysteines: 5–55, 14–38 and 30–51.

The crystal structures of BPTI or BPTI variants complexed with trypsin, kallikrein, trypsinogen, and anhydrotrypsin show that two loops of the inhibitor form the interface with the serine proteases at residues 11–19 and 34–39. Bode, W., et al., Eur. J. Biochem., 144: 185–190 (1984). These residues are believed to be largely responsible for defining the specificity of the inhibitor for the target protease, (i.e., the lower the Ki the higher the specificity, e.g., a Ki of up to 500 nM is regarded as specific in this application.). In combination with the sequences of serine protease, the specificity and selectivity of the protease inhibitors has been suggested to originate from sequence variations on both sides of the protease-inhibitor interface. Creighton, T. E. and Darby, N. J., TIBS, 14: 319–325 (1989). Selectivity relates to the difference in inhibitor constant of a specific inhibitor for two specific proteases.

In the art, the sequence for such a substrate or inhibitor of a serine protease is often represented by . . . -P4-P3-P2-PI-P1'-P2'-P3'-P4'- . . . , where P and P' are amino acids and the proteolytic cleavage site, in the case of substrates, is defined to occur between residues P1 and P1'. Schechter, I. and Berger, A., Biochem. Biophys. Res. Commun., 27: 157 (1967). The bond between the P-carbonyl and the P'-nitrogen in substrate is often referred to as the scissile bond.

The primary specificity for a serine protease is defined by the nature of the residue immediately preceding the scissile bond. The residue, P1, corresponds to lysine 15 in the wild type or natural BPTI sequence. Residues surrounding the scissile bond taken together with residue P1 are often referred to as the "active site loop" of BPTI which is illustrated in (II). Laskowski, M. Jr. and Kato, I., Ann. Rev. Biochem. 49, 593–626 (1980).

| 12 | 13 | 14 | 15 | 16 | 17 | 18 | 19 | (II) |
|----|----|----|----|----|----|----|----|------|
| Gly | Pro | Cys | Lys | Ala | Arg | Ile | Ile | |
| P4 | P3 | P2 | P1 | P1' | P2' | P3' | P4' | |

(SEQ ID NO:2)

It is believed that P2, P3, P4, P1' P2', P3' and P4' convey secondary specificity to the inhibitor allowing differentiation among different serine proteases. In BPTI, a second loop consisting of residues 34–39 also form a contact region with the active sites of certain serine proteases and may contribute to specificity.

Analogues of BPTI having a more specific inhibitory effect toward certain serine proteases have been reported. Polypeptides consisting of residues 3 to 58 of BPTI, with the amino acids at positions 15 and 42 in one analogue, and at 15, 17 and 42 in another analogue changed, were reported to inhibit plasma kallikrein (Ki of 1 and 0.1 nM), Factor Xa with relatively weak inhibition constants of 1800 and 150 nM, but not factor VIIa or thrombin. Norris K. and Petersen L.C., "Aprotinin Analogues and Process for the Production Thereof", EP 339,942 (published Nov. 2, 1989).

Lipoprotein-associated coagulation inhibitor (LACI) from human plasma consists of three tandemly linked domains. Each of these domains shows homology with BPTI. This 276amino acid inhibitor was shown to inhibit factor Xa by its second domain, and factor VIIa-Tissue Factor complex by its first domain. Girard, T. J. et al., Nature 338: 518–520 (1989). Inhibition of the factor VIIa-tissue factor complex was weak in the absence of factor Xa, and increased significantly when factor Xa was present. Callander, S. et al., J. Biol. Chem. 267: 876–882 (1992, not admitted to be prior art to the present invention). A recombinant fusion protein consisting of the LACI first domain and the light chain of factor X was reported to be an inhibitor of the factor VIIa-tissue factor complex. Girard et al., EP 439,442 (published Jul. 31, 1991). A recombinant protein containing the first two domains of LACI is a factor VIIa-tissue factor inhibitor. Broze et al., U.S. Pat. No. 5,106,833 (Apr. 21, 1992, not admitted to be prior art to the present invention).

SUMMARY OF INVENTION

This invention concerns derivatives of BPTI engineered, as described below, to have potent inhibitory activity on the in vivo or in vitro biological activity of Factor VIIa-tissue factor (TF) complex. Thus, in a first aspect, the invention features a compound derived from BPTI which inhibits Factor VIIa-TF with an inhibition constant ($K_i$) of less than 500 nM, preferably less than 100 nM, and more preferably less than 10 nM.

The term "compound" refers not only to polypeptide chains having an amino acid sequence of 58 amino acids, as in the naturally occurring BPTI and its analogs, including human pancreatic trypsin inhibitor, but also to compounds which contain one or more of those amino acids substituted at locations which may not be relevant to their activity as Factor VIIa-TF inhibitors. For example, such substitutions may include substitution of glycine for valine, or of one or more charged amino acids for similarly or oppositely charged amino acids, or may include deletion of one or more amino acids. In addition, one or more amino acids may be introduced into the polypeptide chain of BPTI-analogs such that their introduction has little or no effect on the Factor VIIa-TF inhibitory activity of the BPTI derivative. Such substitution may be with any of the naturally occurring amino acids, or with unnatural amino acids which may be manufactured by standard procedures known in the art. In a particularly preferred aspect of the invention, the compound is derived by synthesizing a nucleic acid sequence (e.g., DNA or RNA) which encodes the desired amino acid sequence of the BPTI-analog incorporating changes at specific chosen locations to produce Factor VIIa-TF inhibitory activity in the resulting encoded BPTI-analog. Examples of such derivation are provided below, in which mutant BPTI compounds are formed by genetic engineering procedures.

The term "analog" refers to compounds found in nature or man-made, which are analogous to BPTI and have essentially the same two or three dimensional structure as BPTI as imposed by the three disulfide bonds of BPTI.

Specifically, compounds which are BPTI-analogs and possess Factor VIIa-TF inhibitory activity include those comprising, consisting of, or consisting essentially of the structure:

---

Cys Leu Glu Pro Pro Tyr $X_{11}$ Gly $X_{13}$ $X_{14}$ $X_{15}$ $X_{16}$ $X_{17}$ $X_{18}$ $X_{19}$ $X_{20}$ Tyr Phe Tyr Asn Ala Lys Ala Gly Leu Cys Gin Thr Phe $X_{34}$ $X_{35}$ Gly Gly $X_{38}$ $X_{39}$ Ala Lys Arg Asn Asn $X_{45}$ $X_{46}$ Ser Ala Glu Asp Cys Met Arg Thr Cys
(SEQ ID NO:3)

--- where:
$X_{11}$ is alanine, asparagine, aspartic acid, glutamic acid, glutamine, glycine, histidine, isoleucine, leucine, methionine, phenylalanine, proline, serine, threonine, tryptophan, tyrosine, or valine;
$X_{13}$ is alanine, arginine, asparagine, aspartic acid, glutamic acid, glutamine, glycine, histidine, isoleucine, leucine, lysine, methionine, phenylalanine, proline, serine, threonine, tryptophan, tyrosine, or valine;
$X_{14}$ is alanine, cysteine when $X_{,,}$ is cysteine, glycine or serine;
$X_{15}$ is arginine or lysine;
$X_{16}$ is alanine or glycine;
$X_{17}$ is alanine, arginine, asparagine, glutamine, glycine, histidine, isoleucine, leucine, lysine, methionine, phenylalanine, proline, serine, threonine, tryptophan, tyrosine, or valine;
$X_{18}$, $X_{19}$ and $X_{20}$ is any natural amino acid;
$X_{34}$, is alanine, arginine, asparagine, aspartic acid, glutamic acid, glutamine, glycine, histidine, isoleucine, leucine, lysine, methionine, phenylalanine, proline, serine, threonine, tryptophan, tyrosine, or valine;
$X_{35}$ is phenylalanine, tryptophan or tyrosine;
$X_{36}$ is alanine, glycine or serine;
$X_{38}$ is alanine, cysteine when $X_4$ is cysteine, glycine, or serine;
$X_{39}$ is alanine, arginine, asparagine, aspartic acid, glutamic acid, glutamine, glycine, histidine, isoleucine, leucine, lysine, methionine, phenylalanine, praline, serine, threonine, tryptophan, tyrosine, or valine;
$X_{45}$ is phenylalanine, tryptoptian or tyrosine, and
$X_{46}$ is any natural amino acid.

In a particularly preferred embodiment, examples of derived compounds include those having the structure:

---

$X_1$ Pro Asp Phe Cys Leu Glu Pro Pro Tyr $X_{11}$ Gly $X_{13}$ $X_{14}$ $X_{15}$ $X_{16}$ $X_{17}$ $X_{18}$ $X_{19}$ $X_{20}$ Tyr Phe Tyr Asn Ala Lys Ala Gly Leu Cys Gln Thr Phe $X_{34}$ $X_{35}$ Gly Gly $X_{38}$ $X_{39}$ Ala Lys Arg Asn Asn $X_{45}$ $X_{46}$ Ser Ala Glu Asp Cys Met Arg Thr Cys Gly Gly Ala
(SEQ ID NO:4)

--- where:
$X_1$ is alanine or arginine;
$X_{11}$ is alanine, aspartic acid, glutamic acid, glycine, proline, serine, threonine, or valine;
$X_{13}$ is alanine, glutamine, histidine, isoleucine, leucine, methionine, phenylalanine, proline, tryptophan, tyrosine, or valine;
$X_{14}$ is cysteine;
$X_{15}$ is arginine, or lysine;
$X_{16}$ is alanine or glycine;
$X_{17}$ is alanine, isoleucine, leucine, methionine, or tyrosine;
$X_{18}$ is histidine, isoleucine, phenylalanine or tyrosine;
$X_{19}$ is asparagine, glutamine, histidine, isoleucine, leucine, lysine, proline, threonine, or valine;
$X_{20}$ is arginine or serine;
$X_{34}$ is aspartic acid, histidine, isoleucine, leucine, phenylalanine, serine, threonine, tryptophan, tyrosine, or valine;
$X_{35}$ is tyrosine;
$X_{36}$ is glycine;
$X_{38}$ is cysteine;
$X_{39}$ is arginine, asparagine, glutamic acid, glycine, histidine, leucine, methionine, phenylalanine, tryptophan, or tyrosine;
$X_{45}$ is phenylalanine; and
$X_{46}$ is aspartic acid, glutamic acid, lysine, phenylalanine, tryptophan or tyrosine.

In a second aspect, the invention features an isolated nucleic acid segment encoding a compound as described above.

By "isolated" is meant that the nucleic acid is provided in a state that does not occur naturally in nature (although its sequence of nucteotides may be identical to a naturally occurring sequence), and is preferably located within a host cell genome, or an expression vector, or other vector such that it can be replicated and transcribed and translated to form a desired inhibitor of the invention. The term may also indicate a homogenous solution of the nucleic acid.

In preferred embodiments, the nucleic acid segment includes at least 150 bases and is provided within a vector, for example, a plasmid, phasmid, cosmid, or phage, with a promoter region which controls transcription of the nucleic acid segment.

In a related aspect, the invention features a host cell including such a vector.

The phrase "promoter region", and the term "transcription" are used in their art recognized manner.

A further aspect of the invention features a method for preparing a compound, as described above, by growing a host cell which includes a vector encoding the compound under conditions in which the vector causes expression of the compound within the cell. Preferably, the compound is linked to a secretion signal sequence which causes it to be secreted into the periplasmic space or the culture supernatant.

In a preferred embodiment, one method of preparing the compound includes: (a) initiating a culture in a nutrient medium of host cells transformed with an expression vector encoding the compound; (b) maintaining the culture for a sufficiently long time to allow production of the compound; and (c) recovering the compound from the culture.

The present invention also includes pharmaceutically acceptable compositions prepared for storage and subsequent administration which include a pharmaceutically effective amount of an above-described compound in a pharmaceutically acceptable carrier or diluent.

The present invention also includes a method for preventing or treating a condition in a mammal characterized by the abnormal appearance or amount of tissue factor and/or factor VIIa, by administering a therapeutic quantity of a compound of the invention. For example, the invention features a method for preventing or treating a condition in a mammal characterized by abnormal thrombosis. The term "abnormal" indicates an amount or type of tissue factor or factor VIIa different from that observed in a general population of mammals, and is a term recognized in the art.

Other features and advantages of the invention will be apparent from the following description of the preferred embodiments thereof, and from the claims.

BRIEF DESCRIPTION OF DRAWINGS

The drawings will first briefly be described.
Drawings

FIG. 3 shows the DNA sequence (5' to 3') of the four oligonucteotides that were used to assemble the BPTI coding region.

FIGS. 4A and 4B shows the DNA sequence of various oligonucleotides used for construction of pMa5-PI. Specifically, FIG. 4A shows the relevant part of the recipient vector pMa5-19 or pMc5-19, collectively referred to as pMa/c5-19. [As used in these abbreviations for vector constructs, "a" refers to a sequence conveying ampicillin resistance, "c" refers to a sequence conveying chloramphenicol resistance, and "a/c" refers to sequences conveying resistance to both ampicillin and chloramphenicol.] The EcoRI/Xbal fragment is present in the multicloning site of pMa/c5–8 (Stanssens et al., Nucl. Acids Res. 17, 4441–4454, (1989). The −35 and −10 box of the $P_{tac}$ promoter, the Shine-Dalgarno (SD) sequence and secretion signal derived from the phoA gene as well as some relevant restriction sites are indicated. FIG. 4B shows the double stranded BPTI-encoding fragment composed of the four chemically synthesized oligonucleotides. The BPTI-oligonucleotides were ligated with the pMc5-19 vector which had been opened with KpnI, treated with DNA polymerase I (Klenow fragment), and subsequently digested with HindIII to yield PMc5-PI. This fuses the 5'-end of the BPTI coding region to the phoA secretion signal while the HindIII-junction at the 3'-end generates an in-frame TAA translational stop codon.

DETAILED DESCRIPTION OF THE PREFERRED EMBODIMENTS

BPTI Derivatives

Figure 1:
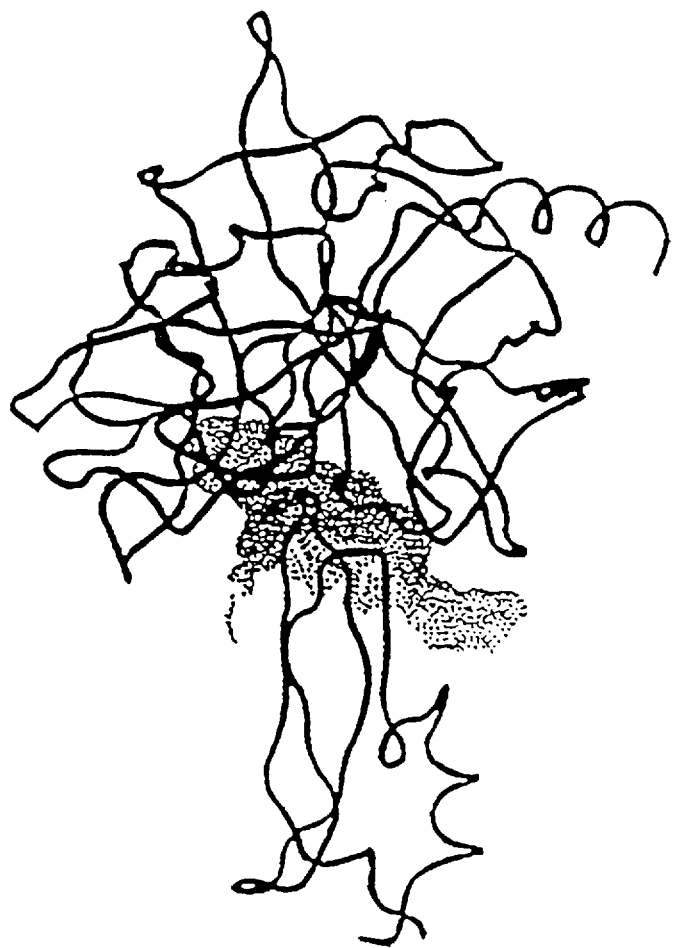
FIG. 1 is a representation of the three dimensional interaction between the surface of a BPTI molecule and a model of the Factor VIIa substrate binding site. The dotted surface represents that part of the BPTI molecule which is expected to be in contact with the substrate binding site of Factor VIIa. The polypeptide chains of the BPTI molecule (below) and Factor VIIa (above) are represented by black ribbons.

The specificity of BPTI for specific serine proteases (e.g., trypsin, plasmin) is determined by the nature of the amino acids which constitute that part of the surface of the BPTI molecule which is in contact with the protease substrate binding site. The dotted surface shown in FIG. 1 represents that part of the BPTI molecule which applicant predicts to be in contact with the substrate binding sites of Factor VIIA (assuming that the protease domain of factor VIIa in complex with tissue factor resembles trypsin in structure). The polypeptide chain of the BPTI molecule is represented by the lower black ribbon.

Compounds can be derived from BPTI, by replacing, inserting or deleting amino acids, in such a way that the contact surface is modified so as to be optimally compatible with the Factor VIIa-TF structure in shape, charge, polarity and hydrophobicity. The compounds thus derived from BPTI are potent Factor VIIa-TF inhibitors, whereas BPTI itself only weakly inhibits Factor VIIa-TF. Modifying, or even removing, amino acids outside the contact region should not affect the binding properties of the inhibitor as long as the structure of the contact region is not disturbed by such changes.

From inspection of a BPTI model similar to the one represented in FIG. 1, it can be deduced that the shape of the contact region is largely, but not exclusively, defined by residues 11, 13, 14, 15, 16, 17, 18, 19, 20, 34, 35, 36, 38, 39, 45, and 46. Thus, BPTI-derived inhibitors of this invention have modifications at these sites to enhance their inhibitory activity, and may have changes at other sites which have little or no effect on such modifications. These inhibitors have the basic BPTI structure optimized to inhibit the activity of Factor VIIa-TF in vivo and in vitro. Such derivatives can be formed by standard procedures, as discussed below. Identification of optimal changes in the BPTI structure, however, can be performed by a randomized mutagenic procedure, or by systematic changes in BPTI amino acid sequence or structure. There follows examples of these procedures, which are not limiting in this invention.

Site-Directed Mutagenesis

Factor VIIa-TF inhibitors useful in this invention can be identified by site-directed mutagenesis of the BPTI gene expressed in a micro-organism. For example, a synthetic gene can be constructed in a vector and mutagenized by standard procedure using the methodology described in Stanssens et al., Nucl. Acids Res. 17: 4441–4454 (1989). Specifically, the BPTI coding region can be chemically synthesized so that the nucleotide sequence is adapted to match the *E. coli* codon usage (i.e., the synthesized gene is made devoid of AGA and AGG Arg-modulator-codons which adversely affect polypeptide production); strategically placed restriction sites which facilitate other genetic manipulations can be incorporated; and arginine at position 1 replaced by an alanine to allow proper processing by the *E. coli* signal peptidase.

Figure 2:
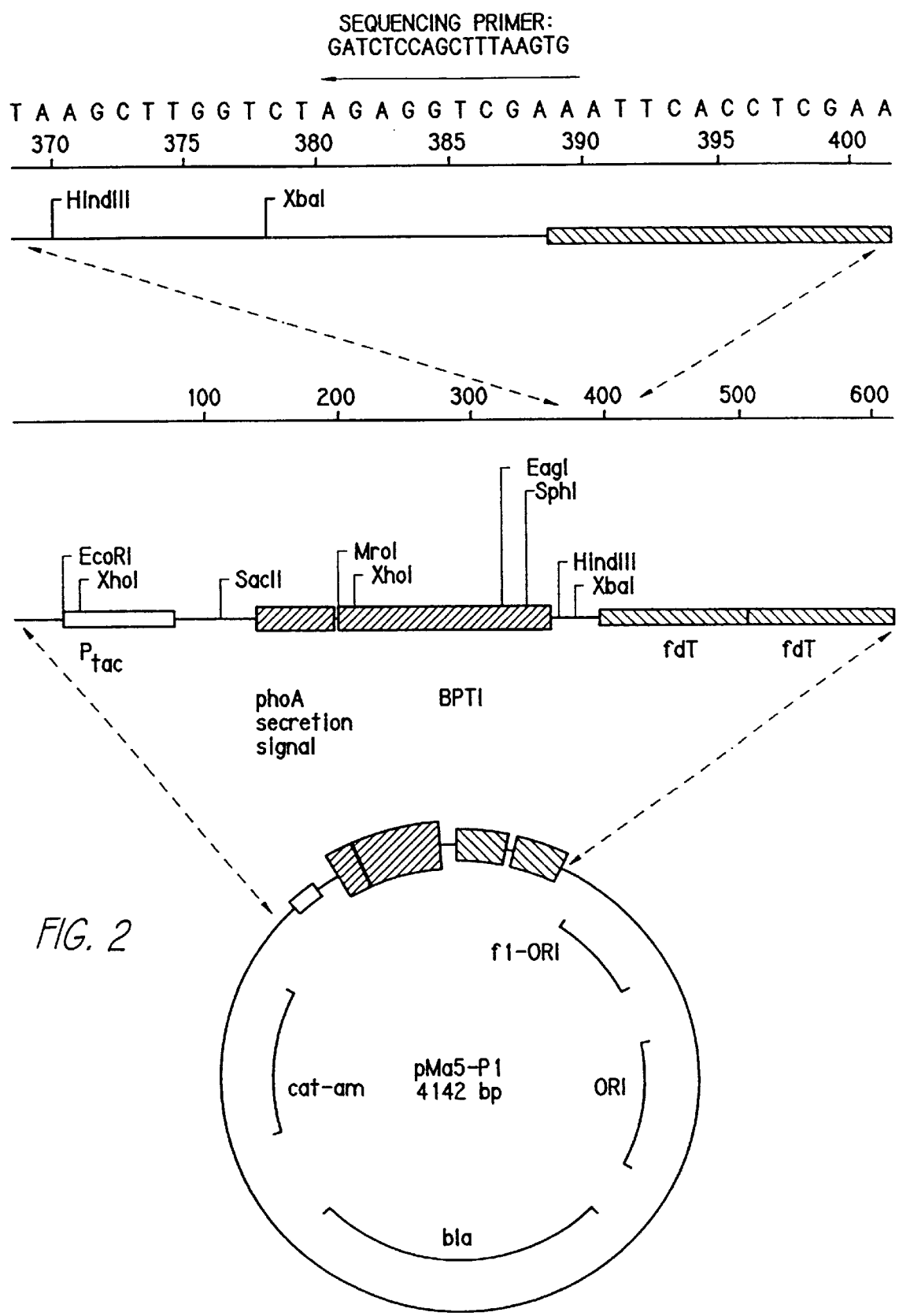
FIG. 2 is a diagrammatic representation of the vector pMa5-PI. The map of pMa5-PI contains the following features: (i) a ColEl type origin of replication (ORI); (ii) the intergenic region of filamentous phage fl, including the origin of replication (fl ORI); (iii) the betalactamase gene which confers resistance to ampicillin (bla); (iv) the chloramphenicol acetyl transferase gene made non-functional by a mutation introducing an amber stop codon (cat-am); (v) the $P_{tac}$/phoA/BPTI expression cassette; (vi) two copies of the central transcription terminator of phage fd (fdT). The complementary vector pMc5-PI is identical to pMa5-PI except that the cat gene is functional (conferring resistance to chloramphenicol) and the bla gene contains an amber stop codon. The blown-up region shows the position of the $P_{tac}$ promoter, the DNA segment coding for the phoA secretion signal, the BPTI-derived gene, and the relevant restriction sites. A sequencing primer anneals to vector sequences immediately downstream of the BPTI coding region, as shown in the upper part of the figure, and can be used to determine the DNA sequence encoding a useful Factor VIIa-TF inhibitor of this invention.
Figure 5:
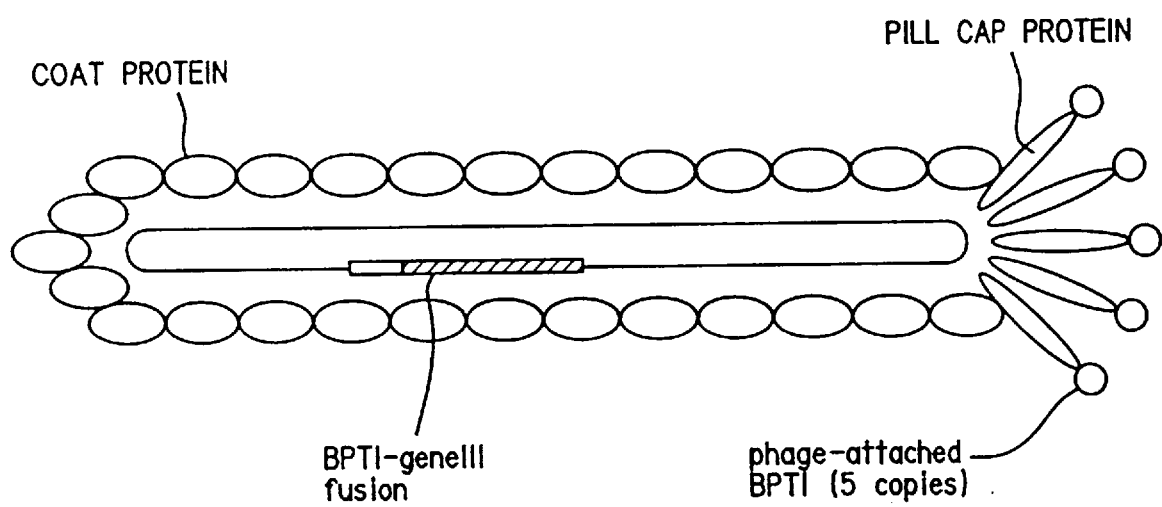
FIG. 5 is a schematic diagram of a filamentous phage displaying five copies of a mutant BPTI-derived protein fused to the PIII coat protein.

To establish an *E. coli* expression system that would produce native, correctly folded and disulfide-bonded BPU derivatives, the BPTI-derived mutant protein can be directed to the periplasmic space by fusion of the gene to a DNA fragment encoding a secretion signal peptide. The BPTI derivative encoding oligonucleotides can then be ligated directly into pMa/c5-19. [pMa/c5-19 refers collectively to pMa5-19 or pMc5-19.] This vector (FIG. 2), contains an IPTG-inducible $P_{tac}$ promoter, and the secretion signal-encoding part of the alkaline phosphatase (phoA) gene which can be made accessible by virtue of a KpnI site. Stanssens et al., Nucl. Acids Res. 17, 4441–4454 (1989). The sequences of four oligonucleotides which can be used to assemble a BPTI derivative-coding region are shown in FIG. 3. FIG. 4 shows the relevant parts of the pMa/c5-19 vector and the complete BPTI derivative-encoding nucleic acid fragment. The construction of the BPTI-analog gene in the pMa/c5-19 vector is described in detail in Example 1, below.

The vectors pMa5-PI and pMc5-PI are useful in this invention since they harbor the intergenic region of filamentous phage f1, thus allowing expression, oligonucleotide-directed mutagenesis, and sequencing to be carried out from the same replicon. Mutation construction experiments were carried out essentially as described by Stanssens et al., Nucl. Acids Res. 17: 4441–4454 (1989). The construction of the genes encoding the inhibitory BPTI-derived compounds named 82c5 and 95c12 is described in Example 2.

For large scale production, the specific inhibitor-encoding genes can be transferred to a secretion production system such as, for example, the Pichia yeast expression system (Phillips Petroleum Company). The vector used for expression of a particular factor VIIa-TF inhibitor is described in Example 10. Recombinant protein can be purified from the culture medium using standard methods, such as ion exchange chromatography and affinity chromatography. An example of a purification protocol is given in Example 3.

Random Mutagenesis

Specific factor VIIA-TF inhibitors can also be obtained by random mutagenesis of the entire BPTI gene or of a specific set of residues included in the protease-inhibitor contact region. Such a library of mutant BPTI-derived polypeptides can be screened for inhibition of factor VIIa-TF using an appropriate enzymatic assay, such as described in Example 4. Alternatively, a method can be developed to isolate potent factor VIIA-TF inhibitors. For example, a method has been described to express mutant-BPTI as a fusion protein with a filamentous phage coat protein. Ladner et al., U.S. Pat. No. 5,096,815 (Mar. 17, 1992). Phages displaying factor VIIA-TF inhibitors can be isolated by a process called "panning". Parmley et al., Gene 73: 305–318 (1988). An example of the construction of a particular mutant-BPTI libraries is given below (Example 7). Panning protocols are described in Example 8.

Preferred BPTI-derived compounds

The preferred compounds of the present invention are those having a Ki for factor VIIa-TF smaller than 500 nM. Examples of these compounds are given in the following list.

These inhibitors have the same amino acid sequence as BPTI except for the substitutions shown within brackets.

---

BPTI(1Ala 11Asp 17Ile 19Lys 39Glu 46Glu) (SEQ ID NO:5)
BPTI(1Ala 11Glu 17Ile 19Lys 39Glu 46Glu) (SEQ ID NO:6)
BPTI(1Ala 13Ile 15Arg 17Tyr 19Lys 39Leu 46Glu) (SEQ ID NO:7)
BPTI(1Ala 11Asp 15Arg 17Ile 19Lys 39Glu 46Glu) (SEQ ID NO:8)
BPTI(1Ala 11Asp 15Arg 17Ile 19Lys 34Asp 39Leu) (SEQ ID NO:9)
BPTI(1Ala 15Arg 17Tyr 19Tyr 39Phe 46Glu) (SEQ ID NO:10)
BPTI(1Ala 11Asp 17Ile 19Lys 39Phe 46Glu) (SEQ ID NO:11)
BPTI(1Ala 11Asp 17Ile 19Lys 39Tyr 46Glu) (SEQ ID NO:12)
BPTI(1Ala 11Asp 15Arg 17Ile 19Lys 39Phe 46Glu) (SEQ ID NO:13)
BPTI(1Ala 11Asp 15Arg 17Ile 19Lys 39Tyr 46Glu) (SEQ ID NO:14)
BPTI(1Ala 15Arg 17Ile 19Lys 39Phe 46Glu) (SEQ ID NO:15)
BPTI(1Ala 15Arg 17Tyr 19Thr 39Tyr 46Tyr) (SEQ ID NO:16)

BPTI(1Ala 11Glu 15Arg 17Tyr 19Thr 39Tyr 46Glu) (SEQ ID NO:17)
BPTI(1Ala 15Arg 17Met 18His 19His 39Phe 46Glu) (SEQ ID NO:18)
BPTI(1Ala 11Asp 15Arg 17Leu 18His 19Leu 34Tyr 39Leu 46Glu) (SEQ ID NO:19)
BPTI(1Ala 11Glu 13Tyr 15Arg 17Leu 18His 34Tyr 39His 46Glu) (SEQ ID NO:20)
BPTI(1Ala 11Glu 13Ala 15Arg,17Leu 18His 19Leu 34Tyr 39Tyr 46Glu) (SEQ ID NO:21)
BPTI(1Ala 11Glu 13Phe 15Arg 17Leu 18His 19Pro 34Tyr 39His 46Glu) (SEQ ID NO:22)
BPTI(1Ala 11Glu 13Phe 15Arg 17Leu 18His 19Thr 34Tyr 39His 46Glu) (SEQ ID NO:23)
BPTI(1Ala 11Asp 15Arg 17Leu 18His 19Thr 34Thr 39Phe 46Glu) (SEQ ID NO:24)
BPTI(1Ala 11Pro 13Tyr 15Arg 17Leu 18His 19Leu 34Thr 39His 46Glu) (SEQ ID NO:25)
BPTI(1Ala 11Asp 15Arg 17Leu 18His 19Gln 34Thr 46Glu) (SEQ ID NO:26)
BPTI(1Ala 11Glu 15Arg 17Ile 18His 19Pro 34Leu 39Tyr 46Glu) (SEQ ID NO:27)
BPTI(1Ala 11Gly 13Val 15Arg 17Ile 18His 19Leu 34Ile 39Tyr 46Glu) (SEQ ID NO:28)
BPTI(1Ala 11Ala 15Arg 17Leu 18His 19Gin 34His 39Phe 46Glu) (SEQ ID NO:29)
BPTI(1Ala 11Pro 13Tyr 15Arg 17Leu 18His 19Leu 34His 39His 46Glu) (SEQ ID NO:30)
BPTI(1Ala 11Gly 15Arg 17Leu 18His 19Pro 34Phe 39Phe 46Glu) (SEQ ID NO:31)
BPTI(1Ala 11Gly 13Val 15Arg 17Leu 18His 34Tyr 39Asn 46Glu) (SEQ ID NO:32)
BPTI(1Ala 11Glu 13Gln 15Arg 17Leu 18His 19Leu 34Ser 39Tyr 46Glu) (SEQ ID NO:33)
BPTI(1Ala 11Ala 13Tyr 15Arg 17Ile 18His 19His 39Tyr 46Glu) (SEQ ID NO:34)
BPTI(1Ala 13Ile 15Arg 17Ile 18His 19His 39Leu 46Glu) (SEQ ID NO:35)
BPTI(1Ala 11Pro 15Arg 17Leu 18His 19Thr 34Phe 39Tyr 46Glu) (SEQ ID NO:36)
BPTI(1Ala 11Val 13His 15Arg 17Leu 18His 19Leu 34Leu 39His 46Glu) (SEQ ID NO:37)
BPTI(1Ala 13Ile 15Arg 17Leu 18His 19Gln 39Leu 46Glu) (SEQ ID NO:38)
BPTI(1Ala 13Ile 15Arg 17Leu 18His 39Leu 46Glu) (SEQ ID NO:39)
BPTI(1Ala 13Ile 15Arg 17Leu 18His 19Thr 39Leu 46Glu) (SEQ ID NO:40)
BPTI(1Ala 13Ile 15Arg 17Leu 18His 19Lys 39Leu 46Glu) (SEQ ID NO:41)
BPTI(1Ala 13Ile 15Arg 17Ile 18His 19Leu 39Leu 46Glu) (SEQ ID NO:42)
BPTI (1Ala 13Ile 15Arg 17Ile 18His 19Val 39Leu 46Glu) (SEQ ID Nb:43)
BPTI(1Ala 13Ile 15Arg 17Met 18His 19Leu 39Leu 46Glu) (SEQ ID NO:44)
BPTI(1Ala 13Ile 15Arg 17Tyr 18Tyr 19Lys 39Leu 46Glu) (SEQ ID NO:45)
BPTI (1Ala 11Pro 13Phe 15Arg 17Leu 18His 19Lys 34His 39Phe 46Glu) (SEQ ID NO:46)
BPTI (11Asp 15Arg 17Leu 18His 19Pro 34Trp 39Tyr 46Glu) (SEQ ID NO:47)
BPTI (11Asp 15Arg 17Leu 18His 19Pro 34Trp 39Leu 46Glu) (SEQ ID NO:48)
BPTI(11Asp 15Arg 17Leu 18His 19His 34Tyr 46Glu) (SEQ ID NO:49)
BPTI (11Glu 13Trp 15Arg 17Leu 18His 19His 34Ile 39Gly 46Glu) (SEQ ID NO:50)
BPTI(15Arg 17Leu 18His 19His 34Phe 39Phe 46Glu) (SEQ ID NO:51)
BPTI (11Ser 13Leu 15Arg 17Leu 18His 19Lys 34Tyr 34Tyr 46Glu) (SEQ ID NO:52)
BPTI (11Pro 13Ile 15Arg 17Leu 18His 19Lys 34His 39Phe 46Glu) (SEQ ID NO:53)
BPTI(11Ser 13Leu 15Arg 17Leu 18His 19Lys 34Tyr 39Phe 46Glu) (SEQ ID NO:54)
BPTI (11Pro 13Ile 15Arg 17Leu 18His 19Lys 34Tyr 39Met 46Glu) (SEQ ID NO:55)
BPTI (11Glu 13Met 15Arg 17Ile 18His 19Lys 34Thr 39Met 46Glu) (SEQ ID Nd:56)
BPTI (11Pro 13Val 15Arg 17Leu 18His 19Lys 345er 39Gln 46Glu) (SEQ ID NO:57)
BPTI (11Glu 13Leu 15Arg 17Leu 18His 19Lys 34Tyr 39Phe 46Glu) (SEQ ID NO:58)
BPTI (11Pro 13Leu 15Arg 17Leu 18His 19Lys 34Tyr 39Tyr 46Glu) (SEQ ID NO:59)
BPTI(11Asp 15Arg 17Leu 18His 19Gln 39Phe 46Glu) (SEQ ID NO:60)
BPTI(9Ala 11Asp 15Arg 17Leu 18His 19Gln 22Leu 39Phe 46Glu) (SEQ ID NO:61)
BPTI(13Ile 15Arg 17Ala 18Phe 19Asn 39Leu 46Glu) (SEQ ID NO:62)
BPTI(13Ile 15Arg 17Phe 18Tyr 19Lys 39Leu 46Glu) (SEQ ID NO:63)
BPTI(13Ile 15Arg 17Tyr 18Tyr 19Lys 39Leu 46Glu) (SEQ ID NO:64)

Yet other preferred derivatives are those compounds characterized by a Ki for factor VIIa-TF smaller than 50 nM. These include:

BPTI(1Ala 11Asp 15Arg 17Ile 19Lys 39Glu 46Glu) (SEQ ID NO:65)
BPTI(1Ala 11Asp 17Ile 19Lys 39Phe 46Glu) (SEQ ID NO:66)
BPTI(1Ala 11Asp 17Ile 19Lys 39Tyr 46Glu) (SEQ ID NO:67)
BPTI(1Ala 11Asp 15Arg 17Ile 19Lys 39Phe 46Glu) (SEQ ID NO:68)
BPTI(1Ala 11Asp 15Arg 17Ile 19Lys 39Tyr 46Glu) (SEQ ID NO:69)
BPTI(1Ala 15Arg 17Ile 19Lys 39Phe 46Glu) (SEQ ID NO:70)
BPTI(1Ala 11Glu 15Arg 17Tyr 19Thr 39Tyr 46Glu) (SEQ ID NO:71)
BPTI(1Ala 15Arg 17Met 18His 19His 39Phe 46Glu) (SEQ ID NO:72)
BPTI(1Ala 11Asp 15Arg 17Leu 18His 19Leu 34Tyr 39Leu 46Glu) (SEQ ID NO:73)
BPTI(1Ala 11Glu 13Tyr 15Arg 17Leu 18His 34Tyr 39His 46Glu) (SEQ ID NO:74

-continued

BPTI(1Ala 11Glu 13Ala 15Arg 17Leu 18His 19Leu 34Tyr 39Tyr 46Glu) (SEQ ID NO:75)
BPTI(1Ala 11Glu 13Phe 15Arg 17Leu 18His 19Pro 34Tyr 39His 46Glu) (SEQ ID NO:76)
BPTI(1Ala 11Glu 13Phe 15Arg 17Leu 18His 19Thr 34Tyr 39His 46Glu) (SEQ ID NO:77)
BPTI(1Ala 11Asp 15Arg 17Leu 18His 19Thr 34Thr 39Phe 46Glu) (SEQ ID NO:78)
BPTI(1Ala 11Pro 13Tyr 15Arg 17Leu 18His 19Leu 34Thr 39His 46Glu) (SEQ ID NO:79)
BPTI(1Ala 11Asp 15Arg 17Leu 18His 19Gln 34Thr 46Glu) (SEQ ID NO:80)
BPTI(1Ala 11Glu 15Arg 17Ile 18His 19Pro 34Leu 39Tyr 46Glu) (SEQ ID NO:81)
BPTI(13Ile 15Arg 17Leu 18His 39Leu 46Glu) (SEQ ID NO:82)
BPTI(11Asp 15Arg 17Leu 18His 19Thr 34Thr 39Phe 46Glu) (SEQ ID NO:83)
BPTI(11Gly 13Val 15Arg 17Ile 18His 19Leu 34Ile 39Tyr 46Glu) (SEQ ID NO:84)
BPTI(11Gly 15Arg 17Ile 18His 19Pro 34Leu 39Tyr 46Glu) (SEQ ID NO:85)
BPTI(11Asp 15Arg 17Leu 18His 19Gln 34Thr 46Glu) (SEQ ID NO:86)
BPTI(11Glu 13Phe 15Arg 17Leu 18His 19Thr 34Tyr 39Tyr 46Glu) (SEQ ID NO:87)
BPTI(11Glu 13Ala 15Arg 17Leu 18His 19Leu 34Tyr 39Tyr 46Glu) (SEQ ID NO:88)
BPTI(11Asp 15Arg 17Leu 18His 19Leu 34Tyr 39Leu 46Glu) (SEQ ID NO:89)
BPTI(11Glu 13Tyr 15Arg 17Leu 18His 34Tyr 39His 46Glu) (SEQ ID NO:90)
BPTI(11Pro 13Tyr 15Arg 17Leu 18His 19Leu 34Thr 39His 46Glu) (SEQ ID NO:91)
BPTI(11Asp 15Arg 17Leu 18His 19Pro 34Trp 39Tyr 46Glu) (SEQ ID NO:92)
BPTI(11Asp 15Arg 17Leu 18His 19Pro 34Trp 39Leu 46Glu) (SEQ ID NO:93)
BPTI(11Asp 15Arg 17Leu 18His 19His 34Tyr 46Glu) (SEQ ID NO:94)
BPTI(11Glu 13Trp 15Arg 17Leu 18His 19His 34Ile 39Gly 46Glu) (SEQ ID NO:95)
BPTI(15Arg 17Leu 18His 19His 34Phe 39Phe 46Glu) (SEQ ID NO:96)
BPTI(11Ser 13Leu 15Arg 17Leu 18His 19Lys 34Tyr 39Tyr 46Glu) (SEQ ID NO:97)
BPTI(11Pro 13Ile 15Arg 17Leu 18His 19Lys 34His 39Phe 46Glu) (SEQ ID NO:98)
BPTI(11Ser 13Leu 15Arg 17Leu 18His 19Lys 34Tyr 39Phe 46Glu) (SEQ ID NO:99)
BPTI(11Pro 13Ile 15Arg 17Leu 18His 19Lys 34Tyr 39Met 46Glu) (SEQ ID NO:100)
BPTI(11Glu 13Met 15Arg 17Ile 18His 19Lys 34Thr 39Met 46Glu) (SEQ ID NO:101)
BPTI(11Pro 13Val 15Arg 17Leu 18His 19Lys 34Ser 39Gln 46Glu) (SEQ ID NO: 102)
BPTI(11Glu 13Leu 15Arg 17Leu 18His 19Lys 34Tyr 39Phe 46Glu) (SEQ ID NO:103)
BPTI(11Pro 13Leu 15Arg 17Leu 18His 19Lys 34Tyr 39Tyr 46Glu) (SEQ ID NO:104)
BPTI(11Asp 15Arg 17Leu 18His 19Gln 39Phe 46Glu) (SEQ ID NO:105)
BPTI (9Ala 11Asp 15Arg 17Leu 18His 19Gln 22Leu 39Phe 46Glu) (SEQ ID NO:106)

Yet other preferred derivatives are those compounds characterized by a Ki for factor VIIa-TF smaller than 5 nM. These include:

BPTI(11Asp 15Arg 17Leu 18His 19Gln 34Thr 46Glu) (SEQ ID NO:107)
BPTI(11Asp 15Arg 17Leu 18His 19Leu 34Tyr 39Leu 46Glu) (SEQ ID NO:108)
BPTI(11Glu 13Tyr 15Arg 17Leu 18His 34Tyr 39His 46Glu) (SEQ ID NO:109)
BPTI(11Asp 13Arg 17Leu 18His 19Pro 34Trp 39Tyr 46Glu) (SEQ ID NO:110)
BPTI(11Asp 15Arg 17Leu 18His 19Pro 34Trp 39Leu 46Glu) (SEQ ID NO:111)
BPTI(11Asp 15Arg 17Leu 18His 19His 34Tyr 46Glu) (SEQ ID NO:112)
BPTI(11Ser 13Leu 15Arg 17Leu 18His 19Lys 34Tyr 39Phe 46Glu) (SEQ ID NO:113)
BPTI(11Glu 13Leu 15Arg 17Leu 18His 19Lys 34Tyr 39Phe 46Glu) (SEQ ID NO:114)
BPTI(9Ala 13Asp 15Arg 17Leu 18His 19Gln 22Leu 39Phe 46Glu) (SEQ ID NO:115)

Utility and Formulation

Blood coagulation is the culmination of a series of amplified reactions in which several specific zymogens of serine proteases are activated by limited proteolysis. The initiation and propagation of the activation reactions occurs through the extrinsic and intrinsic pathways of coagulation. Mackie, I. J. and Bull, H. A., *Normal Hemostasis and its Regulation*, Blood Reviews, 3: 237–250 (1989). Both pathways are highly interdependent and converge in the formation of Factor Xa. Factor Xa catalyses the penultimate step in the blood coagulation cascade which is the formation of thrombin. Thrombin cleaves fibrinogen in the plasma resulting in clot formation. One of the early events in coagulation is the expression of tissue factor when the endothelium cell lining the blood vessels are damaged. Activated factor VIIa (VIIa) bound to tissue factor activates factor IX and factor X, and thus plays an important role by initiating both intrinsic and extrinsic pathways of blood coagulation.

By interfering at an early stage in the coagulation cascade, potent and selective Factor VIIa-TF inhibitors of this activating activity can be used as therapeutic agents for diseases associated with the expression of tissue factor, especially those diseases related to abnormal hemostasis. For example, Factor VIIA-TF inhibitors can be used to prevent reocclusion during thrombolytic therapy or angioplasty. They also can be used for the treatment of disseminated intravascular coagulopathy associated with septic shock, certain viral infections and cancer. This is further illustrated by the example that recombinant Tissue Factor Pathway Inhibitor protects rabbits against endotoxin initiated disseminated intravascular coagulation.

Most preferred compounds of this invention are selective inhibitors of the Factor VIIa-TF complex. This can be an important feature with respect to the ability of the compounds to control pathogenic thrombosis formation, with minimal effects on the hemostatic potential of the treated patient. This results in a reduction in the incidence of associated bleeding complications during therapy. A compound of the present invention is said to have "selectivity" for the Factor VIIa-TF complex relative to another serine protease (except trypsin) when the ratio of the inhibitor constants, (Ki for other enzyme/Ki for Factor VIIa-TF complex) is about 10, and more preferably about 100. In this case, the Ki of a compound of the present invention is determined for Factor VIIa-TF complex and for other coagulation enzymes, such as kallikrein, Factor XIa, Factor VIIa, Factor Xa, Thrombin; the fibrinolysis enzymes, Plasmin, Tissue Plasminogen Activator (tPA), and Urokinase (UK), and the anticoagulation enzyme, Protein C. Preferably, the Ki for Plamin or Protein C is compared to that of factor VIIa-TF complex to assess selectivity of the compounds of the present invention. Even without this advantage, inhibitors of this invention which do not have such specificity are useful.

The present invention also encompasses pharmaceutical compositions prepared for storage and subsequent administration, which have a pharmaceutically effective amount of the compounds disclosed above in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of non toxic auxiliary substances, such as wetting agents, pH buffering agents, and the like. If desired, absorption enhancing preparations (e.g., liposomes) may be utilized.

The present invention also includes a method for preventing or treating a condition in mammals characterized by abnormal thrombosis. The pharmaceutically effective amount of the composition required as a dose will depend on the route of administration, the type of mammal being treated, and the physical characteristics of the specific mammal under consideration. The dose can be tailored to achieve optimal efficacy but will depend on such factors as weight, diet, concurrent medication and other factors which those skilled in the medical arts will recognize.

In practicing the methods of the invention, the compounds or compositions can be used alone or in combination with one another, or in combination with other therapeutic or diagnostic agents. These compounds can be utilized in vivo, ordinarily in a mammal, preferably in a human, or in vitro. In employing them in vivo, the compounds or compositions can be administered to the mammal in a variety of ways, including parenterally, intravenously, subcutaneously, intramuscularly, colonically, rectally, nasally or intraperitoneally, employing a variety of dosage forms.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, will be within the ambit of one skilled in the art. Typically, applications of compound are commenced at lower dosage levels, with dosage level being increased until the desired effect is achieved.

The dosage for the compounds of the present invention can range broadly depending upon the desired effects and the therapeutic indication. Typically, dosages will be between about 0.01 µg/kg and 100 mg/kg body weight, preferably between about 0.01 µg/kg and 10 mg/kg body weight. Administration is preferably parenteral, such as intravenous on a daily basis.

EXAMPLE 1

Construction of the BPTI Gene in pMa5-PI Vector

A BPTI coding region was assembled making use of four chemically synthesized oligonucleotides (e.g., Pst205, a 74-mer; Pst206, a 78-mer; Pst207, a 102-mer and Pst208, a 102-mer; see FIG. 3). Following synthesis, the oligonucleotides were purified by preparative gel electrophoresis and enzymatically phosphorylated. Subsequently, the oligonucteotides were allowed to anneal pairwise: to this end, a 20 µl mixture containing 50 pmoles of each of the appropriate oligonucleotides was heated to 100° C. for 3 minutes, after which the mixture was allowed to cool to room temperature (about 20° C.). Annealing of the oligonucleotides Pst205 and Pst206 yields a blunt-ended StyI fragment; similarly, the oligonucleotides Pst207 and Pst208 form a StyI/HindIII fragment. Together these fragments make up the entire double-stranded BPTI coding region shown in FIG. 4B.

The recipient pMc5-19 was opened by KpnI restriction, treated with DNA polymerase I (Klenow fragment) to resect the 3'-overhanging ends, and subsequently digested with HindIII (FIG. 4A; other equivalent vectors can be readily designed and used by standard procedures). This material was ligated with the two above-mentioned BPTI-fragments. The lacI$^q$ strain WK6 was transformed with the ligation mixture. Other *E. coli* strains containing the lacI$^q$ allele, into which one could transform this vector, include JM101, 71-18 (Yanish-Perron et al., Gene, 33:103–199 (1985)), or XLI-Blue (Bullock et al., Biotechniques, 5: 376–379 (1987)).

Based on a restriction analysis of 12 randomly picked Cm$^R$ transformants, five clones (designated c2, c8, c9, c10 and c11) were retained. Sequence determination of these clones confirmed the precise junction between the phoA signal and the BPH coding region predicted by the construction scheme; all five clones were, however, found to contain one or more unwanted nucleotide substitutions. The clones c9 (contains a C→A substitution resulting in the Asn43Lys amino acid replacement) and c10 (a C→G substitution results in a Leu to Val mutation) were used to construct a vector which encodes wild type BPTI; to this end the small EcoRI/StyI fragment of c9 and the small StyI/HindIII fragment of c10 were both purified from polyacrylamide gel and ligated to pMa5-8 digested with EcoRI and HindIII. One of the obtained clones displaying the correct restriction pattern was retained. This clone, which was shown to contain the intended BPTI coding region by sequence determination, was designated pMa5-PI. For mutation construction purposes we also constructed the complementary pMc5-PI. The latter vector was obtained by transferring the EcoRI/XbaI (an XbaI site is present immediately downstream of the HindIII site; see FIG. 4) expression cassette from pMa5-PI to pMc5–8.

Upon derepression of the P$_{tac}$ promoter, WK6 cells, harboring either pMa5-PI or pMc5-PI, were found to direct the synthesis of BPTI as shown by the appearance of trypsin inhibitory activity. This activity could be released with an osmotic shock, demonstrating that BPTI accumulated in the periplasmic space. The expression level was too low to visualize the protein by coomassie-staining following gel-electrophoretic fractionation of total cellular extracts. From the activity measurements it could be calculated that the level of BPTI protein amounted to about 1 mg per liter of culture ($OD_{600nm}=\pm 4$). The production level reported here is comparable to that found by others using similar expression systems. Marks et al., J. Biol.

Chem., 261: 7115–7118 (1986) and Goldenberg et al., Biochemistry, 27: 2481–2489 (1988). Following purification (see below), the recombinant BPTI was subjected to N-terminal sequencing. The result indicates that the phoA-BPTI precursor undergoes correct processing.

EXAMPLE 2

Construction of the Genes Coding for BPTI-Derived Molecules by Site Directed Mutagenesis General procedures The inhibitors of this invention can be obtained by site directed mutagenesis of the wild type or a mutant form of the BPTI gene harbored in the pMa/c5-19 vectors. A typical protocol for site directed mutagenesis includes the following 6 steps.

1. Preparation of single-stranded DNA.

An overnight culture of WK6 cells harboring pMa5-PI, pMc5-PI or an appropriate derivative (grown at 37° C. in LB-medium supplemented with 100 µg/ml ampicillin or 25µg/ml chloramphenicol) was diluted 1:50 in fresh medium without antibiotic. Cells were grown to a density of about $2\times10^8$/ml and infected with helper phage M13KO7 (Vieira et al., Methods in Enzymology, 153: 3–11 (1987)) at a multiplicity of infection of 20. After a 5 to 16 hour incubation period, viral and pseudo-viral particles were recovered from the supernatant and the single-stranded DNA extracted essentially as described in Sambrook et al., *Molecular Cloning-A Laboratory Manual*, Cold Spring Harbor Laboratory Press, p. 4.29 (1989). The yield (typically 1–4 µg/ml culture) was determined by UV-spectroscopy ($\epsilon_{260nm}=2.86\times 10^{-2}$ cm$^2$/µg).

2. Preparation of DNA-fragment.

pMc5-PI or pMa5-PI plasmid DNA was digested to completion with the restriction enzymes SacII and SphI (both restriction sites are unique and are indicated in FIG. 4). The large fragment was recovered from low-melting-temperature agarose gel essentially as described in Weislander, L., Anal. Biochem., 98: 305–309 (1979). The yield of fragment was quantitated on an ethidium bromide stained agarose gel by comparison of the band intensity with known amounts of DNA.

3. Construction of gapped-duplex DNA (gdDNA).

The gdDNA was obtained by denaturation/renaturation of the large gel-purified SacII/SphI fragment described in step 2 above, and the single-stranded form of the complementary vector, from step 1 above. A 35 µl aqueous mixture (containing less than 2 mM salt) of fragment (0.1 pmole) and single-stranded DNA (0.5 pmole) was incubated at 70° C. for 5 minutes; then 5 µl of 1.5M KCl/100 mM Tris-HCl pH7.5, also brought to 70° C. was added, after which the mixture was allowed to cool to room temperature. Formation of gdDNA was monitored by electrophoresis of an aliquot of the hybridization mixture on agarose gel. The mobility of the gdDNA was indistinguishable from that of relaxed fully double-stranded pMa5-PI.

4. Annealing of the mutagenic oligonucleotide and gap filling/sealing reaction.

The intended amino acid substitutions were introduced by means of synthetic oligonucleotides.

The oligonucleotides were enzymatically phosphorylated and purified by preparative gel electrophoresis. Wu et al., *Oligonucleotide Synthesis-a Practical Approach*, IRL Press, Oxford and Washington DC, pp. 135–151 (Edit. Gait, M. J. 1984).

Ten picomoles of oligonucleotide(s) was added to 8, µl hybridization mixture containing the gdDNA. This mixture was heated to 65° C. for 5 minutes, and then allowed to cool to room temperature. Four µl 10× fill-in buffer (625 mM KCl, 275 mM Tris-HCl, 150 mM MgCl$_2$, 20 mM DTT, 0.5 mM ATP and 0.25 mM of each of the four dNTP's, pH7.5), water to give a final volume of 40 µl, 1 unit DNA polymerase I (Klenow fragment), and 5 units T4 DNA ligase were added. The mixture was incubated at room temperature for 45 minutes.

5. Transformation and segregation.

An aliquot of the polymerase/ligase reaction mixture (5 µl) was used to transform strain WK6mutS. Zell et al., The EMBO Journal, 6: 1809–1815 (1987). An aliquot (1/10) of the transformation mixture was spread on selective medium (25 µg/ml chloramphenicol or 100 µg/ml ampicillin) to determine the transformation efficiency; usually between 100 and 1000 transformants were obtained. The remainder of the transformation mixture was used to inoculate 10 ml of LB medium supplemented with 25 µg/ml chloramphenicol or 100 µg/ml ampicillin. After overnight growth, plasmid DNA was isolated and used to transform the su strain WK6 (Zell et al., supra), again selecting for the appropriate antibiotic resistance.

6. Identification of the intended mutant.

Single-stranded DNA (prepared as described in step 1) of a few randomly picked clones was sequenced. Sequence determination of the entire mutant coding region was carried out according to the dideoxy chain termination method of Tabor and Richardson, U.S. Pat. No. 4,994,372, using T7 DNA polymerase and a single primer which anneals to vector sequences immediately downstream of the BPTI coding region (see FIG. 2).

Construction of pMc5PI82c5 Coding for Inhibitor 82c5

Some of the inhibitors of this invention were obtained after several rounds of mutagenesis, interrupted by periods during which intermediate constructions were expressed, and the encoded protein purified and analyzed. These same mutations can be introduced in a smaller number of rounds or a different sequential order, using a different parent gene and different oligonucleotides. The examples given below are therefore not meant to be limiting, but merely illustrate the protein engineering cycle. Some of the vectors used as intermediates also code for factor VIIa-TF inhibitors of this invention. Below is a table showing construction of the 82c5 mutant using the oligonucleotides, single-stranded DNA, and vectors shown.

| mutations in BPTI | inhibitor encoding vector | single stranded DNA | SacII/SphI fragment | mutagenic oligo-nucleotide* |
|---|---|---|---|---|
| 1Ala 11Asp 15Arg 17Ile 19Lys 39Phe 46Glu* (SEQ ID NO:116) | pMa5PI82c5 | pMc5PI80c1 | pMa5PI | Pst313 |
| 1Ala 11Asp 17Ile 19Lys 39Phe 46Glu* (SEQ ID NO:117) | pMc5PI80c1 | constructed by litigation of AlwNI/Sty fragments (purified from low-melting temperature agarose gel) of pMc5PI14c5 and pMcPI78c6 | | |
| 1Ala 11Asp 17Ile 19Lys (SEQ ID NO:118) | pMc5PI14c5 | pMa5PI | pMc5PI | Pst229 |
| 1Ala 15Arg 17Tyr 19Thr 39Phe 46Glu* (SEQ ID NO:119) | pMcPI78c6 | pMa5PI56c1 | pMc5PI | Pst212 |
| 1Ala 15Arg 17Tyr 19Thr 39Phe* (SEQ ID NO:120) | pMa5PI56c1 | pMcPI51c3 | pMa5PI | Pst306 |
| 1Ala 15Arg 17Tyr 19Thr (SEQ ID NO:121) | pMcPI51c3 | pMa5PI31c5 | pMc5PI | Pst301 |
| +7bp deletion +A to T replacement[a] 1Ala 15Arg 17Tyr 19Thr (SEQ ID NO:122) | pMa5PI31c5 | pMc5PI3c4 | pMa5PI | Pst268 |
| 1Ala 13Ile 15Arg 17Tyr 19Thr (SEQ ID NO:123) | pMc5PI3c4 | pMa5PI | pMc5PI | Pst210 |

*Indicates that the mutant-BPTI is a factor VIIa-TF inhibitor of this invention.
[a]This vector does not code for a functional mutant-BPTI. The 7 bp deletion removes codon 39 as well as some adjacent bases. This, together with the A to T replacement, creates a unique AflII restriction site. AflII-digestion of the plasmid DNA isolated from the WK6mutS transformants prior to transformation of WK6 (step 5, above) effectively eliminates all the non-mutant progeny when restoring the coding region (construction of pMaPI56c1 and pMaPI52c19).

Construction of pMa5PI95c12 Coding for Inhibitor 95c12

Below is a table showing construction of the 95c12 mutant using the oligonucteotide, single-stranded DNA, and vectors shown.

| mutations in BPTI | inhibitor encoding vector | single stranded DNA | SacII/SphI fragment | mutagenic oligo-nucleotide |
|---|---|---|---|---|
| 1Ala 11Glu 15Arg 17Tyr 19Thr 39Tyr 46Glu* (SEQ ID NO:124) | pMa5PI95c12 | pMc5P179c4 | pMa5PI | Pst237 |
| 1Ala 15Arg 17Tyr 19Thr 39Tyr 46Glu* (SEQ ID NO:125) | pMc5PI79c4 | pMa5PI52c19 | pMc5PI | Pst212 |
| 1Ala 15Arg 17Tyr 19Thr 39Tyr*[b] (SEQ ID NO: 126) | pMa5PIS2c19 | pMcPI51c3 | pMa5PI | Pst302 |

[b]The degenerate oligonucleotide Pst302 was designed for introduction of the following codons: AAG, Lys; AAT, Asn; GAG, Glu; GAT, Asp; CAG, Gln; CAT, His; TAT, Tyr; and TAG, amber stop codon.
*Indicates that the mutant-BPTI is a factor VIIa-TF inhibitor of this invention.

Mutagenic Oligonucleotides

The sequences of the mutagenic oligonucleotides used in the construction of the vectors listed above are shown in the following table:

Pst313  GCTTAATAAT AGCCCGGCAG GGGC
        (SEQ ID NO:127)
Pst229  GTAGAAGTAG CGCTTAATAA TAGCCTTGCA GGGGCCGTCA
        TACGGTGG
        (SEQ ID NO:128)

-continued

| | | |
|---|---|---|
| Pst212 | CCTCGGCCGA TTCGAAATTG TTAC<br>(SEQ ID NO:129) | |
| Pst306 | GTTACGCTTA GCAAAGCAGC CACCATATAC<br>(SEQ ID NO:130) | |
| Pst301 | CTTGAAATTG TTACGCTTAA.GCCACCATAT ACAAAG<br>(SEQ ID NO:131) | |
| Pst268 | GCCCGGCATG GGCCGGTATA CGG<br>(SEQ ID NO:132) | |
| Pst210 | GAAGTAGCGG GTAATATAAG CCCGGCATAT GCCGGTATACGG<br>(SEQ ID NO:133) | |
| Pst237 | GCAGGGGCCC TCATACGGTG G<br>(SEQ ID NO:134) | |
| Pst302 | GTTACGCTTA GCMTNGCAGC CACCATATAC<br>(SEQ ID NO:135)<br>M = A or C; N = A,G,C or T | |

EXAMPLE 3

Purification of Recombinant BPTI-Derived Inhibitors from E. coli

E. coli cells were grown at 37° C. in baffled flasks in 250 ml LB medium containing chloramphenicol or ampicillin (as required by the type of vector involved, pMa5 requires ampicillin and pMc5 requires chloramphenicol). The cells were induced after 3 hours by addition of 0.1 mM IPTG and grown overnight. Lysis of E. coli cells was as described by Marks, C. B. et al., J. Biol. Chem. 261: 7115–7118 (1986). About 1 g of wet cells were suspended in 1.5 ml 40 mM TRIS buffer, pH 8, containing 20% sucrose and 50 mM EDTA, 2.5 mg of lysozyme was added, followed by 1.15 ml of 0.1% Triton X-100 and 0.3 ml NaCl (5M). After 15 minutes at room temperature 2.5 ml of 200 mM TEA buffer pH 7.8 was added followed by 0.15 ml $CaCl_2$ (1M) and 0.1 ml $MgCl_2$ (1M) and 10 μg DNAseI. The suspension was stirred for 20 minutes at 25° C. The majority of protein was precipitated by addition of 2% trichloroacetic acid (TCA) and removed by centrifugation. The TCA supernatant was neutralized by addition of NaOH for further purification.

One particular purification procedure consists of the following steps:

1. The TCA supernatant was adjusted to pH 4.0 and to a conductivity below 5 mS/cm with glacial acetic acid and MilliQ (Reagent Grade) water, respectively. The diluted TCA supernatant was filtered.
2. Cation exchange chromatography on S-Sepharose Fast Flow (10×100 mm) equilibrated with 50 mM sodium acetate and eluted with a 40 ml linear gradient of 0 to 1M NaCl (flow rate 1 ml/min). The fractions containing factor VII-TF inhibitor (determined using the amidolytic assay described in Example 7) Were collected and pooled.
3. Pooled fractions were injected on an Vydac Reverse Phase C18 column and eluted with a 20 min gradient of 10% to 45% acetonitrile in 0.1% TFA (1 ml/min).
4. Lyophilisation.

Another purification procedure comprises the following steps:

1. Affinity chromatography on trypsin-Sepharose, equilibrated with 100 mM TEA pH 7.8, 300 mM NaCl, washed with 5 column volumes of 100 mM TEA pH 7.8, 300 mM NaCl, 10 mM TEA pH 7.8, 50 mM NaCl and eluted with 20 mM HCl, 50 mM NaCl pH 1.8.
2. Cation exchange chromatography on Mono-S using a linear gradient of 10 column volumes of 10 to 500 mM ammonium acetate pH 5.
3. Reverse phase chromatography on HPLC C4 column, elution with a 0 to 35 % gradient of isopropanol in 0.1% TFA.
4. Lyophilisation.

EXAMPLE 4

Enzymatic Assays for Trypsin, Factor Xa, Thrombin, Factor XIIa and plasmin amidolytic assays The following assays are useful to determine useful inhibitors of the invention, namely those with a low Factor VIIa-TF $K_i$, and preferably high relative $K_i$'s for other enzymes.

Briefly, the following were added to a 96-well microtiter plate well (see Table below): 50 μl TBSA (100 mM TRIS pH 7.4, 140 mM NaCl, 0.1% BSA); 50 μl inhibitor (various concentrations as required, diluted in TBSA); 50 μl protease (suitable concentration, diluted in TBSA). The plate was incubated at room temperature for 30 minutes or for 2 hours (Factor Xa); and 50 μl chromogenic substrate added (as required, diluted in water). The initial rate was measured at 405–650 nM during 10–30 minutes at room temperature.

| | Assay Concentration of: | | |
|---|---|---|---|
| Protease Assayed | Protease (nM) | Substrate (mM) | Substrate Used |
| Factor XIIa | 1 | 0.2 | D-hexhydroTyrosine-Gly-Arg-pNA diacetate. |
| Factor VIIa | 2.5 | 0.1 | D-Ile-Pro-Arg-pNAdihydrochloride. |
| Factor Xa | 0.25–0.50 | 0.25 | N-α-Cbo-D-Arg-Gly-Arg-pNA |

-continued

| Protease Assayed | Assay Concentration of: | | Substrate Used |
|---|---|---|---|
| | Protease (nM) | Substrate (mM) | |
| thrombin | 1 | 0.06 | dihydrochloride. D-Phe-L-Pipecolyl-Arg-pNA dihydrochloride. |
| plasmin | 1 | 0.50 | L-pyroglutamyl-Pro-Arg-pNA hydrochloride; |
| activated protein C | 1 | 0.4 | γ-Cbo-D-Lys-Pro-Arg-pNA diacetate. |
| tissue plasminogen activator | 1 | 1 | O-(methylsulfonyl)-D-hexa-hydro-plasminogen tyrosyl-Gly-Arg-pNA acetate. |
| trypsin | 1 | 0.25 | N-Bz-Ile-(γ-OR)-Glu-Gly-Arg-pNA hydrochloride, wherein R=H (50%) and R=CH₃ (50%). |

"pNA" refers to para-nitrophenylanilide
"Cbo" refers to benzyloxycarbonyl
"Bz" refers to benzoyl To determine the inhibition constants, the initial rate ($v_i$) was measured at various inhibitor ($[I_t]$) and substrate concentrations, and the apparent inhibition constant ($K_i$) was determined by fitting the data obtained at each substrate concentration with the following equation:

$$v_i/v_o = \{([E_t]-[I_t]-K_i^*) + [([I_t]+K_i^*-[E_t]^2+4K_i^*[E_t]]^{1/2}\}/2[E_t]$$

where $v_o$ is the uninhibited initial rate and $[E_t]$ is the total enzyme concentration. Extrapolation of Ki* values to zero substrate concentrations yields a value for the real inhibition constant.

Amidolytic assay for Factor VIIa

Equal volumes of Factor VIIa (10 nM in TBS containing 0.8% BSA and 20 mM CaCl₂) and tissue Factor (40 nM in TBS containing 0.03% Triton X-100) were combined and incubated for 30 minutes at room temperature. 100 μl of the VIIa/TF complex was mixed with 50 μl of inhibitor and incubated for 30 minutes. The reaction was started by addition of substrate, typically 0.4 mM of S-2288 (D-Ile-Pro-Arg-pNA), and the initial rate of product formation was determined. The inhibition constant ($K_i$) is determined from the above equation.

Amidolytic Assay for Activated Protein C

Reconstituted lyophilized human normal plasma is used as a source of protein C. Protein C activating enzyme (Kabi) is added to diluted plasma to give a concentration of approximately 5 nM activated protein C. 50 μl of activated protein C solution is combined with 100 μl TBSA or inhibitor diluted in TBSA and incubated for 30 minutes at 37° C. 50 μl of 2 mM S-2366 (<Glu-Pro-Arg-pNA) is added and the initial rate of product formation is measured at 405 nm in a microliter plate reader. The inhibition constant is determined from the following equation:

$$v_o/v_i = 1 + [I_t]/K_i$$

when the total inhibitor concentration ($[I_t]$) exceeds the total enzyme concentration. Typical inhibitor concentrations vary between 0.5 and 5 μM.

EXAMPLE 5

Inhibition Constants for Selected Factor VIIa-TF Inhibitors

Several mutant BPTI Factor VIIa-TF inhibitors were made by site directed mutagenesis using a method as described in Example 2 or obtained from random libraries such as described in Example 7. These mutant BPTI Factor VIIa-TF inhibitors were produced in E. coli and purified as described in Example 3. The enzymatic methods described in Example 4 were used to determine their inhibition constant for several serine proteases, including Factor VIIA-TF. The inhibition constant for Factor VIIa-TF of a selection of inhibitors is given below.

| Name | Amino acid substitutions in BPTI | $K_i$ (nM) |
|---|---|---|
| 20c4 | 1Ala 11Asp 17Ile 19Lys 39Glu 46Glu (SEQ ID NO:136) | 300 |
| 27c27 | 1Ala 11Glu 17Ile 19Lys 39Glu 46Glu (SEQ ID NO:137) | 480 |
| 63c2 | 1Ala 11Asp 15Arg 17Ile 19Lys 39Glu 46Glu (SEQ ID NO:138) | 37 |
| 72c2 | 1Ala 11Asp 15Arg 17Ile 19Lys 34Asp 39Leu (SEQ ID NO:139) | 200 |
| 78c6 | 1Ala 15Arg 17Tyr 19Thr 39Phe 46Glu (SEQ ID NO:140) | 65 |
| 80c1 | 1Ala 11Asp 17Ile 19Lys 39Phe 46Glu (SEQ ID NO:141) | 30 |
| 81c1 | 1Ala 11Asp 17Ile 19Lys 39Tyr 46Glu (SEQ ID NO:142) | 20 |
| 82c5 | 1Ala 11Asp 15Arg 17Ile 19Lys 39Phe 46Glu (SEQ ID NO:143) | 8 |
| 83c6 | 1Ala 11Asp 15Arg 17Ile 19Lys 39Tyr 46Glu (SEQ ID NO:144) | 20 |
| 85c1 | 1Ala 15Arg 17Ile 19Lys 39Phe 46Glu (SEQ ID NO:145) | 40 |
| 88c1 | 1Ala 15Arg 17Tyr 19Thr 39Tyr 46Tyr (SEQ ID NO:146) | 80 |
| 95c12 | 1Ala 11Glu 15Arg 17Tyr 19Thr 39Tyr 46Glu (SEQ ID NO:147) | 10 |
| 98c5 | 1Ala 15Arg 17Met 18His 19Phe 39Phe 46Glu (SEQ ID NO:148) | 14 |
| 5110 | 11Asp 15Arg 17Leu 18His 19Gln 34Thr 46Glu (SEQ ID NO:149) | 4.2 |
| 5115 | 11Asp 15Arg 17Leu 18His 19Leu 34Tyr 39Leu 46Glu (SEQ ID NO:150) | 0.5 |
| 5118 | 11Glu 13Tyr 15Arg 17Leu 18His 34Tyr 39His 46Glu (SEQ ID NO:151) | 0.9 |

| Name | Amino acid substitutions in BPTI | $K_i$ (nM) |
|---|---|---|
| 5137 | 11Asp 15Arg 17Leu 18His 19Pro 34Trp 39Tyr 46Glu (SEQ ID NO:152) | 0.6 |
| 5142 | 11Asp 15Arg 17Leu 18His 19Pro 34Trp 39Leu 46Glu (SEQ ID NO:153) | 1.5 |
| 5145 | 11Asp 15Arg 17Leu 18His 19His 34Tyr 46Glu (SEQ ID NO:154) | 4.6 |
| 5168 | 11Ser 13Leu 15Arg 17Leu 18His 19Lys 34Tyr 39Phe 46Glu (SEQ ID NO:155) | 2.3 |
| 5184 | 11Glu 13Leu 15Arg 17Leu 18His 19Lys 34Tyr 39Phe 46Glu (SEQ ID NO:156) | 2 |
| 6115 | 9Ala 11Asp 15Arg 17Leu 18His 19Gln 22Leu 39Phe 46Glu (SEQ ID NO:157) | 0.4 |

EXAMPLE 6

Selectivity of BPTI-Derived Factor VIIa-TF Inhibitors

The selectivity of the described inhibitors of Factor VIIa-TF is an important feature of these compounds with respect to their ability to control pathogenic thrombosis formation with minimal effects of the hemostatic potential of the treated patient. This will result in a reduction in the incidence of associated bleeding complications during therapy. The importance of specifically inhibiting Factor VIIa-TF versus thrombin and Factor Xa is clear when one considers the amplified nature of the coagulation cascade. Therefore, dosage of a selective Factor VIIa-TF inhibitor required to achieve a clinically relevant antithrombotic effect will be considerably less than a comparable thrombin inhibitor of equal potency or an inhibitor of Factor Xa. Overall, the greater the selectivity of an inhibitor towards individual enzymes in the coagulation cascade, the less probability exists that unwanted side effects will occur during therapy.

The Factor VIIa-TF inhibitor called 82c5 contains the following substitutions in BPTI:

1Ala 11Asp 15Arg 17Ile 19Lys 39Phe 46Glu. Inhibitor 82c5 inhibits Factor VIIa-TF with an inhibition constant in the low nanomolar range. It is a slow tight binding inhibitor of Factor VIIA-TF with quasi irreversible binding under physiological conditions.

The selectivity of 82c5 for factor VIIA-TF versus Factor Xa is about 100 fold. Thrombin and activated protein C are not inhibited by 82c5 at concentrations around its Ki value for factor VIIa-TF.

82c5 is, as BPTI, a potent trypsin inhibitor. This is not unexpected since trypsin is not a specific protease; its inhibition profile is largely determined by the P1 residue (Arg or Lys) with a great deal of variability tolerated in the surrounding residues.

Plasmin plays a crucial role during thrombolysis, since it degrades the fibrin clot. However plasmin is also believed to be responsible for bleeding problems often encountered during thrombolytic therapy. Bleeding can be reduced by administration of Aprotinin (BPTI) which is a very efficient plasmin inhibitor. Compared to BPTI the affinity of 82c5 for plasmin is reduced about 1000 fold, with an inhibition constant around 100 nM. Other BPTI mutants of this invention have substantially reduced plasmin activity while retaining significant Factor VIIa-TF inhibition.

EXAMPLE 7

Construction of phage libraries Basic construction

To allow for selection of factor VIIa-TF inhibitors by panning procedures, the mutant BPTI gene was fused to the P-III coat protein of a filamentous *E. coli* phage such as fd-tet. Zacher III et al., Gene 9: 127–140 (1980). FIG. 5 shows the DNA sequences of various oligonucleotides used for construction of pMa5-PI.

The Kunkel method was used to engineer the Gene III variant (III) by oligonucleotide directed mutagenesis. Kunkel, Proc. Natl. Acad. Sci. USA, 82: 488–492 (1985).

```
secretional signal           BspMII        KasI         mature P-III          (III)
CAC TCC GCT CCG GAC ACT AGT GGT GGC GCC GCT GAA (SEQ ID NO:158)

His  Ser  Ala  Pro  Asp  (SEQ ID NO:159) Gly  Gly  Ala  Ala  Glu  (SEQ ID NO:160)
     BPTI  1    2    3                   56   57   58
```

In this method, the BPTI gene (from the pMa/c5-PI vectors, described above) or an appropriate BPTI-derived gene was introduced into construction III, above, as a BspMII-KasI fragment.

Construction of the Library Called 2L

To allow random mutagenesis of the amino acid residues 15 through 20 of BPTI, a new vector, pMc5-PI28c5, was constructed containing a BPTI-derived gene which carries a PstI and ApaI site as well as a frame shift. The 28c5 mutant gene was constructed making use of the following oligonucleotides:

| | |
|---|---|
| Pst238: | GTTACGCTTT GCCCTGCAGC CACC (SEQ ID NO:161) |
| Pst239: | GCCTTGCAGG GGCCCUGTAT ACGGTGG (SEQ ID NO:162) |

The phage having the 28c5 mutant gene is called fd-28c5. The frame shift was corrected when the mutagenic oligonucleotides were inserted into fd-28c5. In this way, a large background of wild type BPTI-expressing phages is avoided in cases of incomplete insertion of the oligonucleotides.

The mutagenic oligonucleotide (Pst240) inserted into fd-28c5 contains the degenerate coding sequence shown in (IV), where R is an equimolar mixture of A and G; N is either of G, A, T and C; and K is either G and T.

Pst240:  TAT ACC GGG CCC TGC ARG NNK NNK NNK NNK NNK TAC
         TTC TAC AAC GCC AAG GCC GGA CTC TGT
                              (IV)
(SEQ ID NO:163)

This allows replacement of Lys15 with either an Arg or Lys; and of Ala16, Arg17, Ile18, Ile 19, Arg20 with any of the twenty natural amino acids.

The mutagenic oligonucleotide (PST240), and a second overlapping oligonucleotide (PST241, V), were converted into a double stranded DNA fragment using Taq-polymerase.

The new vector pMa5-PI89 contains the following BPTI derived sequence.

Transfer of the BspMII-KasI fragment in this vector to the phage genome (engineered gene variant III as described on pages 13–14) resulted in fd-89. The sequence of VI does not code for a functional protein because of the presence of a frame shift. The sequence between nucloetides 35 and 65

Pst241:  CTTTGCCCTG CAGCCACCAT ATACAAAGGT CTGACAGAGT
         CCGGCCTTGG CGTTGTAGAA GTA
                              (V)
(SEQ ID NO:164)

Following digestion with ApaI and PstI, the mutagenic fragment was ligated to the large gel-purified ApaI-PstI fragment of fd-28c5 replicative form DNA. Ligated samples were used to electroporate WK6 E. coli cells. Transformants were selected on LB plates supplemented with 10 μg/mL tetracycline.

(a) Construction of the 3L-library

This library contains a number of fixed amino acid substitutions in BPTI: Pro13Ile, Lys15Arg, Arg39Leu and Lys46Glu. In addition, at positions 16 to 19 all possible amino acid residues can occur. A new vector, pMa5-PI89, was constructed by oligonucleotide mediated mutagenesis of pMc5-PI4c2 using Pst344.

provides restriction sites (BbsI) for easy insertion of the mutagenic oligonucleotides and counterselection against parental phages (FspI). Construction of the library involved the replacement of the small BbsI fragement of fd-89 by the mutagenic oligonucleotide Pst345. This cloning brings the two translated regions shown in (VI) in frame. The mutagenic oligonucleotide contains a degenerate coding sequence, where N is either of G, A, T and C and K is either G and T.

Pst345 was hybridized to two "half-site" oligonucleotides (Pst346 and Pst347 see below) to form cohesive termini complementary to the BbsI sites shown in (VI). Because cleavage of the two BbsI sites creates non-complementary Pst344:  GGTCTGACAG AGACCGGCCT TGGCGTFGTG TCTTCGGTTA
         ATTTAAATGC GCAGAAGACC CGGTATACGG TGGCTCGAG
(SEQ ID NO: 165)

```
                                            BbsI
BspMII      10          XhoI     20        ¦ 30              40
  ¦         *             ¦       *        ¦  *               *
GCT CCG GAC TTC TGT CTC GAG CCA CCG TAT ACC GG GTC TTC
Ala Pro Asp Phe Cys Leu Glu Pro Pro Tyr Thr Gly (SEQ ID NO:167)

FspI        50                   60      BbsI 70              80
  ¦         *                     *        ¦   *               *
TGC GCA TTT AAA TTA ACC GAA GAC AC  AAC GCC AAG GCC GGA
                                    Asn Ala Lys Ala Gly 90                      100              110             120
 *                       *                *               *
CTC TGT CAG ACC TTT GTA TAT GGT GGC TGC CTT GCA AAG CGT
Leu Cys Gln Thr Phe Val Tyr Gly Gly Cys Leu Ala Lys Arg

130         EagI  140            150             160
          *           ¦    *              *               *
AAC AAT TTC GAA TCG GCC GAG GAC TGC ATG CGT ACC TGT GGT
Asn Asn Phe Glu Ser Ala Glu Asp Cys Met Arg Thr Cys Gly

KasI 170
  ¦    *
GGC GCC  (SEQ ID NO:166)
Gly Ala  (SEQ ID NO:168)
``` cohesive ends insertion of the mutagenic fragment in the proper orientation is ensured. The conditions used to insert the mutagenic oligonucleotides were essentially as described by Cwirla et al., Proc. Natl. Acad. Sci. USA: 87, 6378–6382, 1990. The ligated DNA was transformed by electroporation into *E- coli* WK62 (a spontaneously arisen F derivative of WK6). Transformants were plated on LB agar containing tetracycline.

| Pst345: | TACCGGCATC TGCCGCNNKN NKNNKNNKCG CTACTTCTAC (SEQ ID NO:169) |
|---|---|
| Pst346: | GCGGCAGATG CC (SEQ ID NO:170) |
| Pst347: | CGTTGTAGAA GTAGCG (SEQ ID NO:111) |

Construction of the 5L-library
The intended library contains the following substitutions:

| position | 11:Xxx (=all possible residues) |
|---|---|
| | 13:Xxx |
| | 15:Arg |
| | 17: Leu/Ile |
| | 18: His |
| | 19: Lys/Asn/Thr/Met/Ile/Gln/His/Pro/Leu |
| | 34: Xxx |
| | 39: Xxx |
| | 46: Glu |

The mutagenic oligonucleotides, Pst374 and Pst375, contain degenerate sequences indicated with the following one letter code:

N is either of G, A, T and C

H is either of A, T and C

D is either of A, T and G

S is either of G and C

M is either of A and C

K is either of G and T

| Pst374: | TCGAGCCACC GTATNNSGGT NNSTGCCGTG CTMTTCATMH SCGCTACTTC TACAACGCCA AGGCCGGTCT CTGTCAGACC TTTNNSTATG GTGGCTGCNN SGCAAAGCGT AACAATTTCG ATC (SEQ ID NO: 172) |
|---|---|
| Pst375: | GGCCGATTCG AAATTGTTAC GCTTTGCSNN GCAGCCACCA TASNNAAAGG TCTGACAGAG ACCGGCCTTG GCGTTGTAGA AGTAGCGSDK ATGAAKAGCA CGGCASNNAC CSNNATACGG TGGC (SEQ ID NO:173) |

Annealing of the oligonucleotides Pst374 and Pst375 yields a double stranded DNA fragment having XhoI and EagI cohesive termini. This fragment was ligated to the large gel-purified XhoI-EagI fragment of fd-89 (VI). The ligated DNA was transformed by electroporation in *E. coli* WK62 (a spontaneously arisen F derivative of WK6). Transformants were plated on LB agar containing tetracycline.

EXAMPLE 8

Panning of phages expressing on their surface factor VIIa-TF inhibitors

Figure 6:
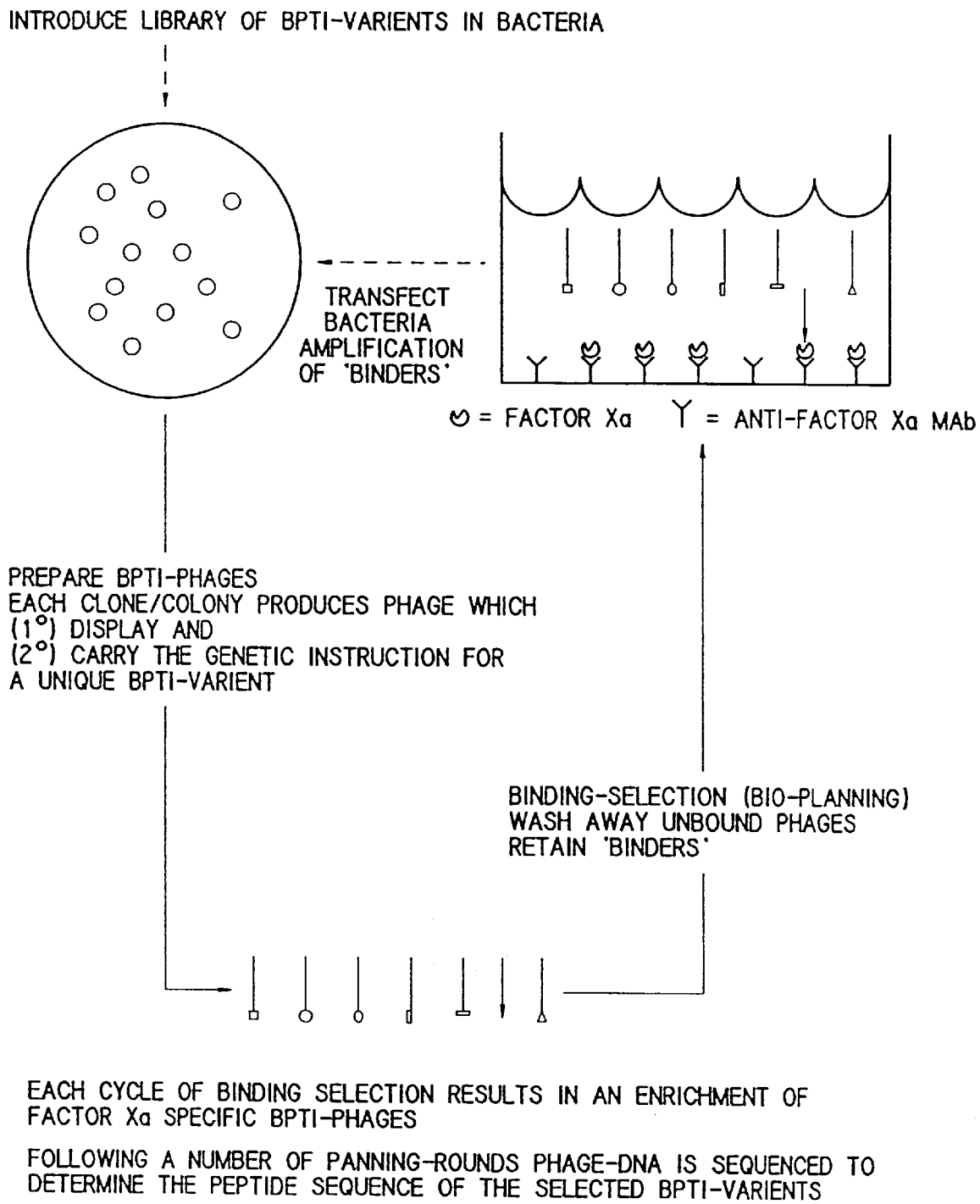
FIG. 6 is a diagram representing a method for isolating phages displaying a potent Factor VIIa inhibitor of this invention.

Referring to FIG. 6, in one particular panning protocol a suspension of phages expressing the mutant BPTI molecules on their surface was incubated with factor VIIa-TF. Phages bound to factor VIIa-TF were separated from the others by means of a non-neutralizing anti-VIIa monoclonal antibody coupled to agarose. The following procedure was used for panning of the 2L library.

Mutant BPTI-phages were isolated by scraping the tetracycline resistant transformants from the plates. The cell suspension (LB medium) was cleared twice by centrifugation and the phages were recovered from the supernatant by PEG precipitation. The phage pellet was resuspended in TBS (TRIS buffered saline pH 7.4). About $10^{10}$ infectious particles (0.5 ml) were mixed with 0.5 ml containing 200 nM factor VIIa (NOVO), 400 nM Tissue Factor (Corvas), 10 mM $CaCl_2$, 0.5% Tween20 in TBS. The suspension was incubated at room temperature during 1 h. A 0.1 ml suspension of 0.18 mg of anti-VIIa-Mab immobilized on CNBr-activated Sepharose C 14B was added and further incubated at room temperature for 1 h. The gel was removed by centrifugation and washed 10 times with 1 ml TBS containing 0.5% Tween20 and 5mM $CaCl_2$. Bound phages were eluted with 2 times 0.5 ml of 0.1N HCl/glycine pH 2 containing 0.15M NaCl, 0.05% BSA, 0.5% Tween 20 and 5 mM $CaCl_2$. Eluted phages, neutralized by addition of 1M TRIS (pH 8), were amplified by infecting strain WK6 and plating for tetracycline resistant colonies. Cwirla, S. E., et al., Proc. Natl. Acad. Sci. USA, 87: 6378–6382 (1990). Phages were recovered as described above and the panning-amplification process repeated twice as described above except that 25 nM and 1 nM factor VIIa was used during the incubation. After two and three rounds of panning the phage DNA was purified and sequenced using standard techniques. Sambrook et al. in Molecular Cloning-a Laboratory Manual, Cold Spring Harbor Laboratory Press, 1989, p. 4.29. Tabor and Richardson, U.S. Pat. No. 4,994,372. Selected phage clones were tested for inhibition of factor VIIa-TF amidolytic activity essentially as described in Example 4.

In another preferred panning protocol the phages were incubated with biotinylated factor VIIa in presence of an excess tissue factor (TBS containing 0.5% Tween20 and 5mM $CaCl_2$). Phages bound to factor VIIa-TF were separated by binding of the biotinylated factor VIIa to streptavidin coated magnetizable beads (DynaI) and eluted at low pH as above. Factor VIIa was biotinylated using Biotine-XX-NHS essentially according to the instructions of the manufacturer (Calbiochem). This procedure was used for panning of the 3L library in three rounds using 10 nM Factor VIIa. Biotinylated factor VIIa was also used for panning of the 5L library in three rounds using 10 nM factor VIIa in one experiments and two rounds of 10 nM followed by one round of 1 nM factor VIIa in a second experiment.

EXAMPLE 9

Identification and Purification of a non-neutralizing Monoclonal Antibody Directed to Factor VIIa Preparation of hybridomas and identification of desired monoclonal antibodies is done using standard techniques as described for example in Harlow, E. et al., *Antibodies: A Laboratory Manual*, Cold Spring Harbor Laboratory (1988). These antibodies are useful in the method described above.

Female balb/c mice are immunized with purified human Factor VIIa isolated from pooled human plasma. Complete Freund's adjuvant is used for primary immunization and incomplete Freund's adjuvant for booster immunization. Route of immunization is both intraperitoneal and subcutaneous. Three days prior to fusion mice receive an intravenous perfusion boost of purified Factor VIIa in saline. Spleens are removed and spleen cells are fused to the SP2/0 myeloma following standard hybridoma methods.

Screening is performed to identify hybridoma antibodies that react with Factor VIIa antigen without inhibition of the enzymatic activity of Factor VIIa. Briefly, 96 well polyvinyl chloride microtiter plates are passively coated with affinity-purified goat anti-mouse IgG (from commercial source, e.g., Sigma Chemical Company, St. Louis, Mo.). Antibody-coated plates are blocked with bovine albumin and culture supernatants (diluted at least 1:50) are bound to the plates. Plates are washed to remove unbound antibody and Factor VIIa added followed by incubation. Plates are washed to remove unbound Factor VIIa. Negative controls include hybridoma culture supernatant from a cell line secreting irrelevant monoclonal antibody, sterile culture medium and buffer.

The lack of inhibition of Factor VIIa-TF by the purified monoclonal antibody is confirmed using the chromogenic assay described in Example 4.

The monoclonal antibody is immobilized on CNBr-activated Sepharose CL4B (Pharmacia) according to the manufacturer's instructions, for use as described above. Prior to this immobilization, immunoglobulin IgG is purified from the ascites fluid of a mouse containing the mouse hybridoma cell line of interest using a Biorad Laboratories MAPS II system according to the manufacturer's instructions.

EXAMPLE 10

Construction of 82c5 Secretion Vectors and Expression in the Methylotrophic Yeast Pichia pastoris Alcohol oxidase, the first enzyme in the methanol utilization pathway of Pichia pastoris, can constitute as much as 30% of the soluble protein of the cell during growth on methanol. In contrast, when this yeast is grown in presence of an excess of repressible-carbon sources, such as glucose or glycerol, no alcohol oxidase is present. Several genes of the methanol utilization pathway have been cloned and characterized. Their methanol-inducible promoter regions have been sequenced and used to construct various expression vectors.

The Pichia strain GTS 115 (his4) and the *E. coli-Pichia* shuttle vectors pHILS1 and pHILD4 referred to hereafter are part of the Pichia yeast expression system licensed from the Phillips Petroleum Company.

All the yeast manipulations, including electroporation, screening of multicopy integrants, determination of the methanol utilization (Mut) phenotype and fermentation, were performed according to the procedures manual provided by the Phillips Petroleum Company.

Figure 7:
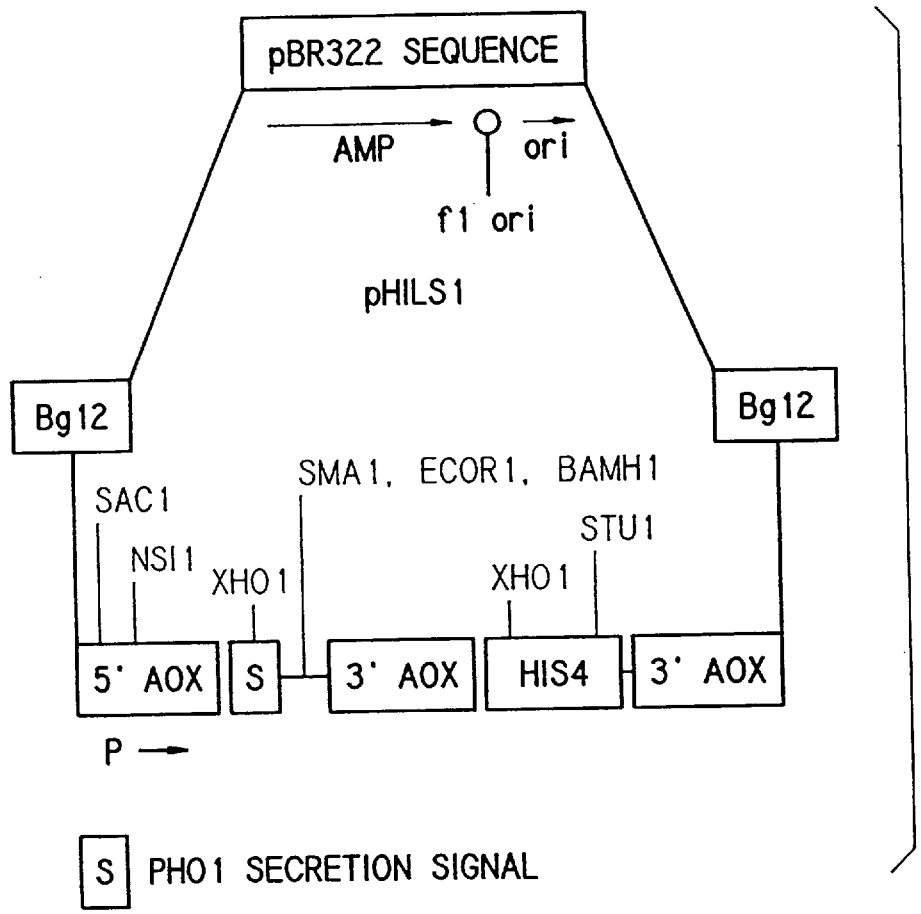
FIG. 7 is a diagrammatic representation of the pHILSl E. coli—P. pastoris shuttle vector. This plasmid contains a segment of the E. coli plasmid pBR322 which contains the ampicillin resistance gene (Amp) and the E.coli (ori) origin of replication. This portion also contains the fl-bacteriophage origin of replication (fl ori). The P. pastoris elements (AOX, PHO1, HIS4) are defined in example 10. Relevant restriction sites are also indicated (Bgl2, Sacl, Nsil, XhoI, Smal, EcoRI, BamHI, Xbal, Stul).

The pHILS1 plasmid (FIG. 7) contains the following *P. pastoris* elements:

1) 5' AOX1, about 1000 bp segment of the alcohol oxidase promotor fused to PHOL signal peptide, with XhoI, EcoRI, SmaI and BamHI cloning sites.

2) 3' AOX1, about 256 bp segment of the alcohol oxidase terminating sequence.

3) *P. pastoris* histidinol dehydrogenase gene, HIS4, contained on a 2.4 kb fragment to complement the defective his4 gene in the host GTS 115.

4) Region of 3' AOX1 DNA, which together with the 5' AOX1 region is necessary for site-directed integration.

In this vector, the ATG start codon of the PHOL secretion signal is located downstream of the AOX1 promotor exactly at the same position as the ATG of the AOX1 gene.

The junction between the PHO1 signal sequence and the 5' AOX1 and 3' AOX1 sequences are as follows:

5' AOX1   PHO1 SIGNAL SEQUENCE   XhoI

TTA TTC GAA ACG/ATG TTC TCT (SEQ ID NO:174).....GTC TTC GCT/CGA GAA

TTC CCC          Met Phe Ser....................Val Phe Ala

BamHI       3' AOX1

GGG ATC CTT/AGA CAT (SEQ ID NO:175).....

In order to facilitate further manipulations (cloning, site-directed mutagenesis) the small SacI-XbaI fragment of the pHILS1 vector, referred to hereafter as 'the expression cassette' was transferred on the pMc5-19 vector digested with SacI-XbaI, yielding pMc5-ppS1.

A SacII restriction site was introduced by site-directed mutagenesis after the PHO1 secretion signal to allow in frame fusion of heterologous gene to this signal. The generated sequence is as follow:

```
    5' AOX1  P HO1  SIGNAL SEQUENCE        SacII

TTA TTC GAA ACG/ATG TTC TCT  (SEQ ID NO:176)...GTC TTC GCCGC/GG GAA

TTC CCC         Met  Phe  Ser..................................Val  Phe  Ala

BamHI      3' AOX1

GGG ATC CTT/AGA CAT  (SEQ ID NO:177)
```

The resulting vector, pMc5-ppS5, digested with SalI and blunt ended with a Klenov treatment gives precise access to the last amino acid of the PHO1 signal.

Using standard manipulation technics, a pMc5-ppS5 derivative, pMc5-ppSP82c5 has been constructed. In this vector, the 82c5 encoding sequence, preceded by a synthetic pro-sequence (P), is fused in frame to the PHO1 secretion signal (S). The pro-sequence used is one of the two 19-aa pro-sequences designed by Clements et al., (1991. Gene 106:267–272) on the basis of the alpha-factor leader sequence and has the following amino acids composition:

Gln — Pro — Val — Ile — Ser — Thr — Thr — Val — Gly — SerAla — Ala —

— Glu — Gly — Ser — Leu — Asp — Lys — Arg  (SEQ ID NO:178)

The pro-sequence end with the alpha-factor KEX2 cleavage site (Lys-Arg).

The *P. pastoris* expression vector pHIL4-SP82c5 was constructed by reintroducing the expression cassette from pMc5-ppSP82c5 into the pHILD4 vector context, replacing the corresponding region of pHILD4. The latter vector contains, in addition to the other elements of pHILS1, a bacterial kanamycin resistance gene inserted between the HIS4 and 3'AOX1 regions. It can be used to screen for Pichia transformants with multiple copies of the expression cassette by screening for increased level of resistance to the antibiotic G418.

After transformation (electroporation method) of pHIL4-SP82c5 in the Pichia strain GTS115, His+ transformants were evaluated for 82c5 production in shake-flask after induction of the Paox promoter with methanol. Clones were found that directed the synthesis and secretion of 82c5, up to 90 mg/l, as shown by the appearance of trypsin inhibitory activity in the culture medium.

Following purification, the recombinant 82c5 was subjected to N-terminal sequencing. The results indicate that the PHO1 -pro-82c5 precursor was correctly processed.

EXAMPLE 11

Inhibition of Thrombin Generation in Human Plasma

The measurement of thrombin generation can be used to assess the potency of anti coagulants in human plasma. Béguin et al., 68 *Thromb. Haemost.*, 136–142, 1992.

Citrated human plasma was stored at −80° C. in aliquots of 1 ml. The plasma was defibrinated by addition of reptilase solution (20 μl to 1 ml of plasma). The reptilase solution was prepared according to the manufacture's instructions (Boerhinger Mannheim). After 10 minutes at 37° C. the clotted plasma was transferred to ice for 10 more minutes. The clot was then removed by winding it on a small plastic spatula.

To 240 μl of defibrinated plasma was added: 20 μl of Phospolipids (27 μM, mixture of 1,2 dioleoyl-sn-glycero-3-phosphoserine, 1,2-dioleoyl-sn-glycero-3-phosphocholine; 20/80, mol/mol), and 60 μl of inhibitors (5L15 or Hirudin) at the required concentrations (in 25 mM HEPES pH 7.5, 175 mM NaCl, 0.05% BSA). A control experiment was also run in the absence of 5L15 or Hirudin. Thrombin generation was triggered by addition of a sufficient amount (60 μl) of human recombinant tissue factor in $CaCl_2$ 0.1M to give a thrombin peak of approximately 250 nM in 2.5 minutes.

Every 30 seconds, 10 μl of plasma solution were transferred to a cuvette containing 490 μl of 50 mM Tris-HCl pH 7.35, 0.1M NaCl, 0.5 % BSA, 20mM EDTA and 200 μM substrate (S2238). After two minutes the reaction in the cuvette was stopped with 300 μl of citric acid 1M. The precise moment of sampling and stopping was directly recorded on a personal computer using push-button-equipped pipettes.

The thrombin concentration was determined by the measurement of the absorbance of the cuvettes at 405 and 500 nm on a double wavelength spectrophotometer.

Figure 8:
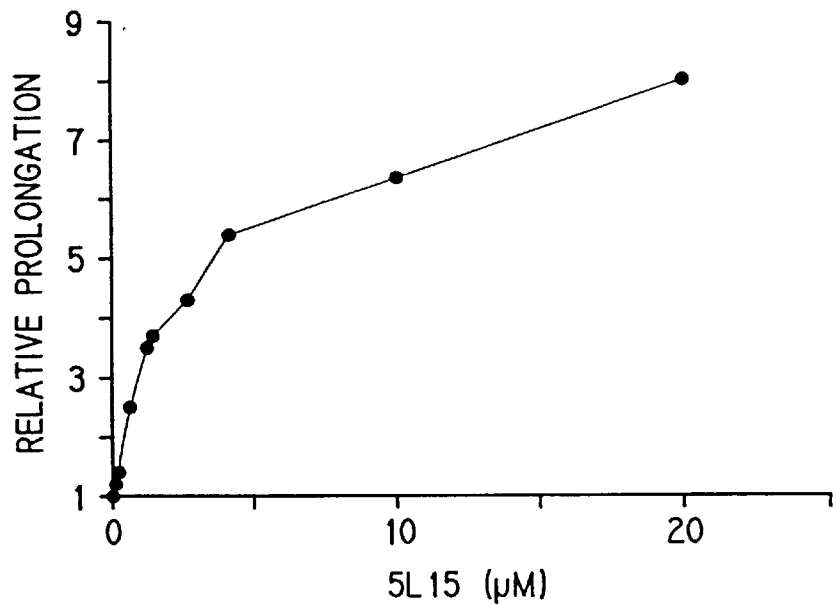
FIG. 8 is a diagram representing a dose response curve of 5L15 in human plasma obtained upon tissue factor activation. Relative prolongation is calculated as the ratio of the time of appearance of the maximum of active thrombin in the presence of 5L15 over the time of appearance of the maximum of active thrombin in the absence of inhibitor.
Figure 9:
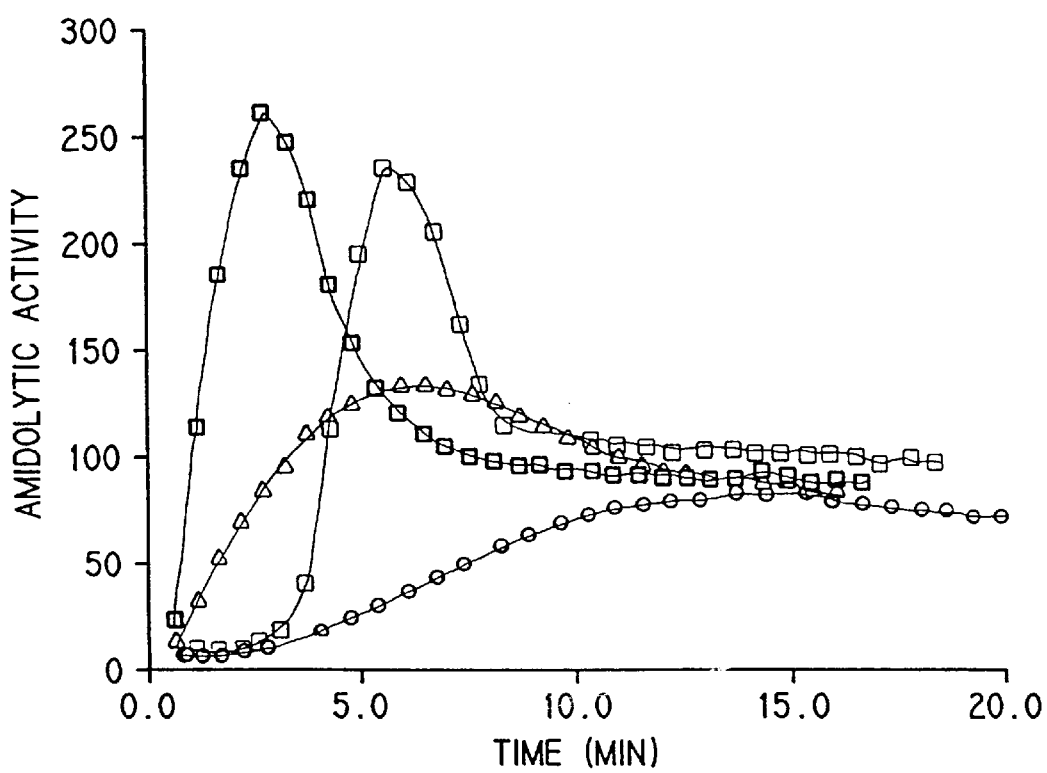
FIG. 9 is a diagram representing thrombin generation curves showing the effect of 5L15 and Hirudin in human plasma upon tissue factor activation. Open squares represent control (no anticoagulant); open triangles represent 5L15 (0.663 $\mu$M); open circles represent 5Ll5 (3.938 $\mu$M); and closed squares represent Hirudin (0.1 $\mu$M).

An example of the effect of anticoagulants in thrombin generation in human plasma is shown in FIG. 9, where 5L15 (0.663 and 3.938 μM) is compared to a well established thrombin inhibitor (Hirudin; 0.1 μM). From such thrombin generation curves, the potency of anticoagulants can be evaluated in measuring their effect on the prolongation time of appearance of the maximum thrombin generated. The dose dependence of this prolongation obtained with 5L15 is shown in FIG. 8.

Other embodiments are within the following claims.

SEQUENCE LISTING ( 1 ) GENERAL INFORMATION:

( i i i ) NUMBER OF SEQUENCES: 294

( 2 ) INFORMATION FOR SEQ ID NO: 1:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( x i ) SEQUENCE DESCRIPTION: SEQ ID NO: 1:

Arg Pro Asp Phe Cys Leu Glu Pro Pro Tyr Thr Gly Pro Cys Lys Ala
            5                        10                      15

Arg Ile Ile Arg Tyr Phe Tyr Asn Ala Lys Ala Gly Leu Cys Gln Thr
            20                      25                      30

Phe Val Tyr Gly Gly Cys Arg Ala Lys Arg Asn Asn Phe Lys Ser Ala
            35                      40                      45

Glu Asp Cys Met Arg Thr Cys Gly Gly Ala
    50                      55

( 2 ) INFORMATION FOR SEQ ID NO: 2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO: 2:

Gly Pro Cys Lys Ala Arg Ile Ile
            5

( 2 ) INFORMATION FOR SEQ ID NO: 3:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i x ) FEATURE:
        ( D ) OTHER INFORMATION: Xaa in position 7 is alanine,
            asparagine, aspartic acid, glutamic
            acid, glutamine, glycine, histidine,
            isoleucine, leucine, methionine,
            phenylalanine, proline, serine,
            threonine, tryptophan, tyrosine, or
            valine; Xaa in position 9 is alanine,
            arganine, asparagine, aspartic acid,
            glutamic acid, glutamine, glycine,
            histidine, isoleucine, leucine, lysine,
            methionine, phenylalanine, proline,
            serine, threonine, tryptophan, tyrosine,
            or valine; Xaa in position 10 is
            alanine, cysteine when Xaa in
            position 34 is cysteine, glycine or
            serine; Xaa in position 11 is arginine
            or lysine; Xaa in position 12 is alanine
            or glycine; Xaa in position 13 is
            alanine, arginine, asparagine,
            glutamine, glycine, histidine,
            isoleucine, leucine, lysine methionine,
            phenylalanine, proline, serine,
            threonine, tryptophan, tyrosine or
            valine; Xaa in position 14, Xaa in
            position 15, and Xaa in position 16 is
            any natural amino acid; Xaa in position 30 is alanine, arginine, asparagine, aspartic acid, glutamic acid, glutamine, glycine, histidine, isoleucine, leucine, lysine, methionine, phenylalanine, proline, serine, threonine, tryptophan, tyrosine or valine; Xaa in position 31 is phenylalanine, tryptophan or tyrosine; Xaa in position 34 is alanine, cysteine when Xaa in position 10 is cysteine, glycine, or serine; Xaa in position 35 is alanine, arginine, asparagine, aspartic acid, glutamic acid, glutamine, glycine, histidine, isoleucine, leucine, lysine, methionine, phenylalanine, proline, serine, threonine, tryptophan, tyrosine, or valine; Xaa in position 41 is phenylalanine, tryptophan or tyrosine; and Xaa in position 42 is any natural amino acid.

( x i ) SEQUENCE DESCRIPTION: SEQ ID NO: 3:

| Cys | Leu | Glu | Pro | Pro | Tyr | Xaa | Gly | Xaa | Xaa | Xaa | Xaa | Xaa | Xaa | Xaa | Xaa |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | Phe | Tyr | Asn | Ala | Lys | Ala | Gly | Leu | Cys | Gln | Thr | Phe | Xaa | Xaa | Gly |
|-----|-----|-----|-----|-----|-----|-----|-----|-----|-----|-----|-----|-----|-----|-----|-----|
|     |     |     | 20  |     |     |     |     | 25  |     |     |     |     |     | 30  |     |

| Gly | Xaa | Xaa | Ala | Lys | Arg | Asn | Asn | Xaa | Xaa | Ser | Ala | Glu | Asp | Cys | Met |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Thr | Cys |
|-----|-----|-----|
|     | 50  |     |

( 2 ) INFORMATION FOR SEQ ID NO: 4:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i x ) FEATURE:
        ( D ) OTHER INFORMATION: Xaa in position 1 is alanine or arginine; Xaa in position 11 is alanine, aspartic acid, glutamic acid, glycine, proline, serine, threonine or valine; Xaa in position 13 is alanine, glutamine, histidine, isoleucine, leucine, methionine, phenylalanine, proline, tryptophan, tyrosine, or valine; Xaa in position 14 is cysteine; Xaa in position 15 is arginine, or lysine; Xaa in position 16 is alanine or glycine; Xaa in position 17 is alanine, isoleucine, leucine, methionine, or tyrosine; Xaa in position 18 is histidine, isoleucine, phenylalanine or tyrosine; Xaa in position 19 is asparagine, glutamine, histidine, isoleucine, leucine, lysine, proline, threonine or valine; Xaa in position 20 is arginine or serine; Xaa in position 34 is aspartic acid, histidine, isoleucine, leucine, phenylalanine, serine, threonine, tryptophan, tyrosine, or valine; Xaa in position 35 is tyrosine; Xaa in position 38 is cysteine; Xaa in position 39 is arganine, asparagine, glutamic acid, glycine, histidine, leucine, methionine, phenylalanine, tryptophan, or tyrosine; Xaa in position 45 is phenylalanine; and Xaa in position 46 is aspartic acid, glutamic acid, lysine, phenylalanine, tryptophan, or tyrosine.

( x i ) SEQUENCE DESCRIPTION: SEQ ID NO: 4:

```
Xaa  Pro  Asp  Phe  Cys  Leu  Glu  Pro  Pro  Tyr  Xaa  Gly  Xaa  Xaa  Xaa  Xaa
 1                    5                         10                        15

Xaa  Xaa  Xaa  Xaa  Tyr  Phe  Tyr  Asn  Ala  Lys  Ala  Gly  Leu  Cys  Gln  Thr
               20                         25                        30

Phe  Xaa  Xaa  Gly  Gly  Xaa  Xaa  Ala  Lys  Arg  Asn  Asn  Xaa  Xaa  Ser  Ala
          35                         40                        45

Glu  Asp  Cys  Met  Arg  Thr  Cys  Gly  Gly  Ala
     50                        55
```

(2) INFORMATION FOR SEQ ID NO: 5:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Ala  Pro  Asp  Phe  Cys  Leu  Glu  Pro  Pro  Tyr  Asp  Gly  Pro  Cys  Lys  Ala
 1                    5                         10                        15

Ile  Ile  Lys  Arg  Tyr  Phe  Tyr  Asn  Ala  Lys  Ala  Gly  Leu  Cys  Gln  Thr
               20                         25                        30

Phe  Val  Tyr  Gly  Gly  Cys  Glu  Ala  Lys  Arg  Asn  Asn  Phe  Glu  Ser  Ala
          35                         40                        45

Glu  Asp  Cys  Met  Arg  Thr  Cys  Gly  Gly  Ala
     50                        55
```

(2) INFORMATION FOR SEQ ID NO: 6:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Ala  Pro  Asp  Phe  Cys  Leu  Glu  Pro  Pro  Tyr  Glu  Gly  Pro  Cys  Lys  Ala
 1                    5                         10                        15

Ile  Ile  Lys  Arg  Tyr  Phe  Tyr  Asn  Ala  Lys  Ala  Gly  Leu  Cys  Gln  Thr
               20                         25                        30

Phe  Val  Tyr  Gly  Gly  Cys  Glu  Ala  Lys  Arg  Asn  Asn  Phe  Glu  Ser  Ala
          35                         40                        45

Glu  Asp  Cys  Met  Arg  Thr  Cys  Gly  Gly  Ala
     50                        55
```

(2) INFORMATION FOR SEQ ID NO: 7:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Ala  Pro  Asp  Phe  Cys  Leu  Glu  Pro  Pro  Tyr  Thr  Gly  Ile  Cys  Arg  Ala
 1                    5                         10                        15

Tyr  Ile  Lys  Arg  Tyr  Phe  Tyr  Asn  Ala  Lys  Ala  Gly  Leu  Cys  Gln  Thr
```

```
                         20                     25                          30
Phe  Val  Tyr  Gly  Gly  Cys  Leu  Ala  Lys  Arg  Asn  Asn  Phe  Glu  Ser  Ala
               35                      40                       45

Glu  Asp  Cys  Met  Arg  Thr  Cys  Gly  Gly  Ala
          50                      55
```

( 2 ) INFORMATION FOR SEQ ID NO: 8:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 8:

```
Ala  Pro  Asp  Phe  Cys  Leu  Glu  Pro  Pro  Tyr  Asp  Gly  Pro  Cys  Arg  Ala
                         5                      10                      15

Ile  Ile  Lys  Arg  Tyr  Phe  Tyr  Asn  Ala  Lys  Ala  Gly  Leu  Cys  Gln  Thr
               20                      25                      30

Phe  Val  Tyr  Gly  Gly  Cys  Glu  Ala  Lys  Arg  Asn  Asn  Phe  Glu  Ser  Ala
               35                      40                      45

Glu  Asp  Cys  Met  Arg  Thr  Cys  Gly  Gly  Ala
          50                      55
```

( 2 ) INFORMATION FOR SEQ ID NO: 9:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 9:

```
Ala  Pro  Asp  Phe  Cys  Leu  Glu  Pro  Pro  Tyr  Asp  Gly  Pro  Cys  Arg  Ala
                         5                      10                      15

Ile  Ile  Lys  Arg  Tyr  Phe  Tyr  Asn  Ala  Lys  Ala  Gly  Leu  Cys  Gln  Thr
               20                      25                      30

Phe  Asp  Tyr  Gly  Gly  Cys  Leu  Ala  Lys  Arg  Asn  Asn  Phe  Lys  Ser  Ala
               35                      40                      45

Glu  Asp  Cys  Met  Arg  Thr  Cys  Gly  Gly  Ala
          50                      55
```

( 2 ) INFORMATION FOR SEQ ID NO: 10:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 10:

```
Ala  Pro  Asp  Phe  Cys  Leu  Glu  Pro  Pro  Tyr  Thr  Gly  Pro  Cys  Arg  Ala
                         5                      10                      15

Tyr  Ile  Thr  Arg  Tyr  Phe  Tyr  Asn  Ala  Lys  Ala  Gly  Leu  Cys  Gln  Thr
               20                      25                      30

Phe  Val  Tyr  Gly  Gly  Cys  Phe  Ala  Lys  Arg  Asn  Asn  Phe  Glu  Ser  Ala
               35                      40                      45
```

```
Glu Asp Cys Met Arg Thr Cys Gly Gly Ala
 50                  55
```

( 2 ) INFORMATION FOR SEQ ID NO: 11:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 11:

```
Ala Pro Asp Phe Cys Leu Glu Pro Pro Tyr Asp Gly Pro Cys Lys Ala
             5                  10                 15
Ile Ile Lys Arg Tyr Phe Tyr Asn Ala Lys Ala Gly Leu Cys Gln Thr
             20                 25                 30
Phe Val Tyr Gly Gly Cys Phe Ala Lys Arg Asn Asn Phe Glu Ser Ala
             35              40                 45
Glu Asp Cys Met Arg Thr Cys Gly Gly Ala
 50                  55
```

( 2 ) INFORMATION FOR SEQ ID NO: 12:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 12:

```
Ala Pro Asp Phe Cys Leu Glu Pro Pro Tyr Asp Gly Pro Cys Lys Ala
             5                  10                 15
Ile Ile Lys Arg Tyr Phe Tyr Asn Ala Lys Ala Gly Leu Cys Gln Thr
             20                 25                 30
Phe Val Tyr Gly Gly Cys Tyr Ala Lys Arg Asn Asn Phe Glu Ser Ala
             35              40                 45
Glu Asp Cys Met Arg Thr Cys Gly Gly Ala
 50                  55
```

( 2 ) INFORMATION FOR SEQ ID NO: 13:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 13:

```
Ala Pro Asp Phe Cys Leu Glu Pro Pro Tyr Asp Gly Pro Cys Arg Ala
             5                  10                 15
Ile Ile Lys Arg Tyr Phe Tyr Asn Ala Lys Ala Gly Leu Cys Gln Thr
             20                 25                 30
Phe Val Tyr Gly Gly Cys Phe Ala Lys Arg Asn Asn Phe Glu Ser Ala
             35              40                 45
Glu Asp Cys Met Arg Thr Cys Gly Gly Ala
 50                  55
```

( 2 ) INFORMATION FOR SEQ ID NO: 14:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 14:

```
Ala Pro Asp Phe Cys Leu Glu Pro Pro Tyr Asp Gly Pro Cys Arg Ala
                  5                  10                  15
Ile Ile Lys Arg Tyr Phe Tyr Asn Ala Lys Ala Gly Leu Cys Gln Thr
             20                  25                  30
Phe Val Tyr Gly Gly Cys Phe Ala Lys Arg Asn Asn Phe Glu Ser Ala
         35                  40                  45
Glu Asp Cys Met Arg Thr Cys Gly Gly Ala
         50                  55
```

(2) INFORMATION FOR SEQ ID NO: 15:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 15:

```
Ala Pro Asp Phe Cys Leu Glu Pro Pro Tyr Thr Gly Pro Cys Arg Ala
                  5                  10                  15
Ile Ile Lys Arg Tyr Phe Tyr Asn Ala Lys Ala Gly Leu Cys Gln Thr
             20                  25                  30
Phe Val Tyr Gly Gly Cys Phe Ala Lys Arg Asn Asn Phe Glu Ser Ala
         35                  40                  45
Glu Asp Cys Met Arg Thr Cys Gly Gly Ala
         50                  55
```

(2) INFORMATION FOR SEQ ID NO: 16:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 16:

```
Ala Pro Asp Phe Cys Leu Glu Pro Pro Tyr Thr Gly Pro Cys Arg Ala
                  5                  10                  15
Tyr Ile Thr Arg Tyr Phe Tyr Asn Ala Lys Ala Gly Leu Cys Gln Thr
             20                  25                  30
Phe Val Tyr Gly Gly Cys Tyr Ala Lys Arg Asn Asn Phe Tyr Ser Ala
         35                  40                  45
Glu Asp Cys Met Arg Thr Cys Gly Gly Ala
         50                  55
```

(2) INFORMATION FOR SEQ ID NO: 17:

(i) SEQUENCE CHARACTERISTICS:
    (A) LENGTH: 58 amino acids
    (B) TYPE: amino acid
    (C) STRANDEDNESS: single ( D ) TOPOLOGY: linear ( i i ) MOLECULE TYPE: peptide ( x i ) SEQUENCE DESCRIPTION: SEQ ID NO: 17:

| Ala | Pro | Asp | Phe | Cys | Leu | Glu | Pro | Pro | Tyr | Glu | Gly | Pro | Cys | Arg | Ala |
|---|---|---|---|---|---|---|---|---|---|---|---|---|---|---|---|
| | | | | 5 | | | | | 10 | | | | | 15 | |
| Tyr | Ile | Thr | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Tyr | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 |

( 2 ) INFORMATION FOR SEQ ID NO: 18:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 18:

| Ala | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
| | | | | 5 | | | | | 10 | | | | | 15 | |
| Met | His | His | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Phe | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 |

( 2 ) INFORMATION FOR SEQ ID NO: 19:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 19:

| Ala | Pro | Asp | Phe | Cys | Leu | Glu | Pro | Pro | Tyr | Asp | Gly | Pro | Cys | Arg | Ala |
|---|---|---|---|---|---|---|---|---|---|---|---|---|---|---|---|
| | | | | 5 | | | | | 10 | | | | | 15 | |
| Leu | His | Leu | Arg | Tyr | Phe | Tyr | Asn | Ala | Lys | Ala | Gly | Leu | Cys | Gln | Thr |
| | | | 20 | | | | | 25 | | | | | 30 | | |
| Phe | Tyr | Tyr | Gly | Gly | Cys | Leu | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala |
| | 50 | | | | | 55 |

( 2 ) INFORMATION FOR SEQ ID NO: 20:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 20:

Ala Pro Asp Phe Cys Leu Glu Pro Pro Tyr Glu Gly Tyr Cys Arg Ala
                  5                   10                  15

Leu His Ile Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
            35              40                  45

Glu Asp Cys Met Arg Thr Cys Gly Gly Ala
        50              55

( 2 ) INFORMATION FOR SEQ ID NO: 21:

( i ) SEQUENCE CHARACTERISTICS:
           ( A ) LENGTH: 58 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO: 21:

Ala Pro Asp Phe Cys Leu Glu Pro Pro Tyr Glu Gly Ala Cys Arg Ala
                  5                   10                  15

Leu His Leu Arg Tyr Phe Tyr Asn Ala Lys Ala Gly Leu Cys Gln Thr
            20                  25                  30

Phe Tyr Tyr Gly Gly Cys Tyr Ala Lys Arg Asn Asn Phe Glu Ser Ala
            35              40                  45

Glu Asp Cys Met Arg Thr Cys Gly Gly Ala
        50              55

( 2 ) INFORMATION FOR SEQ ID NO: 22:

( i ) SEQUENCE CHARACTERISTICS:
           ( A ) LENGTH: 58 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO: 22:

Ala Pro Asp Phe Cys Leu Glu Pro Pro Tyr Glu Gly Phe Cys Arg Ala
                  5                   10                  15

Leu His Pro Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
            35              40                  45

Glu Asp Cys Met Arg Thr Cys Gly Gly Ala
        50              55

( 2 ) INFORMATION FOR SEQ ID NO: 23:

( i ) SEQUENCE CHARACTERISTICS:
           ( A ) LENGTH: 58 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO: 23:

Ala Pro Asp Phe Cys Leu Glu Pro Pro Tyr Glu Gly Phe Cys Arg Ala
                  5                   10                  15

Leu His Thr Arg Tyr Phe Tyr Asn Ala Lys Ala Gly Leu Cys Gln Thr

```
                        20                     25                          30
Phe  Tyr  Tyr  Gly  Gly  Cys  His  Ala  Lys  Arg  Asn  Asn  Phe  Glu  Ser  Ala
              35                       40                       45
Glu  Asp  Cys  Met  Arg  Thr  Cys  Gly  Gly  Ala
         50                        55
```

( 2 ) INFORMATION FOR SEQ ID NO: 24:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 24:

```
Ala  Pro  Asp  Phe  Cys  Leu  Glu  Pro  Pro  Tyr  Asp  Gly  Pro  Cys  Arg  Ala
                        5                      10                          15
Leu  His  Thr  Arg  Tyr  Phe  Tyr  Asn  Ala  Lys  Ala  Gly  Leu  Cys  Gln  Thr
              20                       25                       30
Phe  Thr  Tyr  Gly  Gly  Cys  Phe  Ala  Lys  Arg  Asn  Asn  Phe  Glu  Ser  Ala
              35                       40                       45
Glu  Asp  Cys  Met  Arg  Thr  Cys  Gly  Gly  Ala
         50                        55
```

( 2 ) INFORMATION FOR SEQ ID NO: 25:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 25:

```
Ala  Pro  Asp  Phe  Cys  Leu  Glu  Pro  Pro  Tyr  Pro  Gly  Tyr  Cys  Arg  Ala
                        5                      10                          15
Leu  His  Leu  Arg  Tyr  Phe  Tyr  Asn  Ala  Lys  Ala  Gly  Leu  Cys  Gln  Thr
              20                       25                       30
Phe  Thr  Tyr  Gly  Gly  Cys  His  Ala  Lys  Arg  Asn  Asn  Phe  Glu  Ser  Ala
              35                       40                       45
Glu  Asp  Cys  Met  Arg  Thr  Cys  Gly  Gly  Ala
         50                        55
```

( 2 ) INFORMATION FOR SEQ ID NO: 26:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 26:

```
Ala  Pro  Asp  Phe  Cys  Leu  Glu  Pro  Pro  Tyr  Asp  Gly  Pro  Cys  Arg  Ala
                        5                      10                          15
Leu  His  Gln  Arg  Tyr  Phe  Tyr  Asn  Ala  Lys  Ala  Gly  Leu  Cys  Gln  Thr
              20                       25                       30
Phe  Thr  Tyr  Gly  Gly  Cys  Arg  Ala  Lys  Arg  Asn  Asn  Phe  Glu  Ser  Ala
              35                       40                       45
```

```
Glu Asp Cys Met Arg Thr Cys Gly Gly Ala
    50                  55
```

( 2 ) INFORMATION FOR SEQ ID NO: 27:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 27:

```
Ala Pro Asp Phe Cys Leu Glu Pro Pro Tyr Glu Gly Pro Cys Arg Ala
                5                   10                  15
Ile His Pro Arg Tyr Phe Tyr Asn Ala Lys Ala Gly Leu Cys Gln Thr
            20                  25                  30
Phe Leu Tyr Gly Gly Cys Tyr Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 28:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 28:

```
Ala Pro Asp Phe Cys Leu Glu Pro Pro Tyr Gly Gly Val Cys Arg Ala
                5                   10                  15
Ile His Leu Arg Tyr Phe Tyr Asn Ala Lys Ala Gly Leu Cys Gln Thr
            20                  25                  30
Phe Ile Tyr Gly Gly Cys Tyr Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 29:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 29:

```
Ala Pro Asp Phe Cys Leu Glu Pro Pro Tyr Ala Gly Pro Cys Arg Ala
                5                   10                  15
Leu His Gln Arg Tyr Phe Tyr Asn Ala Lys Ala Gly Leu Cys Gln Thr
            20                  25                  30
Phe His Tyr Gly Gly Cys Phe Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 30:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 30:

Ala Pro Asp Phe Cys Leu Glu Pro Pro Pro Gly Tyr Cys Arg Ala
                 5                  10                 15
Leu His Leu Arg Tyr Phe Tyr Asn Ala Lys Ala Gly Leu Cys Gln Thr
             20                  25                  30
Phe His Tyr Gly Gly Cys His Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 31:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 31:

Ala Pro Asp Phe Cys Leu Glu Pro Pro Tyr Gly Gly Pro Cys Arg Ala
                 5                  10                 15
Leu His Pro Arg Tyr Phe Tyr Asn Ala Lys Ala Gly Leu Cys Gln Thr
             20                  25                  30
Phe Phe Tyr Gly Gly Cys Phe Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 32:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 32:

Ala Pro Asp Phe Cys Leu Glu Pro Pro Tyr Gly Gly Val Cys Arg Ala
                 5                  10                 15
Leu His Ile Arg Tyr Phe Tyr Asn Ala Lys Ala Gly Leu Cys Gln Thr
             20                  25                  30
Phe Tyr Tyr Gly Gly Cys Asn Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 33:

( i ) SEQUENCE CHARACTERISTICS:
    ( A ) LENGTH: 58 amino acids
    ( B ) TYPE: amino acid
    ( C ) STRANDEDNESS: single ( D ) TOPOLOGY: linear ( i i ) MOLECULE TYPE: peptide ( x i ) SEQUENCE DESCRIPTION: SEQ ID NO: 33:

| Ala | Pro | Asp | Phe | Cys | Leu | Glu | Pro | Pro | Tyr | Glu | Gly | Gln | Cys | Arg | Ala |
|---|---|---|---|---|---|---|---|---|---|---|---|---|---|---|---|
| | | | | 5 | | | | | 10 | | | | | 15 | |
| Leu | His | Leu | Arg | Tyr | Phe | Tyr | Asn | Ala | Lys | Ala | Gly | Leu | Cys | Gln | Thr |
| | | | 20 | | | | | 25 | | | | | 30 | | |
| Phe | Ser | Tyr | Gly | Gly | Cys | Tyr | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

( 2 ) INFORMATION FOR SEQ ID NO: 34:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 34:

| Ala | Pro | Asp | Phe | Cys | Leu | Glu | Pro | Pro | Tyr | Ala | Gly | Tyr | Cys | Arg | Ala |
|---|---|---|---|---|---|---|---|---|---|---|---|---|---|---|---|
| | | | | 5 | | | | | 10 | | | | | 15 | |
| Ile | His | His | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Tyr | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

( 2 ) INFORMATION FOR SEQ ID NO: 35:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 35:

| Ala | Pro | Asp | Phe | Cys | Leu | Glu | Pro | Pro | Tyr | Thr | Gly | Ile | Cys | Arg | Ala |
|---|---|---|---|---|---|---|---|---|---|---|---|---|---|---|---|
| | | | | 5 | | | | | 10 | | | | | 15 | |
| Ile | His | His | Arg | Tyr | Phe | Tyr | Asn | Ala | Lys | Ala | Gly | Leu | Cys | Gln | Thr |
| | | | 20 | | | | | 25 | | | | | 30 | | |
| Phe | Val | Tyr | Gly | Gly | Cys | Leu | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

( 2 ) INFORMATION FOR SEQ ID NO: 36:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 36:

Ala Pro Asp Phe Cys Leu Glu Pro Pro Tyr Pro Gly Pro Cys Arg Ala
                  5                   10                  15

Leu His Thr Arg Tyr Phe Tyr Asn Ala Lys Ala Gly Leu Cys Gln Thr
                 20                  25                  30

Phe Phe Tyr Gly Gly Cys Tyr Ala Lys Arg Asn Asn Phe Glu Ser Ala
                 35                  40                  45

Glu Asp Cys Met Arg Thr Cys Gly Gly Ala
                 50                  55

(2) INFORMATION FOR SEQ ID NO: 37:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Ala Pro Asp Phe Cys Leu Glu Pro Pro Tyr Val Gly His Cys Arg Ala
                  5                   10                  15

Leu His Leu Arg Tyr Phe Tyr Asn Ala Lys Ala Gly Leu Cys Gln Thr
                 20                  25                  30

Phe Leu Tyr Gly Gly Cys His Ala Lys Arg Asn Asn Phe Glu Ser Ala
                 35                  40                  45

Glu Asp Cys Met Arg Thr Cys Gly Gly Ala
                 50                  55

(2) INFORMATION FOR SEQ ID NO: 38:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Ala Pro Asp Phe Cys Leu Glu Pro Pro Tyr Thr Gly Ile Cys Arg Ala
                  5                   10                  15

Leu His Gln Arg Tyr Phe Tyr Asn Ala Lys Ala Gly Leu Cys Gln Thr
                 20                  25                  30

Phe Val Tyr Gly Gly Cys Leu Ala Lys Arg Asn Asn Phe Glu Ser Ala
                 35                  40                  45

Glu Asp Cys Met Arg Thr Cys Gly Gly Ala
                 50                  55

(2) INFORMATION FOR SEQ ID NO: 39:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Ala Pro Asp Phe Cys Leu Glu Pro Pro Tyr Thr Gly Ile Cys Arg Ala
                  5                   10                  15

Leu His Ile Arg Tyr Phe Tyr Asn Ala Lys Ala Gly Leu Cys Gln Thr

```
                         20                      25                        30
Phe  Val  Tyr  Gly  Gly  Cys  Leu  Ala  Lys  Arg  Asn  Asn  Phe  Glu  Ser  Ala
               35                      40                      45

Glu  Asp  Cys  Met  Arg  Thr  Cys  Gly  Gly  Ala
          50                      55
```

(2) INFORMATION FOR SEQ ID NO: 40:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Ala  Pro  Asp  Phe  Cys  Leu  Glu  Pro  Pro  Tyr  Thr  Gly  Ile  Cys  Arg  Ala
                    5                        10                      15

Leu  His  Thr  Arg  Tyr  Phe  Tyr  Asn  Ala  Lys  Ala  Gly  Leu  Cys  Gln  Thr
               20                      25                      30

Phe  Val  Tyr  Gly  Gly  Cys  Leu  Ala  Lys  Arg  Asn  Asn  Phe  Glu  Ser  Ala
               35                      40                      45

Glu  Asp  Cys  Met  Arg  Thr  Cys  Gly  Gly  Ala
          50                      55
```

(2) INFORMATION FOR SEQ ID NO: 41:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

```
Ala  Pro  Asp  Phe  Cys  Leu  Glu  Pro  Pro  Tyr  Thr  Gly  Ile  Cys  Arg  Ala
                    5                        10                      15

Leu  His  Lys  Arg  Tyr  Phe  Tyr  Asn  Ala  Lys  Ala  Gly  Leu  Cys  Gln  Thr
               20                      25                      30

Phe  Val  Tyr  Gly  Gly  Cys  Leu  Ala  Lys  Arg  Asn  Asn  Phe  Glu  Ser  Ala
               35                      40                      45

Glu  Asp  Cys  Met  Arg  Thr  Cys  Gly  Gly  Ala
          50                      55
```

(2) INFORMATION FOR SEQ ID NO: 42:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

```
Ala  Pro  Asp  Phe  Cys  Leu  Glu  Pro  Pro  Tyr  Thr  Gly  Ile  Cys  Arg  Ala
                    5                        10                      15

Ile  His  Leu  Arg  Tyr  Phe  Tyr  Asn  Ala  Lys  Ala  Gly  Leu  Cys  Gln  Thr
               20                      25                      30

Phe  Val  Tyr  Gly  Gly  Cys  Leu  Ala  Lys  Arg  Asn  Asn  Phe  Glu  Ser  Ala
               35                      40                      45
```

Glu Asp Cys Met Arg Thr Cys Gly Gly Ala
50                      55

( 2 ) INFORMATION FOR SEQ ID NO: 43:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 43:

Ala Pro Asp Phe Cys Leu Glu Pro Pro Tyr Thr Gly Ile Cys Arg Ala
                5                   10                      15

Ile His Val Arg Tyr Phe Tyr Asn Ala Lys Ala Gly Leu Cys Gln Thr
            20              25                      30

Phe Val Tyr Gly Gly Cys Leu Ala Lys Arg Asn Asn Phe Glu Ser Ala
            35              40                      45

Glu Asp Cys Met Arg Thr Cys Gly Gly Ala
50                      55

( 2 ) INFORMATION FOR SEQ ID NO: 44:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 44:

Ala Pro Asp Phe Cys Leu Glu Pro Pro Tyr Thr Gly Ile Cys Arg Ala
                5                   10                      15

Met His Leu Arg Tyr Phe Tyr Asn Ala Lys Ala Gly Leu Cys Gln Thr
            20              25                      30

Phe Val Tyr Gly Gly Cys Leu Ala Lys Arg Asn Asn Phe Glu Ser Ala
            35              40                      45

Glu Asp Cys Met Arg Thr Cys Gly Gly Ala
50                      55

( 2 ) INFORMATION FOR SEQ ID NO: 45:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 45:

Ala Pro Asp Phe Cys Leu Glu Pro Pro Tyr Thr Gly Ile Cys Arg Ala
                5                   10                      15

Tyr Tyr Lys Arg Tyr Phe Tyr Asn Ala Lys Ala Gly Leu Cys Gln Thr
            20              25                      30

Phe Val Tyr Gly Gly Cys Leu Ala Lys Arg Asn Asn Phe Glu Ser Ala
            35              40                      45

Glu Asp Cys Met Arg Thr Cys Gly Gly Ala
50                      55

( 2 ) INFORMATION FOR SEQ ID NO: 46:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 46:

Ala Pro Asp Phe Cys Leu Glu Pro Pro Tyr Pro Gly Phe Cys Arg Ala
                 5                  10                 15
Leu His Lys Arg Tyr Phe Tyr Asn Ala Lys Ala Gly Leu Cys Gln Thr
             20              25                  30
Phe His Tyr Gly Gly Cys Phe Ala Lys Arg Asn Asn Phe Glu Ser Ala
         35              40                  45
Glu Asp Cys Met Arg Thr Cys Gly Gly Ala
     50              55

( 2 ) INFORMATION FOR SEQ ID NO: 47:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 47:

Arg Pro Asp Phe Cys Leu Glu Pro Pro Tyr Asp Gly Pro Cys Arg Ala
                 5                  10                 15
Leu His Pro Arg Tyr Phe Tyr Asn Ala Lys Ala Gly Leu Cys Gln Thr
             20              25                  30
Phe Trp Tyr Gly Gly Cys Tyr Ala Lys Arg Asn Asn Phe Glu Ser Ala
         35              40                  45
Glu Asp Cys Met Arg Thr Cys Gly Gly Ala
     50              55

( 2 ) INFORMATION FOR SEQ ID NO: 48:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 48:

Arg Pro Asp Phe Cys Leu Glu Pro Pro Tyr Asp Gly Pro Cys Arg Ala
                 5                  10                 15
Leu His Pro Arg Tyr Phe Tyr Asn Ala Lys Ala Gly Leu Cys Gln Thr
             20              25                  30
Phe Trp Tyr Gly Gly Cys Leu Ala Lys Arg Asn Asn Phe Glu Ser Ala
         35              40                  45
Glu Asp Cys Met Arg Thr Cys Gly Gly Ala
     50              55

( 2 ) INFORMATION FOR SEQ ID NO: 49:

( i ) SEQUENCE CHARACTERISTICS:
    ( A ) LENGTH: 58 amino acids
    ( B ) TYPE: amino acid
    ( C ) STRANDEDNESS: single (D) TOPOLOGY: linear (ii) MOLECULE TYPE: peptide (xi) SEQUENCE DESCRIPTION: SEQ ID NO: 49:

Arg Pro Asp Phe Cys Leu Glu Pro Pro Tyr Asp Gly Pro Cys Arg Ala
                 5                  10                 15
Leu His His Arg Tyr Phe Tyr Asn Ala Lys Ala Gly Leu Cys Gln Thr
                20                  25                 30
Phe Tyr Tyr Gly Gly Cys Arg Ala Lys Arg Asn Asn Phe Glu Ser Ala
            35              40                  45
Glu Asp Cys Met Arg Thr Cys Gly Gly Ala
    50                  55

(2) INFORMATION FOR SEQ ID NO: 50:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 50:

Arg Pro Asp Phe Cys Leu Glu Pro Pro Tyr Glu Gly Trp Cys Arg Ala
                 5                  10                 15
Leu His His Arg Tyr Phe Tyr Asn Ala Lys Ala Gly Leu Cys Gln Thr
                20                  25                 30
Phe Ile Tyr Gly Gly Cys Gly Ala Lys Arg Asn Asn Phe Glu Ser Ala
            35              40                  45
Glu Asp Cys Met Arg Thr Cys Gly Gly Ala
    50                  55

(2) INFORMATION FOR SEQ ID NO: 51:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 51:

Arg Pro Asp Phe Cys Leu Glu Pro Pro Tyr Thr Gly Pro Cys Arg Ala
                 5                  10                 15
Leu His His Arg Tyr Phe Tyr Asn Ala Lys Ala Gly Leu Cys Gln Thr
                20                  25                 30
Phe Phe Tyr Gly Gly Cys Phe Ala Lys Arg Asn Asn Phe Glu Ser Ala
            35              40                  45
Glu Asp Cys Met Arg Thr Cys Gly Gly Ala
    50                  55

(2) INFORMATION FOR SEQ ID NO: 52:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 52:

Arg Pro Asp Phe Cys Leu Glu Pro Pro Tyr Ser Gly Leu Cys Arg Ala
                 5                  10                 15

Leu His Lys Arg Tyr Phe Tyr Asn Ala Lys Ala Gly Leu Cys Gln Thr
             20                  25                 30

Phe Tyr Tyr Gly Gly Cys Tyr Ala Lys Arg Asn Asn Phe Glu Ser Ala
         35                  40                 45

Glu Asp Cys Met Arg Thr Cys Gly Gly Ala
     50                  55

( 2 ) INFORMATION FOR SEQ ID NO: 53:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 53:

Arg Pro Asp Phe Cys Leu Glu Pro Pro Tyr Pro Gly Ile Cys Arg Ala
                 5                  10                 15

Leu His Lys Arg Tyr Phe Tyr Asn Ala Lys Ala Gly Leu Cys Gln Thr
             20                  25                 30

Phe His Tyr Gly Gly Cys Phe Ala Lys Arg Asn Asn Phe Glu Ser Ala
         35                  40                 45

Glu Asp Cys Met Arg Thr Cys Gly Gly Ala
     50                  55

( 2 ) INFORMATION FOR SEQ ID NO: 54:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 54:

Arg Pro Asp Phe Cys Leu Glu Pro Pro Tyr Ser Gly Leu Cys Arg Ala
                 5                  10                 15

Leu His Lys Arg Tyr Phe Tyr Asn Ala Lys Ala Gly Leu Cys Gln Thr
             20                  25                 30

Phe Tyr Tyr Gly Gly Cys Phe Ala Lys Arg Asn Asn Phe Glu Ser Ala
         35                  40                 45

Glu Asp Cys Met Arg Thr Cys Gly Gly Ala
     50                  55

( 2 ) INFORMATION FOR SEQ ID NO: 55:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 55:

Arg Pro Asp Phe Cys Leu Glu Pro Pro Tyr Pro Gly Ile Cys Arg Ala
                 5                  10                 15

Leu His Lys Arg Tyr Phe Tyr Asn Ala Lys Ala Gly Leu Cys Gln Thr

```
                        20                      25                          30
Phe  Tyr  Tyr  Gly  Gly  Cys  Met  Ala  Lys  Arg  Asn  Asn  Phe  Glu  Ser  Ala
          35                      40                      45
Glu  Asp  Cys  Met  Arg  Thr  Cys  Gly  Gly  Ala
     50                      55
```

( 2 ) INFORMATION FOR SEQ ID NO: 56:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 56:

```
Arg  Pro  Asp  Phe  Cys  Leu  Glu  Pro  Pro  Tyr  Glu  Gly  Met  Cys  Arg  Ala
                    5                            10                      15
Ile  His  Lys  Arg  Tyr  Phe  Tyr  Asn  Ala  Lys  Ala  Gly  Leu  Cys  Gln  Thr
               20                       25                      30
Phe  Thr  Tyr  Gly  Gly  Cys  Met  Ala  Lys  Arg  Asn  Asn  Phe  Glu  Ser  Ala
          35                      40                      45
Glu  Asp  Cys  Met  Arg  Thr  Cys  Gly  Gly  Ala
     50                      55
```

( 2 ) INFORMATION FOR SEQ ID NO: 57:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 57:

```
Arg  Pro  Asp  Phe  Cys  Leu  Glu  Pro  Pro  Tyr  Pro  Gly  Val  Cys  Arg  Ala
                    5                            10                      15
Leu  His  Lys  Arg  Tyr  Phe  Tyr  Asn  Ala  Lys  Ala  Gly  Leu  Cys  Gln  Thr
               20                       25                      30
Phe  Ser  Tyr  Gly  Gly  Cys  Gln  Ala  Lys  Arg  Asn  Asn  Phe  Glu  Ser  Ala
          35                      40                      45
Glu  Asp  Cys  Met  Arg  Thr  Cys  Gly  Gly  Ala
     50                      55
```

( 2 ) INFORMATION FOR SEQ ID NO: 58:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 58:

```
Arg  Pro  Asp  Phe  Cys  Leu  Glu  Pro  Pro  Tyr  Glu  Gly  Leu  Cys  Arg  Ala
                    5                            10                      15
Leu  His  Lys  Arg  Tyr  Phe  Tyr  Asn  Ala  Lys  Ala  Gly  Leu  Cys  Gln  Thr
               20                       25                      30
Phe  Tyr  Tyr  Gly  Gly  Cys  Phe  Ala  Lys  Arg  Asn  Asn  Phe  Glu  Ser  Ala
          35                      40                      45
```

Glu Asp Cys Met Arg Thr Cys Gly Gly Ala
50                          55

( 2 ) INFORMATION FOR SEQ ID NO: 59:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 59:

Arg Pro Asp Phe Cys Leu Glu Pro Pro Tyr Pro Gly Leu Cys Arg Ala
            5                   10                  15

Leu His Lys Arg Tyr Phe Tyr Asn Ala Lys Ala Gly Leu Cys Gln Thr
            20                  25                  30

Phe Tyr Tyr Gly Gly Cys Tyr Ala Lys Arg Asn Asn Phe Glu Ser Ala
            35                  40                  45

Glu Asp Cys Met Arg Thr Cys Gly Gly Ala
50                          55

( 2 ) INFORMATION FOR SEQ ID NO: 60:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 60:

Arg Pro Asp Phe Cys Leu Glu Pro Pro Tyr Asp Gly Pro Cys Arg Ala
            5                   10                  15

Leu His Gln Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
50                          55

( 2 ) INFORMATION FOR SEQ ID NO: 61:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 61:

Arg Pro Asp Phe Cys Leu Glu Pro Ala Tyr Asp Gly Pro Cys Arg Ala
            5                   10                  15

Leu His Gln Arg Tyr Leu Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
50                          55

( 2 ) INFORMATION FOR SEQ ID NO: 62:

( i ) SEQUENCE CHARACTERISTICS:
  ( A ) LENGTH: 58 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 62:

Arg Pro Asp Phe Cys Leu Glu Pro Pro Tyr Thr Gly Ile Cys Arg Ala
                  5                  10                    15
Ala Phe Asn Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 63:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 63:

Arg Pro Asp Phe Cys Leu Glu Pro Pro Tyr Thr Gly Ile Cys Arg Ala
                  5                  10                    15
Phe Tyr Lys Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 64:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 64:

Arg Pro Asp Phe Cys Leu Glu Pro Pro Tyr Thr Gly Ile Cys Arg Ala
                  5                  10                    15
Tyr Tyr Lys Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
         50                  55

( 2 ) INFORMATION FOR SEQ ID NO: 65:

( i ) SEQUENCE CHARACTERISTICS:
    ( A ) LENGTH: 58 amino acids
    ( B ) TYPE: amino acid
    ( C ) STRANDEDNESS: single (D) TOPOLOGY: linear (i i) MOLECULE TYPE: peptide (x i) SEQUENCE DESCRIPTION: SEQ ID NO: 65:

Ala Pro Asp Phe Cys Leu Glu Pro Pro Tyr Asp Gly Pro Cys Arg Ala
                  5                   10                    15

Ile Ile Lys Arg Tyr Phe Tyr Asn Ala Lys Ala Gly Leu Cys Gln Thr
            20                  25                  30

Phe Val Tyr Gly Gly Cys Glu Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 66:

(i) SEQUENCE CHARACTERISTICS:
    (A) LENGTH: 58 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 66:

Ala Pro Asp Phe Cys Leu Glu Pro Pro Tyr Asp Gly Pro Cys Lys Ala
                  5                   10                    15

Ile Ile Lys Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 67:

(i) SEQUENCE CHARACTERISTICS:
    (A) LENGTH: 58 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 67:

Ala Pro Asp Phe Cys Leu Glu Pro Pro Tyr Asp Gly Pro Cys Lys Ala
                  5                   10                    15

Ile Ile Lys Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 68:

(i) SEQUENCE CHARACTERISTICS:
    (A) LENGTH: 58 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 68:

```
Ala  Pro  Asp  Phe  Cys  Leu  Glu  Pro  Pro  Tyr  Asp  Gly  Pro  Cys  Arg  Ala
                    5                        10                      15

Ile  Ile  Lys  Arg  Tyr  Phe  Tyr  Asn  Ala  Lys  Ala  Gly  Leu  Cys  Gln  Thr
               20                       25                      30

Phe  Val  Tyr  Gly  Gly  Cys  Phe  Ala  Lys  Arg  Asn  Asn  Phe  Glu  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 69:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 69:

```
Ala  Pro  Asp  Phe  Cys  Leu  Glu  Pro  Pro  Tyr  Asp  Gly  Pro  Cys  Arg  Ala
                    5                        10                      15

Ile  Ile  Lys  Arg  Tyr  Phe  Tyr  Asn  Ala  Lys  Ala  Gly  Leu  Cys  Gln  Thr
               20                       25                      30

Phe  Val  Tyr  Gly  Gly  Cys  Tyr  Ala  Lys  Arg  Asn  Asn  Phe  Glu  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 70:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 70:

```
Ala  Pro  Asp  Phe  Cys  Leu  Glu  Pro  Pro  Tyr  Thr  Gly  Pro  Cys  Arg  Ala
                    5                        10                      15

Ile  Ile  Lys  Arg  Tyr  Phe  Tyr  Asn  Ala  Lys  Ala  Gly  Leu  Cys  Gln  Thr
               20                       25                      30

Phe  Val  Tyr  Gly  Gly  Cys  Phe  Ala  Lys  Arg  Asn  Asn  Phe  Glu  Ser  Ala
               35                  40                       45

Glu  Asp  Cys  Met  Arg  Thr  Cys  Gly  Gly  Ala
          50                  55
```

( 2 ) INFORMATION FOR SEQ ID NO: 71:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 71:

```
Ala  Pro  Asp  Phe  Cys  Leu  Glu  Pro  Pro  Tyr  Glu  Gly  Pro  Cys  Arg  Ala
                    5                        10                      15

Tyr  Ile  Thr  Arg  Tyr  Phe  Tyr  Asn  Ala  Lys  Ala  Gly  Leu  Cys  Gln  Thr
```

|  | 20 | 25 | 30 |
|---|---|---|---|

Phe Val Tyr Gly Gly Cys Tyr Ala Lys Arg Asn Asn Phe Glu Ser Ala
       35                  40                 45

Glu Asp Cys Met Arg Thr Cys Gly Gly Ala
 50                       55

(2) INFORMATION FOR SEQ ID NO: 72:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Ala Pro Asp Phe Cys Leu Glu Pro Pro Tyr Thr Gly Pro Cys Arg Ala
               5                  10                 15

Met His His Arg Tyr Phe Tyr Asn Ala Lys Ala Gly Leu Cys Gln Thr
            20                  25                 30

Phe Val Tyr Gly Gly Cys Phe Ala Lys Arg Asn Asn Phe Glu Ser Ala
       35                  40                 45

Glu Asp Cys Met Arg Thr Cys Gly Gly Ala
 50                       55

(2) INFORMATION FOR SEQ ID NO: 73:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Ala Pro Asp Phe Cys Leu Glu Pro Pro Tyr Asp Gly Pro Cys Arg Ala
               5                  10                 15

Leu His Leu Arg Tyr Phe Tyr Asn Ala Lys Ala Gly Leu Cys Gln Thr
            20                  25                 30

Phe Tyr Tyr Gly Gly Cys Leu Ala Lys Arg Asn Asn Phe Glu Ser Ala
       35                  40                 45

Glu Asp Cys Met Arg Thr Cys Gly Gly Ala
 50                       55

(2) INFORMATION FOR SEQ ID NO: 74:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Ala Pro Asp Phe Cys Leu Glu Pro Pro Tyr Glu Gly Tyr Cys Arg Ala
               5                  10                 15

Leu His Ile Arg Tyr Phe Tyr Asn Ala Lys Ala Gly Leu Cys Gln Thr
            20                  25                 30

Phe Tyr Tyr Gly Gly Cys His Ala Lys Arg Asn Asn Phe Glu Ser Ala
       35                  40                 45

Glu Asp Cys Met Arg Thr Cys Gly Gly Ala
50                      55

(2) INFORMATION FOR SEQ ID NO: 75:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Ala Pro Asp Phe Cys Leu Glu Pro Pro Tyr Glu Gly Ala Cys Arg Ala
            5                   10                  15
Leu His Leu Arg Tyr Phe Tyr Asn Ala Lys Ala Gly Leu Cys Gln Thr
                20              25                  30
Phe Tyr Tyr Gly Gly Cys Tyr Ala Lys Arg Asn Asn Phe Glu Ser Ala
            35              40                  45
Glu Asp Cys Met Arg Thr Cys Gly Gly Ala
50                      55

(2) INFORMATION FOR SEQ ID NO: 76:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

Ala Pro Asp Phe Cys Leu Glu Pro Pro Tyr Glu Gly Phe Cys Arg Ala
            5                   10                  15
Leu His Pro Arg Tyr Phe Tyr Asn Ala Lys Ala Gly Leu Cys Gln Thr
                20              25                  30
Phe Tyr Tyr Gly Gly Cys His Ala Lys Arg Asn Asn Phe Glu Ser Ala
            35              40                  45
Glu Asp Cys Met Arg Thr Cys Gly Gly Ala
50                      55

(2) INFORMATION FOR SEQ ID NO: 77:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 77:

Ala Pro Asp Phe Cys Leu Glu Pro Pro Tyr Glu Gly Phe Cys Arg Ala
            5                   10                  15
Leu His Thr Arg Tyr Phe Tyr Asn Ala Lys Ala Gly Leu Cys Gln Thr
                20              25                  30
Phe Tyr Tyr Gly Gly Cys His Ala Lys Arg Asn Asn Phe Glu Ser Ala
            35              40                  45
Glu Asp Cys Met Arg Thr Cys Gly Gly Ala
50                      55

(2) INFORMATION FOR SEQ ID NO: 78:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 78:

| Ala | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Thr | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Thr | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     |     | 50  |     |     |     | 55  |     |     |     |

(2) INFORMATION FOR SEQ ID NO: 79:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 79:

| Ala | Pro | Asp | Phe | Cys | Leu | Glu | Pro | Pro | Tyr | Pro | Gly | Tyr | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Leu | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Thr | Tyr | Gly | Gly | Cys | His | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     |     | 50  |     |     |     | 55  |     |     |     |

(2) INFORMATION FOR SEQ ID NO: 80:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 80:

| Ala | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Gln | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Thr | Tyr | Gly | Gly | Cys | Arg | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     |     | 50  |     |     |     | 55  |     |     |     |

(2) INFORMATION FOR SEQ ID NO: 81:

(i) SEQUENCE CHARACTERISTICS:
    (A) LENGTH: 58 amino acids
    (B) TYPE: amino acid
    (C) STRANDEDNESS: single (D) TOPOLOGY: linear (i i) MOLECULE TYPE: peptide (x i) SEQUENCE DESCRIPTION: SEQ ID NO: 81:

Ala Pro Asp Phe Cys Leu Glu Pro Pro Tyr Glu Gly Pro Cys Arg Ala
                5                   10                  15
Ile His Pro Arg Tyr Phe Tyr Asn Ala Lys Ala Gly Leu Cys Gln Thr
            20                  25                  30
Phe Leu Tyr Gly Gly Cys Tyr Ala Lys Arg Asn Asn Phe Glu Ser Ala
        35              40                      45
Glu Asp Cys Met Arg Thr Cys Gly Gly Ala
    50                  55

(2) INFORMATION FOR SEQ ID NO: 82:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 82:

Arg Pro Asp Phe Cys Leu Glu Pro Pro Tyr Thr Gly Ile Cys Arg Ala
                5                   10                  15
Leu His Ile Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35              40                      45
Glu Asp Cys Met Arg Thr Cys Gly Gly Ala
    50                  55

(2) INFORMATION FOR SEQ ID NO: 83:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 83:

Arg Pro Asp Phe Cys Leu Glu Pro Pro Tyr Asp Gly Pro Cys Arg Ala
                5                   10                  15
Leu His Thr Arg Tyr Phe Tyr Asn Ala Lys Ala Gly Leu Cys Gln Thr
            20                  25                  30
Phe Thr Tyr Gly Gly Cys Phe Ala Lys Arg Asn Asn Phe Glu Ser Ala
        35              40                      45
Glu Asp Cys Met Arg Thr Cys Gly Gly Ala
    50                  55

(2) INFORMATION FOR SEQ ID NO: 84:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 84:

| Arg | Pro | Asp | Phe | Cys | Leu | Glu | Pro | Pro | Tyr | Gly | Gly | Val | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |

| Ile | His | Leu | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Ile | Tyr | Gly | Gly | Cys | Tyr | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 85:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 85:

| Arg | Pro | Asp | Phe | Cys | Leu | Glu | Pro | Pro | Tyr | Glu | Gly | Pro | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |

| Ile | His | Pro | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Leu | Tyr | Gly | Gly | Cys | Tyr | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 86:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 86:

| Arg | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |

| Leu | His | Gln | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Thr | Tyr | Gly | Gly | Cys | Arg | Ala | Lys | Arg | Asn | Asn | Phe | Glu | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Asp | Cys | Met | Arg | Thr | Cys | Gly | Gly | Ala |
|-----|-----|-----|-----|-----|-----|-----|-----|-----|-----|
|     | 50  |     |     |     |     | 55  |     |     |     |

( 2 ) INFORMATION FOR SEQ ID NO: 87:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 87:

| Arg | Pro | Asp | Phe | Cys | Leu | Glu | Pro | Pro | Tyr | Glu | Gly | Phe | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |

| Leu | His | Thr | Arg | Tyr | Phe | Tyr | Asn | Ala | Lys | Ala | Gly | Leu | Cys | Gln | Thr |
|-----|-----|-----|-----|-----|-----|-----|-----|-----|-----|-----|-----|-----|-----|-----|-----|

```
                        2 0                     2 5                         3 0
Phe  Tyr  Tyr  Gly  Gly  Cys  His  Ala  Lys  Arg  Asn  Asn  Phe  Glu  Ser  Ala
              3 5                   4 0                   4 5

Glu  Asp  Cys  Met  Arg  Thr  Cys  Gly  Gly  Ala
     5 0                      5 5
```

( 2 ) INFORMATION FOR SEQ ID NO: 88:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 88:

```
Arg  Pro  Asp  Phe  Cys  Leu  Glu  Pro  Pro  Tyr  Glu  Gly  Ala  Cys  Arg  Ala
              5                    1 0                   1 5

Leu  His  Leu  Arg  Tyr  Phe  Tyr  Asn  Ala  Lys  Ala  Gly  Leu  Cys  Gln  Thr
              2 0                   2 5                   3 0

Phe  Tyr  Tyr  Gly  Gly  Cys  Tyr  Ala  Lys  Arg  Asn  Asn  Phe  Glu  Ser  Ala
              3 5                   4 0                   4 5

Glu  Asp  Cys  Met  Arg  Thr  Cys  Gly  Gly  Ala
     5 0                      5 5
```

( 2 ) INFORMATION FOR SEQ ID NO: 89:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 89:

```
Arg  Pro  Asp  Phe  Cys  Leu  Glu  Pro  Pro  Tyr  Asp  Gly  Pro  Cys  Arg  Ala
              5                    1 0                   1 5

Leu  His  Leu  Arg  Tyr  Phe  Tyr  Asn  Ala  Lys  Ala  Gly  Leu  Cys  Gln  Thr
              2 0                   2 5                   3 0

Phe  Tyr  Tyr  Gly  Gly  Cys  Leu  Ala  Lys  Arg  Asn  Asn  Phe  Glu  Ser  Ala
              3 5                   4 0                   4 5

Glu  Asp  Cys  Met  Arg  Thr  Cys  Gly  Gly  Ala
     5 0                      5 5
```

( 2 ) INFORMATION FOR SEQ ID NO: 90:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 90:

```
Arg  Pro  Asp  Phe  Cys  Leu  Glu  Pro  Pro  Tyr  Glu  Gly  Tyr  Cys  Arg  Ala
              5                    1 0                   1 5

Leu  His  Ile  Arg  Tyr  Phe  Tyr  Asn  Ala  Lys  Ala  Gly  Leu  Cys  Gln  Thr
              2 0                   2 5                   3 0

Phe  Tyr  Tyr  Gly  Gly  Cys  His  Ala  Lys  Arg  Asn  Asn  Phe  Glu  Ser  Ala
              3 5                   4 0                   4 5
```

Glu Asp Cys Met Arg Thr Cys Gly Gly Ala
50                      55

( 2 ) INFORMATION FOR SEQ ID NO: 91:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 91:

Arg Pro Asp Phe Cys Leu Glu Pro Pro Tyr Pro Gly Tyr Cys Arg Ala
                5                   10                  15

Leu His Leu Arg Tyr Phe Tyr Asn Ala Lys Ala Gly Leu Cys Gln Thr
            20                  25                  30

Phe Thr Tyr Gly Gly Cys His Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 92:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 92:

Arg Pro Asp Phe Cys Leu Glu Pro Pro Tyr Asp Gly Pro Cys Arg Ala
                5                   10                  15

Leu His Pro Arg Tyr Phe Tyr Asn Ala Lys Ala Gly Leu Cys Gln Thr
            20                  25                  30

Phe Trp Tyr Gly Gly Cys Tyr Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 93:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 93:

Arg Pro Asp Phe Cys Leu Glu Pro Pro Tyr Asp Gly Pro Cys Arg Ala
                5                   10                  15

Leu His Pro Arg Tyr Phe Tyr Asn Ala Lys Ala Gly Leu Cys Gln Thr
            20                  25                  30

Phe Trp Tyr Gly Gly Cys Leu Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 94:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 94:

Arg Pro Asp Phe Cys Leu Glu Pro Pro Tyr Asp Gly Pro Cys Arg Ala
              5                   10                  15
Leu His His Arg Tyr Phe Tyr Asn Ala Lys Ala Gly Leu Cys Gln Thr
            20                  25                  30
Phe Tyr Tyr Gly Gly Cys Arg Ala Lys Arg Asn Asn Phe Glu Ser Ala
        35                  40                  45
Glu Asp Cys Met Arg Thr Cys Gly Gly Ala
    50                  55

(2) INFORMATION FOR SEQ ID NO: 95:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 95:

Arg Pro Asp Phe Cys Leu Glu Pro Pro Tyr Glu Gly Trp Cys Arg Ala
              5                   10                  15
Leu His His Arg Tyr Phe Tyr Asn Ala Lys Ala Gly Leu Cys Gln Thr
            20                  25                  30
Phe Ile Tyr Gly Gly Cys Gly Ala Lys Arg Asn Asn Phe Glu Ser Ala
        35                  40                  45
Glu Asp Cys Met Arg Thr Cys Gly Gly Ala
    50                  55

(2) INFORMATION FOR SEQ ID NO: 96:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 96:

Arg Pro Asp Phe Cys Leu Glu Pro Pro Tyr Thr Gly Pro Cys Arg Ala
              5                   10                  15
Leu His His Arg Tyr Phe Tyr Asn Ala Lys Ala Gly Leu Cys Gln Thr
            20                  25                  30
Phe Phe Tyr Gly Gly Cys Phe Ala Lys Arg Asn Asn Phe Glu Ser Ala
        35                  40                  45
Glu Asp Cys Met Arg Thr Cys Gly Gly Ala
    50                  55

(2) INFORMATION FOR SEQ ID NO: 97:

(i) SEQUENCE CHARACTERISTICS:
  (A) LENGTH: 58 amino acids
  (B) TYPE: amino acid
  (C) STRANDEDNESS: single (D) TOPOLOGY: linear (ii) MOLECULE TYPE: peptide (xi) SEQUENCE DESCRIPTION: SEQ ID NO: 97:

| Arg | Pro | Asp | Phe | Cys | Leu | Glu | Pro | Pro | Tyr | Ser | Gly | Leu | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     |     | 30  |     |
| Phe | Tyr | Tyr | Gly | Gly | Cys | Tyr | Ala | Lys | Arg | Asn | Asn | Phe | Glu | Ser | Ala |
|     |     | 35  |     |     |     |     | 40  |     |     |     |     |     |     | 45  |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 98:

(i) SEQUENCE CHARACTERISTICS:
   (A) LENGTH: 58 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO: 98:

| Arg | Pro | Asp | Phe | Cys | Leu | Glu | Pro | Pro | Tyr | Pro | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     |     | 30  |     |
| Phe | His | Tyr | Gly | Gly | Cys | Phe | Ala | Lys | Arg | Asn | Asn | Phe | Glu | Ser | Ala |
|     |     | 35  |     |     |     |     | 40  |     |     |     |     |     |     | 45  |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 99:

(i) SEQUENCE CHARACTERISTICS:
   (A) LENGTH: 58 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO: 99:

| Arg | Pro | Asp | Phe | Cys | Leu | Glu | Pro | Pro | Tyr | Ser | Gly | Leu | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     |     | 30  |     |
| Phe | Tyr | Tyr | Gly | Gly | Cys | Phe | Ala | Lys | Arg | Asn | Asn | Phe | Glu | Ser | Ala |
|     |     | 35  |     |     |     |     | 40  |     |     |     |     |     |     | 45  |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 100:

(i) SEQUENCE CHARACTERISTICS:
   (A) LENGTH: 58 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO: 100:

Arg Pro Asp Phe Cys Leu Glu Pro Pro Tyr Pro Gly Ile Cys Arg Ala
            5                  10                 15

Leu His Lys Arg Tyr Phe Tyr Asn Ala Lys Ala Gly Leu Cys Gln Thr
            20                 25                 30

Phe Tyr Tyr Gly Gly Cys Met Ala Lys Arg Asn Asn Phe Glu Ser Ala
            35              40              45

Glu Asp Cys Met Arg Thr Cys Gly Gly Ala
            50              55

(2) INFORMATION FOR SEQ ID NO: 101:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 101:

Arg Pro Asp Phe Cys Leu Glu Pro Pro Tyr Glu Gly Met Cys Arg Ala
            5                  10                 15

Ile His Lys Arg Tyr Phe Tyr Asn Ala Lys Ala Gly Leu Cys Gln Thr
            20                 25                 30

Phe Thr Tyr Gly Gly Cys Met Ala Lys Arg Asn Asn Phe Glu Ser Ala
            35              40              45

Glu Asp Cys Met Arg Thr Cys Gly Gly Ala
            50              55

(2) INFORMATION FOR SEQ ID NO: 102:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 102:

Arg Pro Asp Phe Cys Leu Glu Pro Pro Tyr Pro Gly Val Cys Arg Ala
            5                  10                 15

Leu His Lys Arg Tyr Phe Tyr Asn Ala Lys Ala Gly Leu Cys Gln Thr
            20                 25                 30

Phe Ser Tyr Gly Gly Cys Gln Ala Lys Arg Asn Asn Phe Glu Ser Ala
            35              40              45

Glu Asp Cys Met Arg Thr Cys Gly Gly Ala
            50              55

(2) INFORMATION FOR SEQ ID NO: 103:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 103:

Arg Pro Asp Phe Cys Leu Glu Pro Pro Tyr Glu Gly Leu Cys Arg Ala
            5                  10                 15

Leu His Lys Arg Tyr Phe Tyr Asn Ala Lys Ala Gly Leu Cys Gln Thr

|  | 20 | 25 | 30 |
| --- | --- | --- | --- |

Phe Tyr Tyr Gly Gly Cys Phe Ala Lys Arg Asn Asn Phe Glu Ser Ala
        35                  40                  45

Glu Asp Cys Met Arg Thr Cys Gly Gly Ala
 50                       55

( 2 ) INFORMATION FOR SEQ ID NO: 104:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 104:

Arg Pro Asp Phe Cys Leu Glu Pro Pro Tyr Pro Gly Leu Cys Arg Ala
                 5                  10                  15

Leu His Lys Arg Tyr Phe Tyr Asn Ala Lys Ala Gly Leu Cys Gln Thr
            20                  25                  30

Phe Tyr Tyr Gly Gly Cys Tyr Ala Lys Arg Asn Asn Phe Glu Ser Ala
        35                  40                  45

Glu Asp Cys Met Arg Thr Cys Gly Gly Ala
 50                       55

( 2 ) INFORMATION FOR SEQ ID NO: 105:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 105:

Arg Pro Asp Phe Cys Leu Glu Pro Pro Tyr Asp Gly Pro Cys Arg Ala
                 5                  10                  15

Leu His Gln Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35                  40                  45

Glu Asp Cys Met Arg Thr Cys Gly Gly Ala
 50                       55

( 2 ) INFORMATION FOR SEQ ID NO: 106:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 106:

Arg Pro Asp Phe Cys Leu Glu Pro Ala Tyr Asp Gly Pro Cys Arg Ala
                 5                  10                  15

Leu His Gln Arg Tyr Leu Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 107:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 107:

Arg Pro Asp Phe Cys Leu Glu Pro Pro Tyr Asp Gly Pro Cys Arg Ala
                5                   10                  15

Leu His Gln Arg Tyr Phe Tyr Asn Ala Lys Ala Gly Leu Cys Gln Thr
            20                  25                  30

Phe Thr Tyr Gly Gly Cys Arg Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 108:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 108:

Arg Pro Asp Phe Cys Leu Glu Pro Pro Tyr Asp Gly Pro Cys Arg Ala
                5                   10                  15

Leu His Leu Arg Tyr Phe Tyr Asn Ala Lys Ala Gly Leu Cys Gln Thr
            20                  25                  30

Phe Tyr Tyr Gly Gly Cys Leu Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 109:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 109:

Arg Pro Asp Phe Cys Leu Glu Pro Pro Tyr Glu Gly Tyr Cys Arg Ala
                5                   10                  15

Leu His Ile Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
        35                  40                  45

Glu Asp Cys Met Arg Thr Cys Gly Gly Ala
50                      55

( 2 ) INFORMATION FOR SEQ ID NO: 110:

(i) SEQUENCE CHARACTERISTICS:
 (A) LENGTH: 58 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO: 110:

| Arg | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
| | | | | 5 | | | | | 10 | | | | | 15 | |
| Leu | His | Pro | Arg | Tyr | Phe | Tyr | Asn | Ala | Lys | Ala | Gly | Leu | Cys | Gln | Thr |
| | | | 20 | | | | 25 | | | | | | 30 | | |
| Phe | Trp | Tyr | Gly | Gly | Cys | Leu | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 111:

(i) SEQUENCE CHARACTERISTICS:
 (A) LENGTH: 58 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO: 111:

| Arg | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
| | | | | 5 | | | | | 10 | | | | | 15 | |
| Leu | His | Pro | Arg | Tyr | Phe | Tyr | Asn | Ala | Lys | Ala | Gly | Leu | Cys | Gln | Thr |
| | | | 20 | | | | 25 | | | | | | 30 | | |
| Phe | Trp | Tyr | Gly | Gly | Cys | Leu | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 112:

(i) SEQUENCE CHARACTERISTICS:
 (A) LENGTH: 58 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO: 112:

| Arg | Pro | Asp | Phe | Cys | Leu | Glu | Pro | Pro | Tyr | Asp | Gly | Pro | Cys | Arg | Ala |
|-----|-----|-----|-----|-----|-----|-----|-----|-----|-----|-----|-----|-----|-----|-----|-----|
| | | | | 5 | | | | | 10 | | | | | 15 | |
| Leu | His | His | Arg | Tyr | Phe | Tyr | Asn | Ala | Lys | Ala | Gly | Leu | Cys | Gln | Thr |
| | | | 20 | | | | 25 | | | | | | 30 | | |
| Phe | Tyr | Tyr | Gly | Gly | Cys | Arg | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 113:

(i) SEQUENCE CHARACTERISTICS:
 (A) LENGTH: 58 amino acids
 (B) TYPE: amino acid
 (C) STRANDEDNESS: single ( D ) TOPOLOGY: linear ( i i ) MOLECULE TYPE: peptide ( x i ) SEQUENCE DESCRIPTION: SEQ ID NO: 113:

Arg Pro Asp Phe Cys Leu Glu Pro Pro Tyr Ser Gly Leu Cys Arg Ala
                5                   10                      15

Leu His Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
            35              40                  45

Glu Asp Cys Met Arg Thr Cys Gly Gly Ala
    50                  55

( 2 ) INFORMATION FOR SEQ ID NO: 114:

( i ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO: 114:

Arg Pro Asp Phe Cys Leu Glu Pro Pro Tyr Glu Gly Leu Cys Arg Ala
                5                   10                      15

Leu His Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
            35              40                  45

Glu Asp Cys Met Arg Thr Cys Gly Gly Ala
    50                  55

( 2 ) INFORMATION FOR SEQ ID NO: 115:

( i ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO: 115:

Arg Pro Asp Phe Cys Leu Glu Pro Ala Tyr Asp Gly Pro Cys Arg Ala
                5                   10                      15

Leu His Gln Arg Tyr Leu Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35              40                  45

Glu Asp Cys Met Arg Thr Cys Gly Gly Ala
    50                  55

( 2 ) INFORMATION FOR SEQ ID NO: 116:

( i ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO: 116:

Ala Pro Asp Phe Cys Leu Glu Pro Pro Tyr Asp Gly Pro Cys Arg Ala
                    5                   10                  15

Ile Ile Lys Arg Tyr Phe Tyr Asn Ala Lys Ala Gly Leu Cys Gln Thr
                20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
        50                  55

( 2 ) INFORMATION FOR SEQ ID NO: 117:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 117:

Ala Pro Asp Phe Cys Leu Glu Pro Pro Tyr Asp Gly Pro Cys Lys Ala
                    5                   10                  15

Ile Ile Lys Arg Tyr Phe Tyr Asn Ala Lys Ala Gly Leu Cys Gln Thr
                20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
        50                  55

( 2 ) INFORMATION FOR SEQ ID NO: 118:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 118:

Ala Pro Asp Phe Cys Leu Glu Pro Pro Tyr Asp Gly Pro Cys Lys Ala
                    5                   10                  15

Ile Ile Lys Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
        50                  55

( 2 ) INFORMATION FOR SEQ ID NO: 119:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 119:

Ala Pro Asp Phe Cys Leu Glu Pro Pro Tyr Thr Gly Pro Cys Arg Ala
                    5                   10                  15

Tyr Ile Thr Arg Tyr Phe Tyr Asn Ala Lys Ala Gly Leu Cys Gln Thr

```
                         20                      25                          30
Phe  Val  Tyr  Gly  Gly  Cys  Phe  Ala  Lys  Arg  Asn  Asn  Phe  Glu  Ser  Ala
               35                      40                      45

Glu  Asp  Cys  Met  Arg  Thr  Cys  Gly  Gly  Ala
               50                      55
```

( 2 ) INFORMATION FOR SEQ ID NO: 120:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 120:

```
Ala  Pro  Asp  Phe  Cys  Leu  Glu  Pro  Pro  Tyr  Thr  Gly  Pro  Cys  Arg  Ala
                    5                      10                     15

Tyr  Ile  Thr  Arg  Tyr  Phe  Tyr  Asn  Ala  Lys  Ala  Gly  Leu  Cys  Gln  Thr
               20                      25                      30

Phe  Val  Tyr  Gly  Gly  Cys  Phe  Ala  Lys  Arg  Asn  Asn  Phe  Lys  Ser  Ala
               35                      40                      45

Glu  Asp  Cys  Met  Arg  Thr  Cys  Gly  Gly  Ala
               50                      55
```

( 2 ) INFORMATION FOR SEQ ID NO: 121:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 121:

```
Ala  Pro  Asp  Phe  Cys  Leu  Glu  Pro  Pro  Tyr  Thr  Gly  Pro  Cys  Arg  Ala
                    5                      10                     15

Tyr  Ile  Thr  Arg  Tyr  Phe  Tyr  Asn  Ala  Lys  Ala  Gly  Leu  Cys  Gln  Thr
               20                      25                      30

Phe  Val  Tyr  Gly  Gly  Cys  Arg  Ala  Lys  Arg  Asn  Asn  Phe  Lys  Ser  Ala
               35                      40                      45

Glu  Asp  Cys  Met  Arg  Thr  Cys  Gly  Gly  Ala
               50                      55
```

( 2 ) INFORMATION FOR SEQ ID NO: 122:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 122:

```
Ala  Pro  Asp  Phe  Cys  Leu  Glu  Pro  Pro  Tyr  Thr  Gly  Pro  Cys  Arg  Ala
                    5                      10                     15

Tyr  Ile  Thr  Arg  Tyr  Phe  Tyr  Asn  Ala  Lys  Ala  Gly  Leu  Cys  Gln  Thr
               20                      25                      30

Phe  Val  Tyr  Gly  Gly  Cys  Arg  Ala  Lys  Arg  Asn  Asn  Phe  Lys  Ser  Ala
               35                      40                      45
```

```
Glu Asp Cys Met Arg Thr Cys Gly Gly Ala
    50                  55
```

( 2 ) INFORMATION FOR SEQ ID NO: 123:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 123:

```
Ala Pro Asp Phe Cys Leu Glu Pro Pro Tyr Thr Gly Ile Cys Arg Ala
                5                   10                  15
Tyr Ile Thr Arg Tyr Phe Tyr Asn Ala Lys Ala Gly Leu Cys Gln Thr
            20                  25                  30
Phe Val Tyr Gly Gly Cys Arg Ala Lys Arg Asn Asn Phe Lys Ser Ala
        35                  40                  45
Glu Asp Cys Met Arg Thr Cys Gly Gly Ala
    50                  55
```

( 2 ) INFORMATION FOR SEQ ID NO: 124:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 124:

```
Ala Pro Asp Phe Cys Leu Glu Pro Pro Tyr Glu Gly Pro Cys Arg Ala
                5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 125:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 125:

```
Ala Pro Asp Phe Cys Leu Glu Pro Pro Tyr Thr Gly Pro Cys Arg Ala
                5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 126:

( i ) SEQUENCE CHARACTERISTICS:
   ( A ) LENGTH: 58 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO: 126:

Ala Pro Asp Phe Cys Leu Glu Pro Pro Tyr Thr Gly Pro Cys Arg Ala
              5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Lys Ser Ala
        35                  40                  45
Glu Asp Cys Met Arg Thr Cys Gly Gly Ala
50                      55

( 2 ) INFORMATION FOR SEQ ID NO: 127:

( i ) SEQUENCE CHARACTERISTICS:
      ( A ) LENGTH: 24
      ( B ) TYPE: nucleic acid
      ( C ) STRANDEDNESS: single
      ( D ) TOPOLOGY: linear ( x i ) SEQUENCE DESCRIPTION: SEQ ID NO: 127:

GCTTAATAAT AGCCCGGCAG GGGC                                    2 4

( 2 ) INFORMATION FOR SEQ ID NO: 128:

( i ) SEQUENCE CHARACTERISTICS:
      ( A ) LENGTH: 48
      ( B ) TYPE: nucleic acid
      ( C ) STRANDEDNESS: single
      ( D ) TOPOLOGY: linear ( x i ) SEQUENCE DESCRIPTION: SEQ ID NO: 128:

GTAGAAGTAG CGCTTAATAA TAGCCTTGCA GGGGCCGTCA TACGGTGG           4 8

( 2 ) INFORMATION FOR SEQ ID NO: 129:

( i ) SEQUENCE CHARACTERISTICS:
      ( A ) LENGTH: 24
      ( B ) TYPE: nucleic acid
      ( C ) STRANDEDNESS: single
      ( D ) TOPOLOGY: linear ( x i ) SEQUENCE DESCRIPTION: SEQ ID NO: 129:

CCTCGGCCGA TTCGAAATTG TTAC                                    2 4

( 2 ) INFORMATION FOR SEQ ID NO: 130:

( i ) SEQUENCE CHARACTERISTICS:
      ( A ) LENGTH: 30
      ( B ) TYPE: nucleic acid
      ( C ) STRANDEDNESS: single
      ( D ) TOPOLOGY: linear ( x i ) SEQUENCE DESCRIPTION: SEQ ID NO: 130:

GTTACGCTTA GCAAAGCAGC CACCATATAC                              3 0

( 2 ) INFORMATION FOR SEQ ID NO: 131:

( i ) SEQUENCE CHARACTERISTICS:
      ( A ) LENGTH: 36

( B ) TYPE: nucleic acid
( C ) STRANDEDNESS: single
( D ) TOPOLOGY: linear ( x i ) SEQUENCE DESCRIPTION: SEQ ID NO: 131:

CTTGAAATTG TTACGCTTAA GCCACCATAT ACAAAG 36

( 2 ) INFORMATION FOR SEQ ID NO: 132:

( i ) SEQUENCE CHARACTERISTICS:
( A ) LENGTH: 23
( B ) TYPE: nucleic acid
( C ) STRANDEDNESS: single
( D ) TOPOLOGY: linear ( x i ) SEQUENCE DESCRIPTION: SEQ ID NO: 132:

GCCCGGCATG GGCCGGTATA CGG 23

( 2 ) INFORMATION FOR SEQ ID NO: 133:

( i ) SEQUENCE CHARACTERISTICS:
( A ) LENGTH: 42
( B ) TYPE: nucleic acid
( C ) STRANDEDNESS: single
( D ) TOPOLOGY: linear ( x i ) SEQUENCE DESCRIPTION: SEQ ID NO: 133:

GAAGTAGCGG GTAATATAAG CCCGGCATAT GCCGGTATAC GG 42

( 2 ) INFORMATION FOR SEQ ID NO: 134:

( i ) SEQUENCE CHARACTERISTICS:
( A ) LENGTH: 21
( B ) TYPE: nucleic acid
( C ) STRANDEDNESS: single
( D ) TOPOLOGY: linear ( x i ) SEQUENCE DESCRIPTION: SEQ ID NO: 134:

GCAGGGCCC TCATACGGTG G 21

( 2 ) INFORMATION FOR SEQ ID NO: 135:

( i ) SEQUENCE CHARACTERISTICS:
( A ) LENGTH: 30
( B ) TYPE: nucleic acid
( C ) STRANDEDNESS: single
( D ) TOPOLOGY: linear ( i x ) FEATURE:
( D ) OTHER INFORMATION: M is either of A or C; N is either
of A, G, C or T.

( x i ) SEQUENCE DESCRIPTION: SEQ ID NO: 135:

GTTACGCTTA GCMTNGCAGC CACCATATAC 30

( 2 ) INFORMATION FOR SEQ ID NO: 136:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 136:

Ala Pro Asp Phe Cys Leu Glu Pro Pro Tyr Asp Gly Pro Cys Lys Ala
            5                   10                  15

Ile Ile Lys Arg Tyr Phe Tyr Asn Ala Lys Ala Gly Leu Cys Gln Thr
            20                  25                  30

Phe Val Tyr Gly Gly Cys Glu Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 137:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 137:

Ala Pro Asp Phe Cys Leu Glu Pro Pro Tyr Glu Gly Pro Cys Lys Ala
                5                   10                  15

Ile Ile Lys Arg Tyr Phe Tyr Asn Ala Lys Ala Gly Leu Cys Gln Thr
            20                  25                  30

Phe Val Tyr Gly Gly Cys Glu Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 138:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 138:

Ala Pro Asp Phe Cys Leu Glu Pro Pro Tyr Asp Gly Pro Cys Arg Ala
                5                   10                  15

Ile Ile Lys Arg Tyr Phe Tyr Asn Ala Lys Ala Gly Leu Cys Gln Thr
            20                  25                  30

Phe Val Tyr Gly Gly Cys Glu Ala Lys Arg Asn Asn Phe Glu Ser Ala
        35                  40                  45

Glu Asp Cys Met Arg Thr Cys Gly Gly Ala
    50                  55

(2) INFORMATION FOR SEQ ID NO: 139:

(i) SEQUENCE CHARACTERISTICS:
  (A) LENGTH: 58 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 139:

Ala Pro Asp Phe Cys Leu Glu Pro Pro Tyr Asp Gly Pro Cys Arg Ala
                5                   10                  15

Ile Ile Lys Arg Tyr Phe Tyr Asn Ala Lys Ala Gly Leu Cys Gln Thr
            20                  25                  30

Phe Asp Tyr Gly Gly Cys Leu Ala Lys Arg Asn Asn Phe Lys Ser Ala
        35                  40                  45

```
Glu  Asp  Cys  Met  Arg  Thr  Cys  Gly  Gly  Ala
     50                      55
```

( 2 ) INFORMATION FOR SEQ ID NO: 140:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 140:

```
Ala  Pro  Asp  Phe  Cys  Leu  Glu  Pro  Pro  Tyr  Thr  Gly  Pro  Cys  Arg  Ala
               5                        10                       15
Tyr  Ile  Thr  Arg  Tyr  Phe  Tyr  Asn  Ala  Lys  Ala  Gly  Leu  Cys  Gln  Thr
               20                       25                       30
Phe  Val  Tyr  Gly  Gly  Cys  Phe  Ala  Lys  Arg  Asn  Asn  Phe  Glu  Ser  Ala
               35                       40                       45
Glu  Asp  Cys  Met  Arg  Thr  Cys  Gly  Gly  Ala
     50                      55
```

( 2 ) INFORMATION FOR SEQ ID NO: 141:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 141:

```
Ala  Pro  Asp  Phe  Cys  Leu  Glu  Pro  Pro  Tyr  Asp  Gly  Pro  Cys  Lys  Ala
               5                        10                       15
Ile  Ile  Lys  Arg  Tyr  Phe  Tyr  Asn  Ala  Lys  Ala  Gly  Leu  Cys  Gln  Thr
               20                       25                       30
Phe  Val  Tyr  Gly  Gly  Cys  Phe  Ala  Lys  Arg  Asn  Asn  Phe  Glu  Ser  Ala
               35                       40                       45
Glu  Asp  Cys  Met  Arg  Thr  Cys  Gly  Gly  Ala
     50                      55
```

( 2 ) INFORMATION FOR SEQ ID NO: 142:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 142:

```
Ala  Pro  Asp  Phe  Cys  Leu  Glu  Pro  Pro  Tyr  Asp  Gly  Pro  Cys  Lys  Ala
               5                        10                       15
Ile  Ile  Lys  Arg  Tyr  Phe  Tyr  Asn  Ala  Lys  Ala  Gly  Leu  Cys  Gln  Thr
               20                       25                       30
Phe  Val  Tyr  Gly  Gly  Cys  Tyr  Ala  Lys  Arg  Asn  Asn  Phe  Glu  Ser  Ala
               35                       40                       45
Glu  Asp  Cys  Met  Arg  Thr  Cys  Gly  Gly  Ala
     50                      55
```

( 2 ) INFORMATION FOR SEQ ID NO: 143:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 143:

Ala Pro Asp Phe Cys Leu Glu Pro Pro Tyr Asp Gly Pro Cys Arg Ala
            5                      10               15

Ile Ile Lys Arg Tyr Phe Tyr Asn Ala Lys Ala Gly Leu Cys Gln Thr
         20                 25                 30

Phe Val Tyr Gly Gly Cys Phe Ala Lys Arg Asn Asn Phe Glu Ser Ala
       35                40                 45

Glu Asp Cys Met Arg Thr Cys Gly Gly Ala
 50                 55

( 2 ) INFORMATION FOR SEQ ID NO: 144:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 144:

Ala Pro Asp Phe Cys Leu Glu Pro Pro Tyr Asp Gly Pro Cys Arg Ala
            5                      10               15

Ile Ile Lys Arg Tyr Phe Tyr Asn Ala Lys Ala Gly Leu Cys Gln Thr
         20                 25                 30

Phe Val Tyr Gly Gly Cys Tyr Ala Lys Arg Asn Asn Phe Glu Ser Ala
       35                40                 45

Glu Asp Cys Met Arg Thr Cys Gly Gly Ala
 50                 55

( 2 ) INFORMATION FOR SEQ ID NO: 145:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 145:

Ala Pro Asp Phe Cys Leu Glu Pro Pro Tyr Thr Gly Pro Cys Arg Ala
            5                      10               15

Ile Ile Lys Arg Tyr Phe Tyr Asn Ala Lys Ala Gly Leu Cys Gln Thr
         20                 25                 30

Phe Val Tyr Gly Gly Cys Phe Ala Lys Arg Asn Asn Phe Glu Ser Ala
       35                40                 45

Glu Asp Cys Met Arg Thr Cys Gly Gly Ala
 50                 55

( 2 ) INFORMATION FOR SEQ ID NO: 146:

( i ) SEQUENCE CHARACTERISTICS:
        ( A ) LENGTH: 58 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO: 146:

Ala Pro Asp Phe Cys Leu Glu Pro Pro Tyr Thr Gly Pro Cys Arg Ala
                  5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Tyr Ser Ala
            35                  40                  45
Glu Asp Cys Met Arg Thr Cys Gly Gly Ala
        50                  55

( 2 ) INFORMATION FOR SEQ ID NO: 147:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 147:

Ala Pro Asp Phe Cys Leu Glu Pro Pro Tyr Glu Gly Pro Cys Arg Ala
                  5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Glu Ser Ala
            35                  40                  45
Glu Asp Cys Met Arg Thr Cys Gly Gly Ala
        50                  55

( 2 ) INFORMATION FOR SEQ ID NO: 148:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 148:

Ala Pro Asp Phe Cys Leu Glu Pro Pro Tyr Thr Gly Pro Cys Arg Ala
                  5                   10                  15
Met His His Arg Tyr Phe Tyr Asn Ala Lys Ala Gly Leu Cys Gln Thr
            20                  25                  30
Phe Val Tyr Gly Gly Cys Phe Ala Lys Arg Asn Asn Phe Glu Ser Ala
            35                  40                  45
Glu Asp Cys Met Arg Thr Cys Gly Gly Ala
        50                  55

( 2 ) INFORMATION FOR SEQ ID NO: 149:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 149:

Arg Pro Asp Phe Cys Leu Glu Pro Pro Tyr Asp Gly Pro Cys Arg Ala
                  5                   10                      15

Leu His Gln Arg Tyr Phe Tyr Asn Ala Lys Ala Gly Leu Cys Gln Thr
              20                  25                  30

Phe Thr Tyr Gly Gly Cys Arg Ala Lys Arg Asn Asn Phe Glu Ser Ala
              35              40                  45

Glu Asp Cys Met Arg Thr Cys Gly Gly Ala
        50              55

( 2 ) INFORMATION FOR SEQ ID NO: 150:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 150:

Arg Pro Asp Phe Cys Leu Glu Pro Pro Tyr Asp Gly Pro Cys Arg Ala
                  5                   10                      15

Leu His Leu Arg Tyr Phe Tyr Asn Ala Lys Ala Gly Leu Cys Gln Thr
              20                  25                  30

Phe Tyr Tyr Gly Gly Cys Leu Ala Lys Arg Asn Asn Phe Glu Ser Ala
              35              40                  45

Glu Asp Cys Met Arg Thr Cys Gly Gly Ala
        50              55

( 2 ) INFORMATION FOR SEQ ID NO: 151:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 151:

Arg Pro Asp Phe Cys Leu Glu Pro Pro Tyr Glu Gly Tyr Cys Arg Ala
                  5                   10                      15

Leu His Ile Arg Tyr Phe Tyr Asn Ala Lys Ala Gly Leu Cys Gln Thr
              20                  25                  30

Phe Tyr Tyr Gly Gly Cys His Ala Lys Arg Asn Asn Phe Glu Ser Ala
              35              40                  45

Glu Asp Cys Met Arg Thr Cys Gly Gly Ala
        50              55

( 2 ) INFORMATION FOR SEQ ID NO: 152:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 152:

Arg Pro Asp Phe Cys Leu Glu Pro Pro Tyr Asp Gly Pro Cys Arg Ala
                  5                   10                      15

| Leu | His | Pro | Arg<br>20 | Tyr | Phe | Tyr | Asn | Ala<br>25 | Lys | Ala | Gly | Leu | Cys<br>30 | Gln | Thr |
| Phe | Trp | Tyr<br>35 | Gly | Gly | Cys | Tyr | Ala<br>40 | Lys | Arg | Asn | Asn | Phe<br>45 | Glu | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 153:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 153:

| Arg | Pro | Asp | Phe | Cys<br>5 | Leu | Glu | Pro | Pro | Tyr<br>10 | Asp | Gly | Pro | Cys | Arg<br>15 | Ala |
| Leu | His | Pro | Arg<br>20 | Tyr | Phe | Tyr | Asn | Ala<br>25 | Lys | Ala | Gly | Leu | Cys<br>30 | Gln | Thr |
| Phe | Trp | Tyr<br>35 | Gly | Gly | Cys | Leu | Ala<br>40 | Lys | Arg | Asn | Asn | Phe<br>45 | Glu | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 154:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 154:

| Arg | Pro | Asp | Phe | Cys<br>5 | Leu | Glu | Pro | Pro | Tyr<br>10 | Asp | Gly | Pro | Cys | Arg<br>15 | Ala |
| Leu | His | His | Arg<br>20 | Tyr | Phe | Tyr | Asn | Ala<br>25 | Lys | Ala | Gly | Leu | Cys<br>30 | Gln | Thr |
| Phe | Tyr | Tyr<br>35 | Gly | Gly | Cys | Arg | Ala<br>40 | Lys | Arg | Asn | Asn | Phe<br>45 | Glu | Ser | Ala |
| Glu | Asp<br>50 | Cys | Met | Arg | Thr | Cys<br>55 | Gly | Gly | Ala | | | | | | |

( 2 ) INFORMATION FOR SEQ ID NO: 155:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 155:

| Arg | Pro | Asp | Phe | Cys<br>5 | Leu | Glu | Pro | Pro | Tyr<br>10 | Ser | Gly | Leu | Cys | Arg<br>15 | Ala |
| Leu | His | Lys | Arg<br>20 | Tyr | Phe | Tyr | Asn | Ala<br>25 | Lys | Ala | Gly | Leu | Cys<br>30 | Gln | Thr |
| Phe | Tyr | Tyr<br>35 | Gly | Gly | Cys | Phe | Ala<br>40 | Lys | Arg | Asn | Asn | Phe<br>45 | Glu | Ser | Ala |

Glu Asp Cys Met Arg Thr Cys Gly Gly Ala
    50                  55

( 2 ) INFORMATION FOR SEQ ID NO: 156:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 156:

Arg Pro Asp Phe Cys Leu Glu Pro Pro Tyr Glu Gly Leu Cys Arg Ala
                5                   10                  15
Leu His Lys Arg Tyr Phe Tyr Asn Ala Lys Ala Gly Leu Cys Gln Thr
            20                  25                  30
Phe Tyr Tyr Gly Gly Cys Phe Ala Lys Arg Asn Asn Phe Glu Ser Ala
        35                  40                  45
Glu Asp Cys Met Arg Thr Cys Gly Gly Ala
    50                  55

( 2 ) INFORMATION FOR SEQ ID NO: 157:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 157:

Arg Pro Asp Phe Cys Leu Glu Pro Ala Tyr Asp Gly Pro Cys Arg Ala
                5                   10                  15
Leu His Gln Arg Tyr Leu Tyr Asn Ala Lys Ala Gly Leu Cys Gln Thr
            20                  25                  30
Phe Val Tyr Gly Gly Cys Phe Ala Lys Arg Asn Asn Phe Glu Ser Ala
        35                  40                  45
Glu Asp Cys Met Arg Thr Cys Gly Gly Ala
    50                  55

( 2 ) INFORMATION FOR SEQ ID NO: 158:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 158:

CACTCCGCTC CGGACACTAG TGGTGGCGCC GCTGAA                     36

( 2 ) INFORMATION FOR SEQ ID NO: 159:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 159:

His Ser Ala Pro Asp
        5

( 2 ) INFORMATION FOR SEQ ID NO: 160:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 160:

Gly Gly Ala Ala Glu
        5

( 2 ) INFORMATION FOR SEQ ID NO: 161:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 161:

GTTACGCTTT GCCCTGCAGC CACC                                    24

( 2 ) INFORMATION FOR SEQ ID NO: 162:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 162:

GCCTTGCAGG GGCCCGGTAT ACGGTGG                            27

( 2 ) INFORMATION FOR SEQ ID NO: 163:

( i ) SEQUENCE CHARACTERISTICS:
        ( A ) LENGTH: 63
        ( B ) TYPE: nucleic acid
        ( C ) STRANDEDNESS: single
        ( D ) TOPOLOGY: linear ( i x ) FEATURE:
        ( D ) OTHER INFORMATION: R is an equimolar mixture of A and
            G; N is either of G, A, T and C; and K is
            either G and T.

( x i ) SEQUENCE DESCRIPTION: SEQ ID NO: 163:

TATACCGGGC CCTGCARGNN KNNKNNKNNK NNKTACTTCT ACAACGCCAA GGCCGGACTC      60

TGT                                                                                                              63

( 2 ) INFORMATION FOR SEQ ID NO: 164:

( i ) SEQUENCE CHARACTERISTICS:
        ( A ) LENGTH: 63
        ( B ) TYPE: nucleic acid
        ( C ) STRANDEDNESS: single
        ( D ) TOPOLOGY: linear ( x i ) SEQUENCE DESCRIPTION: SEQ ID NO: 164:

CTTTGCCCTG CAGCCACCAT ATACAAAGGT CTGACAGAGT CCGGCCTTGG CGTTGTAGAA      60

GTA                                                                                                               63

(2) INFORMATION FOR SEQ ID NO: 165:

(i) SEQUENCE CHARACTERISTICS:
        (A) LENGTH: 79
        (B) TYPE: nucleic acid
        (C) STRANDEDNESS: single
        (D) TOPOLOGY: linear (xi) SEQUENCE DESCRIPTION: SEQ ID NO: 165:

```
GGTCTGACAG AGACCGGCCT TGGCGTTGTG TCTTCGGTTA ATTTAAATGC GCAGAAGACC      60

CGGTATACGG TGGCTCGAG                                                  79
```

(2) INFORMATION FOR SEQ ID NO: 166:

(i) SEQUENCE CHARACTERISTICS:
        (A) LENGTH: 172
        (B) TYPE: nucleic acid
        (C) STRANDEDNESS: single
        (D) TOPOLOGY: linear (xi) SEQUENCE DESCRIPTION: SEQ ID NO: 166:

```
GCTCCGGACT TCTGTCTCGA GCCACCGTAT ACCGGGTCTT CTGCGCATTT AAATTAACCG     60

AAGACACAAC GCCAAGGCCG GACTCTGTCA GACCTTTGTA TATGGTGGCT GCCTTGCAAA    120

GCGTAACAAT TTCGAATCGG CCGAGGACTG CATGCGTACC TGTGGTGGCG CC            172
```

(2) INFORMATION FOR SEQ ID NO: 167:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

```
Ala Pro Asp Phe Cys Leu Glu Pro Pro Tyr Thr Gly
                 5                10
```

(2) INFORMATION FOR SEQ ID NO: 168:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 168:

```
Asn Ala Lys Ala Gly Leu Cys Gln Thr Phe Val Tyr Gly Gly Cys Leu
                 5                  10                  15
Ala Lys Arg Asn Asn Phe Glu Ser Ala Glu Asp Cys Met Arg Thr Cys
                20                  25                  30
Gly Gly Ala
        35
```

(2) INFORMATION FOR SEQ ID NO: 169:

(i) SEQUENCE CHARACTERISTICS:
        (A) LENGTH: 40
        (B) TYPE: nucleic acid
        (C) STRANDEDNESS: single
        (D) TOPOLOGY: linear (ix) FEATURE:

( D ) OTHER INFORMATION: R is an equimolar mixture of A and
G; N is either of G, A, T and C; and K is
either G and T.

( x i ) SEQUENCE DESCRIPTION: SEQ ID NO: 169:

TACCGGCATC TGCCGCNNKN NKNNKNNKCG CTACTTCTAC      40

( 2 ) INFORMATION FOR SEQ ID NO: 170:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear ( x i ) SEQUENCE DESCRIPTION: SEQ ID NO: 170:

GCGGCAGATG CC      12

( 2 ) INFORMATION FOR SEQ ID NO: 171:

( i ) SEQUENCE CHARACTERISTICS:
      ( A ) LENGTH: 16
      ( B ) TYPE: nucleic acid
      ( C ) STRANDEDNESS: single
      ( D ) TOPOLOGY: linear ( x i ) SEQUENCE DESCRIPTION: SEQ ID NO: 171:

CGTTGTAGAA GTAGCG      16

( 2 ) INFORMATION FOR SEQ ID NO: 172:

( i ) SEQUENCE CHARACTERISTICS:
      ( A ) LENGTH: 123
      ( B ) TYPE: nucleic acid
      ( C ) STRANDEDNESS: single
      ( D ) TOPOLOGY: linear ( i x ) FEATURE:
      ( D ) OTHER INFORMATION: N is either of G, A, T and C; H is
either of A, T and C; D is either of A,
T and G; S is either of G and C; M is
either of A and C; K is either of G
and T.

( x i ) SEQUENCE DESCRIPTION: SEQ ID NO: 172:

TCGAGCCACC GTATNNSGGT NNSTGCCGTG CTMTTCATMH SCGCTACTTC TACAACGCCA      60

AGGCGGTCT CTGTCAGACC TTTNNSTATG GTGGCTGCNN SGCAAAGCGT AACAATTTCG      120

ATC      123

( 2 ) INFORMATION FOR SEQ ID NO: 173:

( i ) SEQUENCE CHARACTERISTICS:
      ( A ) LENGTH: 124
      ( B ) TYPE: nucleic acid
      ( C ) STRANDEDNESS: single
      ( D ) TOPOLOGY: linear ( i x ) FEATURE:
      ( D ) OTHER INFORMATION: N is either of G, A, T and C; H is
either of A, T and C; D is either of A,
T and G; S is either of G and C; M is
either of A and C; K is either of G
and T.

( x i ) SEQUENCE DESCRIPTION: SEQ ID NO: 173:

GGCCGATTCG AAATTGTTAC GCTTTGCSNN GCAGCCACCA TASNNAAAGG TCTGACAGAG      60

ACCGGCCTTG GCGTTGTAGA AGTAGCGSDK ATGAAKAGCA CGGCASNNAC CSNNATACGG      120

TGGC                                                                                                            1 2 4

( 2 ) INFORMATION FOR SEQ ID NO: 174:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 174:

TTATTCGAAA CGATGTTCTC T                                                                                          2 1

( 2 ) INFORMATION FOR SEQ ID NO: 175:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 175:

GTCTTCGCTC GAGAATTCCC CGGGATCCTT AGACAT                                                                          3 6

( 2 ) INFORMATION FOR SEQ ID NO: 176:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 176:

TTATTCGAAA CGATGTTCTC T                                                                                          2 1

( 2 ) INFORMATION FOR SEQ ID NO: 177:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 177:

GTCTTCGCCG CGGGAATTCC CCGGGATCCT TAGACAT                                                                         3 7

( 2 ) INFORMATION FOR SEQ ID NO: 178:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 178:

Gln Pro Val Ile Ser Thr Thr Val Gly Ser Ala Ala Glu Gly Ser Leu
                5                         1 0                   1 5

Asp Lys Arg ( 2 ) INFORMATION FOR SEQ ID NO: 179:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear (  i  i  ) MOLECULE TYPE: peptide (  i  x  ) FEATURE:
(  D  ) OTHER INFORMATION: Xaa in position 7 is alanine,
asparagine, aspartic acid, glutamic
acid, glutamine, glycine, histidine,
isoleucine, leucine, methionine,
phenylalanine, proline, serine,
threonine, tryptophan, tyrosine, or
valine; Xaa in position 9 is alanine,
arginine, asparagine, aspartic acid,
glutamic acid, glutamine, glycine,
histidine, isoleucine, leucine, lysine,
methionine, phenylalanine, proline,
serine, threonine, tryptophan, tyrosine,
or valine; Xaa in position 10 is
alanine, or cysteine when Xaa in
position 34 is cysteine, glycine or
serine; Xaa in position 11 is arginine
or lysine; Xaa in position 12 is alanine
or glysine; Xaa in position 13 is
alanine, arginine, asparagine,
glutamine, glycine, histidine,
isoleucine, leucine, lysine, methionine,
phenylalanine, proline, serine,
threonine, tryptophan, tyrosine, or
valine; Xaa in position 14, Xaa in
position 15 and Xaa in position 16 is
any matural amino acid; Xaa in
poition 30 is alanine, arginine,
asparagine, aspartic acid, glutamic
acid, glutamine, glycine, histidine,
isoleucine, leucine, lysine, methionine,
phenylalanine, proline, serine,
threonine, tryptophan, tyrosine, or
valine; Xaa in position 31 is
phenylalanine, tryptophan or tyrosine;
Xaa in position 34 is alanine, cysteine
when Xaa in position 10 is cysteine,
glycine, or serine; Xaa in position 35
is alanine, arginine, asparagine,
aspartic acid, glutamic acid, glutamine,
glycine, histidine, isoleucine, leucine,
lysine, methionine, phenylalanine,
proline, serine, threonine, tryptophan,
tyrosine, or valine; Xaa in position 41
is phenylalanine, tryptophan or
tyrosine; and Xaa in position 42 is any
natural amino acid.

(  x  i  ) SEQUENCE DESCRIPTION: SEQ ID NO: 179:

| Cys | Leu | Glu | Pro | Pro | Tyr | Xaa | Gly | Xaa | Xaa | Xaa | Xaa | Xaa | Xaa | Xaa |
|-----|-----|-----|-----|-----|-----|-----|-----|-----|-----|-----|-----|-----|-----|-----|
|     |     |     |     | 5   |     |     |     |     | 10  |     |     |     |     | 15  |
| Tyr | Phe | Tyr | Asn | Ala | Lys | Ala | Gly | Leu | Cys | Gln | Thr | Phe | Xaa | Xaa | Gly |
|     |     |     |     | 20  |     |     |     |     | 25  |     |     |     |     | 30  |     |
| Gly | Xaa | Xaa | Ala | Lys | Arg | Asn | Asn | Xaa | Xaa | Ser | Ala | Glu | Asp | Cys | Met |
|     |     | 35  |     |     |     |     | 40  |     |     |     |     | 45  |     |     |     |
| Arg | Thr | Cys |
|     |     |     |
| 50  |     |     |

( 2 ) INFORMATION FOR SEQ ID NO: 180:

( i ) SEQUENCE CHARACTERISTICS:
( A ) LENGTH: 51 amino acids
( B ) TYPE: amino acid
( C ) STRANDEDNESS: single
( D ) TOPOLOGY: linear (  i  i  ) MOLECULE TYPE: peptide (  i  x  ) FEATURE:
( D ) OTHER INFORMATION: Xaa in position 7 is alanine, asparti
acid, glutamic acid, glycine, proline,
threonine, or valine; Xaa in position 9 is alanine, glutamine, histidine,
isoleucine, phenylalanine, proline,
tyrosine, or valine; Xaa in position 10
is cysteine; Xaa in position 11 is
arginine, or lysine; Xaa in position 12
alanine or glycine; Xaa in position 13
isoleucine, leucine, methionine, or
tyrosine; Xaa in position 14 is
histidine, isoleucine, or tyrosine; Xaa
in position 15 is glutamine, histidine,
isoleucine, leucine, lysine, proline,
threonine, or valine; Xaa in position 16
is arginine or serine; Xaa in
position 30 is aspartic acid, histidine,
isoleucine, leucine, phenylalanine,
serine, threonine, tyrosine, or valine;
Xaa in position 31 is tyrosine; Xaa in
position 34 is cysteine; Xaa in
position 35 is arginine, asparagine,
glutamic acid, histidine, leucine,
phenylalanine, tryptophan, or tyrosine;
Xaa in position 41 is phenylalanine; and
Xaa in position 42 is aspartic acid,
glutamic acid, lysine, phenylalanine,
tryptophan or tyrosine.

( x i ) SEQUENCE DESCRIPTION: SEQ ID NO: 180:

Cys Leu Glu Pro Pro Tyr Xaa Gly Xaa Xaa Xaa Xaa Xaa Xaa Xaa
                  5                   10                      15

Tyr Phe Tyr Asn Ala Lys Ala Gly Leu Cys Gln Thr Phe Xaa Xaa Gly
            20                  25                      30

Gly Xaa Xaa Ala Lys Arg Asn Asn Xaa Xaa Ser Ala Glu Asp Cys Met
        35                      40              45

Arg Thr Cys
        50

( 2 ) INFORMATION FOR SEQ ID NO: 181:

( i ) SEQUENCE CHARACTERISTICS:
                ( A ) LENGTH: 57 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( D ) OTHER INFORMATION: Xaa in position 1 is alanine or
                        arginine; Xaa in position 11 is alanine,
                        asparagine, aspartic acid, glutamic
                        acid, glutamine, glycine, histidine,
                        isoleucine, leucine, methionine,
                        phenylalanine, proline, serine,
                        threonine, tryptophan, tyrosine, or
                        valine; Xaa in position 13 is alanine,
                        arginine, asparagine, aspartic acid,
                        glutamic acid, glutamine, glycine,
                        histidine, isoleucine, leucine, lysine,
                        methionine, phenylalanine, proline,
                        serine, threonine, tryptophan, tyrosine,
                        or valine; Xaa in position 14 is
                        alanine, or cysteine when Xaa in
                        position 37 is cysteine, glycine or
                        serine; Xaa in position 15 is arginine
                        or lysine; Xaa in position 16 is alanine
                        or glysine; Xaa in position 17 is
                        alanine, arginine, asparagine,
                        glutamine, glycine, histidine,
                        isoleucine, leucine, lysine, methionine,
                        phenylalanine, proline, serine,
                        threonine, tryptophan, tyrosine, or
                        valine; Xaa in position 18, Xaa in
                        position 19 and Xaa in position 20 is
                        any matural amino acid; Xaa in
                        position 34 is alanine, arginine, asparagine, aspartic acid, glutamic
                    acid, glutamine, glycine, histidine,
                    isoleucine, leucine, lysine, methionine,
                    phenylalanine, proline, serine,
                    threonine, tryptophan, tyrosine, or
                    valine; Xaa in position 35 is
                    phenylalanine, tryptophan or tyrosine;
                    Xaa in position 37 is alanine, cysteine
                    when Xaa in position 14 is cysteine,
                    glycine, or serine; Xaa in position 38
                    is alanine, arginine, asparagine,
                    aspartic acid, glutamic acid, glutamine,
                    glycine, histidine, isoleucine, leucine,
                    lysine, methionine, phenylalanine,
                    proline, serine, threonine, tryptophan,
                    tyrosine, or valine; Xaa in position 44
                    is phenylalanine, tryptophan or
                    tyrosine; and Xaa in position 45 is any
                    natural amino acid.

( x i ) SEQUENCE DESCRIPTION: SEQ ID NO: 181:

Xaa  Pro  Asp  Phe  Cys  Leu  Glu  Pro  Pro  Tyr  Xaa  Gly  Xaa  Xaa  Xaa  Xaa
                    5                        10                        15

Xaa  Xaa  Xaa  Xaa  Tyr  Phe  Tyr  Asn  Ala  Lys  Ala  Gly  Leu  Cys  Gln  Thr
          20                        25                        30

Phe  Xaa  Xaa  Gly  Xaa  Xaa  Ala  Lys  Arg  Asn  Asn  Xaa  Xaa  Ser  Ala  Glu
          35                   40                        45

Asp  Cys  Met  Arg  Thr  Cys  Gly  Gly  Ala
     50                        55

( 2 ) INFORMATION FOR SEQ ID NO: 182:

( i ) SEQUENCE CHARACTERISTICS:
                ( A ) LENGTH: 57 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( D ) OTHER INFORMATION: Xaa in position 1 is alanine or
                    arginine; Xaa in position 11 is alanine,
                    aspartic acid, glutamic acid, glycine,
                    proline, threonine, or valine; Xaa in
                    position 13 is alanine, glutamine,
                    histidine, isoleucine, phenylalanine,
                    proline, tyrosine, or valine; Xaa in
                    position 14 is cysteine; Xaa in
                    position 15 is arginine, or lysine; Xaa
                    in position 16 alanine or glycine; Xaa
                    in position 17 isoleucine, leucine,
                    methionine, or tyrosine; Xaa in
                    position 18 is histidine, isoleucine, or
                    tyrosine; Xaa in position 19 is
                    glutamine, histidine, isoleucine,
                    leucine, lysine, proline, threonine, or
                    valine; Xaa in position 20 is arginine
                    or serine; Xaa in position 34 is
                    aspartic acid, histidine, isoleucine,
                    leucine, phenylalanine, serine,
                    threonine, tyrosine, or valine; Xaa in
                    position 35 is tyrosine; Xaa in
                    position 37 is cysteine; Xaa in
                    position 38 is arginine, asparagine,
                    glutamic acid, histidine, leucine,
                    phenylalanine, tryptophan, or tyrosine;
                    Xaa in position 44 is phenylalanine; and
                    Xaa in position 45 is aspartic acid,
                    glutamic acid, lysine, phenylalanine,
                    tryptophan or tyrosine.

( x i ) SEQUENCE DESCRIPTION: SEQ ID NO: 182:

Xaa  Pro  Asp  Phe  Cys  Leu  Glu  Pro  Pro  Tyr  Xaa  Gly  Xaa  Xaa  Xaa  Xaa

|   |   |   |   | 5 |   |   |   |   | 10 |   |   |   |   | 15 |
|---|---|---|---|---|---|---|---|---|---|---|---|---|---|---|
| Xaa | Xaa | Xaa | Xaa 20 | Tyr | Phe | Tyr | Asn | Ala 25 | Lys | Ala | Gly | Leu | Cys 30 | Gln | Thr |
| Phe | Xaa 35 | Xaa | Gly | Xaa | Xaa | Ala | Lys 40 | Arg | Asn | Asn | Xaa | Xaa 45 | Ser | Ala | Glu |
| Asp | Cys 50 | Met | Arg | Thr | Cys | Gly 55 | Gly | Ala |

(2) INFORMATION FOR SEQ ID NO: 183:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa in position 1 is alanine or arginine; Xaa in position 11 is alanine, aspartic acid, glutamic acid, glycine, proline, serine, threonine, or valine; Xaa in position 13 is alanine, glutamine, histidine, isoleucine, leucine, methionine, phenylalanine, proline, tryptophan, tyrosine, or valine; Xaa in position 14 is cysteine; Xaa in position 15 is arginine, or lysine; Xaa in position 16 is alanine or glycine; Xaa in position 17 is alanine, isoleucine, leucine, methionine, or tyrosine; Xaa in position 18 is histidine, isoleucine, phenylalanine or tyrosine; Xaa in position 19 is asparagine, glutamine, histidine, isoleucine, leucine, lysine, proline, threonine, or valine; Xaa in position 20 is arginine or serine; Xaa in position 34 is aspartic acid, histidine, isoleucine, leucine, phenylalanine, serine, threonine, tryptophan, tyrosine, or valine; Xaa in position 35 is tyrosine; Xaa in position 38 is cysteine; Xaa in position 39 is arginine, asparagine, glutamic acid, glycine, histidine, leucine, methionine, phenylalanine, tryptophan, or tyrosine; Xaa in position 45 is phenylalanine; and Xaa in position 46 is aspartic acid, glutamic acid, lysine, phenylalanine, tryptophan or tyrosine.

(xi) SEQUENCE DESCRIPTION: SEQ ID NO: 183:

|   |   |   |   | 5 |   |   |   |   | 10 |   |   |   |   | 15 |
|---|---|---|---|---|---|---|---|---|---|---|---|---|---|---|
| Xaa | Pro | Asp | Phe | Cys | Leu | Glu | Pro | Pro | Tyr | Xaa | Gly | Xaa | Xaa | Xaa | Xaa |
| Xaa | Xaa | Xaa | Xaa 20 | Tyr | Phe | Tyr | Asn | Ala 25 | Lys | Ala | Gly | Leu | Cys 30 | Gln | Thr |
| Phe | Xaa 35 | Xaa | Gly | Gly | Xaa | Xaa | Ala 40 | Lys | Arg | Asn | Asn | Xaa 45 | Xaa | Ser | Ala |
| Glu | Asp 50 | Cys | Met | Arg | Thr | Cys 55 | Gly | Gly | Ala |

(2) INFORMATION FOR SEQ ID NO: 184:

(i) SEQUENCE CHARACTERISTICS:
        (A) LENGTH: 58 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 184:

```
Ala Pro Asp Phe Cys Leu Glu Pro Pro Tyr Asp Gly Pro Cys Lys Ala
                 5                   10                  15
Ile Ile Lys Arg Tyr Phe Tyr Asn Ala Lys Ala Gly Leu Cys Gln Thr
            20                  25                  30
Phe Val Tyr Gly Gly Cys Glu Ala Lys Arg Asn Asn Phe Glu Ser Ala
        35                  40                  45
Glu Asp Cys Met Arg Thr Cys Gly Gly Ala
50                      55
```

(2) INFORMATION FOR SEQ ID NO: 185:

(i) SEQUENCE CHARACTERISTICS:
 (A) LENGTH: 58 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO: 185:

```
Ala Pro Asp Phe Cys Leu Glu Pro Pro Tyr Glu Gly Pro Cys Lys Ala
                 5                   10                  15
Ile Ile Lys Arg Tyr Phe Tyr Asn Ala Lys Ala Gly Leu Cys Gln Thr
            20                  25                  30
Phe Val Tyr Gly Gly Cys Glu Ala Lys Arg Asn Asn Phe Glu Ser Ala
        35                  40                  45
Glu Asp Cys Met Arg Thr Cys Gly Gly Ala
50                      55
```

(2) INFORMATION FOR SEQ ID NO: 186:

(i) SEQUENCE CHARACTERISTICS:
 (A) LENGTH: 58 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO: 186:

```
Ala Pro Asp Phe Cys Leu Glu Pro Pro Tyr Thr Gly Ile Cys Arg Ala
                 5                   10                  15
Tyr Ile Lys Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
50                      55
```

(2) INFORMATION FOR SEQ ID NO: 187:

(i) SEQUENCE CHARACTERISTICS:
 (A) LENGTH: 58 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO: 187:

```
Ala Pro Asp Phe Cys Leu Glu Pro Pro Tyr Asp Gly Pro Cys Arg Ala
```

|  | 5 |  |  |  |  |  | 10 |  |  |  |  |  | 15 |  |
|---|---|---|---|---|---|---|---|---|---|---|---|---|---|---|
Ile Ile Lys Arg Tyr Phe Tyr Asn Ala Lys Ala Gly Leu Cys Gln Thr
                20                  25                          30

Phe Val Tyr Gly Gly Cys Glu Ala Lys Arg Asn Asn Phe Glu Ser Ala
            35                  40                      45

Glu Asp Cys Met Arg Thr Cys Gly Gly Ala
        50                  55

( 2 ) INFORMATION FOR SEQ ID NO: 188:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 188:

Ala Pro Asp Phe Cys Leu Glu Pro Pro Tyr Asp Gly Pro Cys Arg Ala
                5                   10                  15

Ile Ile Lys Arg Tyr Phe Tyr Asn Ala Lys Ala Gly Leu Cys Gln Thr
                20                  25                          30

Phe Asp Tyr Gly Gly Cys Leu Ala Lys Arg Asn Asn Phe Lys Ser Ala
            35                  40                      45

Glu Asp Cys Met Arg Thr Cys Gly Gly Ala
        50                  55

( 2 ) INFORMATION FOR SEQ ID NO: 189:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 189:

Ala Pro Asp Phe Cys Leu Glu Pro Pro Tyr Thr Gly Pro Cys Arg Ala
                5                   10                  15

Tyr Ile Thr Arg Tyr Phe Tyr Asn Ala Lys Ala Gly Leu Cys Gln Thr
                20                  25                          30

Phe Val Tyr Gly Gly Cys Phe Ala Lys Arg Asn Asn Phe Glu Ser Ala
            35                  40                      45

Glu Asp Cys Met Arg Thr Cys Gly Gly Ala
        50                  55

( 2 ) INFORMATION FOR SEQ ID NO: 190:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 190:

Ala Pro Asp Phe Cys Leu Glu Pro Pro Tyr Asp Gly Pro Cys Lys Ala
                5                   10                  15

Ile Ile Lys Arg Tyr Phe Tyr Asn Ala Lys Ala Gly Leu Cys Gln Thr
                20                  25                          30

```
Phe Val Tyr Gly Gly Cys Phe Ala Lys Arg Asn Asn Phe Glu Ser Ala
         35                  40                  45

Glu Asp Cys Met Arg Thr Cys Gly Gly Ala
         50              55
```

( 2 ) INFORMATION FOR SEQ ID NO: 191:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 191:

```
Ala Pro Asp Phe Cys Leu Glu Pro Pro Tyr Asp Gly Pro Cys Lys Ala
             5                  10                  15

Ile Ile Lys Arg Tyr Phe Tyr Asn Ala Lys Ala Gly Leu Cys Gln Thr
         20                  25                  30

Phe Val Tyr Gly Gly Cys Tyr Ala Lys Arg Asn Asn Phe Glu Ser Ala
         35                  40                  45

Glu Asp Cys Met Arg Thr Cys Gly Gly Ala
         50              55
```

( 2 ) INFORMATION FOR SEQ ID NO: 192:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 192:

```
Ala Pro Asp Phe Cys Leu Glu Pro Pro Tyr Asp Gly Pro Cys Arg Ala
             5                  10                  15

Ile Ile Lys Arg Tyr Phe Tyr Asn Ala Lys Ala Gly Leu Cys Gln Thr
         20                  25                  30

Phe Val Tyr Gly Gly Cys Phe Ala Lys Arg Asn Asn Phe Glu Ser Ala
         35                  40                  45

Glu Asp Cys Met Arg Thr Cys Gly Gly Ala
         50              55
```

( 2 ) INFORMATION FOR SEQ ID NO: 193:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 193:

```
Ala Pro Asp Phe Cys Leu Glu Pro Pro Tyr Asp Gly Pro Cys Arg Ala
             5                  10                  15

Ile Ile Lys Arg Tyr Phe Tyr Asn Ala Lys Ala Gly Leu Cys Gln Thr
         20                  25                  30

Phe Val Tyr Gly Gly Cys Tyr Ala Lys Arg Asn Asn Phe Glu Ser Ala
         35                  40                  45

Glu Asp Cys Met Arg Thr Cys Gly Gly Ala
         50              55
```

( 2 ) INFORMATION FOR SEQ ID NO: 194:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 194:

```
Ala Pro Asp Phe Cys Leu Glu Pro Pro Tyr Thr Gly Pro Cys Arg Ala
                 5                   10                  15
Ile Ile Lys Arg Tyr Phe Tyr Asn Ala Lys Ala Gly Leu Cys Gln Thr
            20                  25                  30
Phe Val Tyr Gly Gly Cys Phe Ala Lys Arg Asn Asn Phe Glu Ser Ala
        35                  40                  45
Glu Asp Cys Met Arg Thr Cys Gly Gly Ala
50                       55
```

( 2 ) INFORMATION FOR SEQ ID NO: 195:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 195:

```
Ala Pro Asp Phe Cys Leu Glu Pro Pro Tyr Thr Gly Pro Cys Arg Ala
                 5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Tyr Ser Ala
        35                  40                  45
Glu Asp Cys Met Arg Thr Cys Gly Gly Ala
50                       55
```

( 2 ) INFORMATION FOR SEQ ID NO: 196:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 196:

```
Ala Pro Asp Phe Cys Leu Glu Pro Pro Tyr Glu Gly Pro Cys Arg Ala
                 5                   10                  15
Tyr Ile Thr Arg Tyr Phe Tyr Asn Ala Lys Ala Gly Leu Cys Gln Thr
            20                  25                  30
Phe Val Tyr Gly Gly Cys Tyr Ala Lys Arg Asn Asn Phe Glu Ser Ala
        35                  40                  45
Glu Asp Cys Met Arg Thr Cys Gly Gly Ala
50                       55
```

( 2 ) INFORMATION FOR SEQ ID NO: 197:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 197:

```
Ala Pro Asp Phe Cys Leu Glu Pro Pro Tyr Thr Gly Pro Cys Arg Ala
                 5                   10                  15
Met His His Arg Tyr Phe Tyr Asn Ala Lys Ala Gly Leu Cys Gln Thr
            20                  25                  30
Phe Val Tyr Gly Gly Cys Phe Ala Lys Arg Asn Asn Phe Glu Ser Ala
        35                  40                  45
Glu Asp Cys Met Arg Thr Cys Gly Gly Ala
    50                  55
```

(2) INFORMATION FOR SEQ ID NO: 198:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 198:

```
Ala Pro Asp Phe Cys Leu Glu Pro Pro Tyr Asp Gly Pro Cys Arg Ala
                 5                   10                  15
Leu His Leu Arg Tyr Phe Tyr Asn Ala Lys Ala Gly Leu Cys Gln Thr
            20                  25                  30
Phe Tyr Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

(2) INFORMATION FOR SEQ ID NO: 199:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 199:

```
Ala Pro Asp Phe Cys Leu Glu Pro Pro Tyr Glu Gly Tyr Cys Arg Ala
                 5                   10                  15
Leu His Ile Arg Tyr Phe Tyr Asn Ala Lys Ala Gly Leu Cys Gln Thr
            20                  25                  30
Phe Tyr Tyr Gly Gly Cys His Ala Lys Arg Asn Asn Phe Glu Ser Ala
        35                  40                  45
Glu Asp Cys Met Arg Thr Cys Gly Gly Ala
    50                  55
```

(2) INFORMATION FOR SEQ ID NO: 200:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 200:

Ala Pro Asp Phe Cys Leu Glu Pro Pro Tyr Glu Gly Ala Cys Arg Ala
                  5                  10                 15
Leu His Leu Arg Tyr Phe Tyr Asn Ala Lys Ala Gly Leu Cys Gln Thr
            20                  25                  30
Phe Tyr Tyr Gly Gly Cys Tyr Ala Lys Arg Asn Asn Phe Glu Ser Ala
        35                  40                  45
Glu Asp Cys Met Arg Thr Cys Gly Gly Ala
50                      55

( 2 ) INFORMATION FOR SEQ ID NO: 201:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 201:

Ala Pro Asp Phe Cys Leu Glu Pro Pro Tyr Glu Gly Phe Cys Arg Ala
                  5                  10                 15
Leu His Pro Arg Tyr Phe Tyr Asn Ala Lys Ala Gly Leu Cys Gln Thr
            20                  25                  30
Phe Tyr Tyr Gly Gly Cys His Ala Lys Arg Asn Asn Phe Glu Ser Ala
        35                  40                  45
Glu Asp Cys Met Arg Thr Cys Gly Gly Ala
50                      55

( 2 ) INFORMATION FOR SEQ ID NO: 202:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 202:

Ala Pro Asp Phe Cys Leu Glu Pro Pro Tyr Glu Gly Phe Cys Arg Ala
                  5                  10                 15
Leu His Thr Arg Tyr Phe Tyr Asn Ala Lys Ala Gly Leu Cys Gln Thr
            20                  25                  30
Phe Tyr Tyr Gly Gly Cys His Ala Lys Arg Asn Asn Phe Glu Ser Ala
        35                  40                  45
Glu Asp Cys Met Arg Thr Cys Gly Gly Ala
50                      55

( 2 ) INFORMATION FOR SEQ ID NO: 203:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 203:

Ala Pro Asp Phe Cys Leu Glu Pro Pro Tyr Asp Gly Pro Cys Arg Ala

```
                        5                          10                          15
Leu  His  Thr  Arg  Tyr  Phe  Tyr  Asn  Ala  Lys  Ala  Gly  Leu  Cys  Gln  Thr
               20                       25                           30

Phe  Thr  Tyr  Gly  Gly  Cys  Phe  Ala  Lys  Arg  Asn  Asn  Phe  Glu  Ser  Ala
               35                  40                            45

Glu  Asp  Cys  Met  Arg  Thr  Cys  Gly  Gly  Ala
          50                  55
```

( 2 ) INFORMATION FOR SEQ ID NO: 204:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 204:

```
Ala  Pro  Asp  Phe  Cys  Leu  Glu  Pro  Pro  Tyr  Pro  Gly  Tyr  Cys  Arg  Ala
                    5                       10                          15

Leu  His  Leu  Arg  Tyr  Phe  Tyr  Asn  Ala  Lys  Ala  Gly  Leu  Cys  Gln  Thr
               20                       25                           30

Phe  Thr  Tyr  Gly  Gly  Cys  His  Ala  Lys  Arg  Asn  Asn  Phe  Glu  Ser  Ala
               35                  40                            45

Glu  Asp  Cys  Met  Arg  Thr  Cys  Gly  Gly  Ala
          50                  55
```

( 2 ) INFORMATION FOR SEQ ID NO: 205:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 205:

```
Ala  Pro  Asp  Phe  Cys  Leu  Glu  Pro  Pro  Tyr  Asp  Gly  Pro  Cys  Arg  Ala
                    5                       10                          15

Leu  His  Gln  Arg  Tyr  Phe  Tyr  Asn  Ala  Lys  Ala  Gly  Leu  Cys  Gln  Thr
               20                       25                           30

Phe  Thr  Tyr  Gly  Gly  Cys  Arg  Ala  Lys  Arg  Asn  Asn  Phe  Glu  Ser  Ala
               35                  40                            45

Glu  Asp  Cys  Met  Arg  Thr  Cys  Gly  Gly  Ala
          50                  55
```

( 2 ) INFORMATION FOR SEQ ID NO: 206:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 206:

```
Ala  Pro  Asp  Phe  Cys  Leu  Glu  Pro  Pro  Tyr  Glu  Gly  Pro  Cys  Arg  Ala
                    5                       10                          15

Ile  His  Pro  Arg  Tyr  Phe  Tyr  Asn  Ala  Lys  Ala  Gly  Leu  Cys  Gln  Thr
               20                       25                           30
```

Phe Leu Tyr Gly Gly Cys Tyr Ala Lys Arg Asn Asn Phe Glu Ser Ala
         35                  40                  45

Glu Asp Cys Met Arg Thr Cys Gly Gly Ala
        50                  55

( 2 ) INFORMATION FOR SEQ ID NO: 207:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 207:

Ala Pro Asp Phe Cys Leu Glu Pro Pro Tyr Gly Gly Val Cys Arg Ala
                 5                  10                  15

Ile His Leu Arg Tyr Phe Tyr Asn Ala Lys Ala Gly Leu Cys Gln Thr
             20                  25                  30

Phe Ile Tyr Gly Gly Cys Tyr Ala Lys Arg Asn Asn Phe Glu Ser Ala
         35                  40                  45

Glu Asp Cys Met Arg Thr Cys Gly Gly Ala
        50                  55

( 2 ) INFORMATION FOR SEQ ID NO: 208:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 208:

Ala Pro Asp Phe Cys Leu Glu Pro Pro Tyr Ala Gly Pro Cys Arg Ala
                 5                  10                  15

Leu His Gln Arg Tyr Phe Tyr Asn Ala Lys Ala Gly Leu Cys Gln Thr
             20                  25                  30

Phe His Tyr Gly Gly Cys Phe Ala Lys Arg Asn Asn Phe Glu Ser Ala
         35                  40                  45

Glu Asp Cys Met Arg Thr Cys Gly Gly Ala
        50                  55

( 2 ) INFORMATION FOR SEQ ID NO: 209:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 209:

Ala Pro Asp Phe Cys Leu Glu Pro Pro Tyr Pro Gly Tyr Cys Arg Ala
                 5                  10                  15

Leu His Leu Arg Tyr Phe Tyr Asn Ala Lys Ala Gly Leu Cys Gln Thr
             20                  25                  30

Phe His Tyr Gly Gly Cys His Ala Lys Arg Asn Asn Phe Glu Ser Ala
         35                  40                  45

Glu Asp Cys Met Arg Thr Cys Gly Gly Ala
        50                  55

( 2 ) INFORMATION FOR SEQ ID NO: 210:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 210:

```
Ala  Pro  Asp  Phe  Cys  Leu  Glu  Pro  Pro  Tyr  Gly  Gly  Pro  Cys  Arg  Ala
                    5                        10                       15
Leu  His  Pro  Arg  Tyr  Phe  Tyr  Asn  Ala  Lys  Ala  Gly  Leu  Cys  Gln  Thr
               20                       25                       30
Phe  Phe  Tyr  Gly  Gly  Cys  Phe  Ala  Lys  Arg  Asn  Asn  Phe  Glu  Ser  Ala
          35                       40                       45
Glu  Asp  Cys  Met  Arg  Thr  Cys  Gly  Gly  Ala
     50                       55
```

( 2 ) INFORMATION FOR SEQ ID NO: 211:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 211:

```
Ala  Pro  Asp  Phe  Cys  Leu  Glu  Pro  Pro  Tyr  Gly  Gly  Val  Cys  Arg  Ala
                    5                        10                       15
Leu  His  Ile  Arg  Tyr  Phe  Tyr  Asn  Ala  Lys  Ala  Gly  Leu  Cys  Gln  Thr
               20                       25                       30
Phe  Tyr  Tyr  Gly  Gly  Cys  Asn  Ala  Lys  Arg  Asn  Asn  Phe  Glu  Ser  Ala
          35                       40                       45
Glu  Asp  Cys  Met  Arg  Thr  Cys  Gly  Gly  Ala
     50                       55
```

( 2 ) INFORMATION FOR SEQ ID NO: 212:

( i ) SEQUENCE CHARACTERISTICS:
    ( A ) LENGTH: 58 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 212:

```
Ala  Pro  Asp  Phe  Cys  Leu  Glu  Pro  Pro  Tyr  Glu  Gly  Gln  Cys  Arg  Ala
                    5                        10                       15
Leu  His  Leu  Arg  Tyr  Phe  Tyr  Asn  Ala  Lys  Ala  Gly  Leu  Cys  Gln  Thr
               20                       25                       30
Phe  Ser  Tyr  Gly  Gly  Cys  Tyr  Ala  Lys  Arg  Asn  Asn  Phe  Glu  Ser  Ala
          35                       40                       45
Glu  Asp  Cys  Met  Arg  Thr  Cys  Gly  Gly  Ala
     50                       55
```

( 2 ) INFORMATION FOR SEQ ID NO: 213:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 213:

```
Ala Pro Asp Phe Cys Leu Glu Pro Pro Tyr Ala Gly Tyr Cys Arg Ala
                 5                   10                  15
Ile His His Arg Tyr Phe Tyr Asn Ala Lys Ala Gly Leu Cys Gln Thr
                20                  25                  30
Phe Val Tyr Gly Gly Cys Tyr Ala Lys Arg Asn Asn Phe Glu Ser Ala
                35                  40                  45
Glu Asp Cys Met Arg Thr Cys Gly Gly Ala
    50                  55
```

(2) INFORMATION FOR SEQ ID NO: 214:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 214:

```
Ala Pro Asp Phe Cys Leu Glu Pro Pro Tyr Thr Gly Ile Cys Arg Ala
                 5                   10                  15
Ile His His Arg Tyr Phe Tyr Asn Ala Lys Ala Gly Leu Cys Gln Thr
                20                  25                  30
Phe Val Tyr Gly Gly Cys Leu Ala Lys Arg Asn Asn Phe Glu Ser Ala
                35                  40                  45
Glu Asp Cys Met Arg Thr Cys Gly Gly Ala
    50                  55
```

(2) INFORMATION FOR SEQ ID NO: 215:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 215:

```
Ala Pro Asp Phe Cys Leu Glu Pro Pro Tyr Pro Gly Pro Cys Arg Ala
                 5                   10                  15
Leu His Thr Arg Tyr Phe Tyr Asn Ala Lys Ala Gly Leu Cys Gln Thr
                20                  25                  30
Phe Phe Tyr Gly Gly Cys Tyr Ala Lys Arg Asn Asn Phe Glu Ser Ala
                35                  40                  45
Glu Asp Cys Met Arg Thr Cys Gly Gly Ala
    50                  55
```

(2) INFORMATION FOR SEQ ID NO: 216:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 216:

```
Ala Pro Asp Phe Cys Leu Glu Pro Pro Tyr Val Gly His Cys Arg Ala
                 5                  10                  15
Leu His Leu Arg Tyr Phe Tyr Asn Ala Lys Ala Gly Leu Cys Gln Thr
             20                  25                  30
Phe Leu Tyr Gly Gly Cys His Ala Lys Arg Asn Asn Phe Glu Ser Ala
         35                  40                  45
Glu Asp Cys Met Arg Thr Cys Gly Gly Ala
 50                          55
```

( 2 ) INFORMATION FOR SEQ ID NO: 217:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 217:

```
Ala Pro Asp Phe Cys Leu Glu Pro Pro Tyr Thr Gly Ile Cys Arg Ala
                 5                  10                  15
Leu His Gln Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
 50                          55
```

( 2 ) INFORMATION FOR SEQ ID NO: 218:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 218:

```
Ala Pro Asp Phe Cys Leu Glu Pro Pro Tyr Thr Gly Ile Cys Arg Ala
                 5                  10                  15
Leu His Ile Arg Tyr Phe Tyr Asn Ala Lys Ala Gly Leu Cys Gln Thr
             20                  25                  30
Phe Val Tyr Gly Gly Cys Leu Ala Lys Arg Asn Asn Phe Glu Ser Ala
         35                  40                  45
Glu Asp Cys Met Arg Thr Cys Gly Gly Ala
 50                          55
```

( 2 ) INFORMATION FOR SEQ ID NO: 219:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 219:

```
Ala Pro Asp Phe Cys Leu Glu Pro Pro Tyr Thr Gly Ile Cys Arg Ala
```

|  | 5 |  |  |  |  |  | 10 |  |  |  |  |  | 15 |  |
|---|---|---|---|---|---|---|---|---|---|---|---|---|---|---|

Leu His Thr Arg Tyr Phe Tyr Asn Ala Lys Ala Gly Leu Cys Gln Thr
                20                    25                        30

Phe Val Tyr Gly Gly Cys Leu Ala Lys Arg Asn Asn Phe Glu Ser Ala
            35                40                      45

Glu Asp Cys Met Arg Thr Cys Gly Gly Ala
        50              55

( 2 ) INFORMATION FOR SEQ ID NO: 220:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 220:

Ala Pro Asp Phe Cys Leu Glu Pro Pro Tyr Thr Gly Ile Cys Arg Ala
                5                   10                      15

Leu His Lys Arg Tyr Phe Tyr Asn Ala Lys Ala Gly Leu Cys Gln Thr
                20                    25                        30

Phe Val Tyr Gly Gly Cys Leu Ala Lys Arg Asn Asn Phe Glu Ser Ala
            35                40                      45

Glu Asp Cys Met Arg Thr Cys Gly Gly Ala
        50              55

( 2 ) INFORMATION FOR SEQ ID NO: 221:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 221:

Ala Pro Asp Phe Cys Leu Glu Pro Pro Tyr Thr Gly Ile Cys Arg Ala
                5                   10                      15

Ile His Leu Arg Tyr Phe Tyr Asn Ala Lys Ala Gly Leu Cys Gln Thr
                20                    25                        30

Phe Val Tyr Gly Gly Cys Leu Ala Lys Arg Asn Asn Phe Glu Ser Ala
            35                40                      45

Glu Asp Cys Met Arg Thr Cys Gly Gly Ala
        50              55

( 2 ) INFORMATION FOR SEQ ID NO: 222:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 222:

Ala Pro Asp Phe Cys Leu Glu Pro Pro Tyr Thr Gly Ile Cys Arg Ala
                5                   10                      15

Ile His Val Arg Tyr Phe Tyr Asn Ala Lys Ala Gly Leu Cys Gln Thr
                20                    25                        30

```
Phe Val Tyr Gly Gly Cys Leu Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 223:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 223:

```
Ala Pro Asp Phe Cys Leu Glu Pro Pro Tyr Thr Gly Ile Cys Arg Ala
                5                   10                      15

Met His Leu Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 224:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 224:

```
Ala Pro Asp Phe Cys Leu Glu Pro Pro Tyr Thr Gly Ile Cys Arg Ala
                5                   10                      15

Tyr Tyr Lys Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 225:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 225:

```
Ala Pro Asp Phe Cys Leu Glu Pro Pro Tyr Pro Gly Phe Cys Arg Ala
                5                   10                      15

Leu His Lys Arg Tyr Phe Tyr Asn Ala Lys Ala Gly Leu Cys Gln Thr
            20                  25                  30

Phe His Tyr Gly Gly Cys Phe Ala Lys Arg Asn Asn Phe Glu Ser Ala
        35                  40                      45

Glu Asp Cys Met Arg Thr Cys Gly Gly Ala
    50                  55
```

( 2 ) INFORMATION FOR SEQ ID NO: 226:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 226:

```
Arg Pro Asp Phe Cys Leu Glu Pro Pro Tyr Asp Gly Pro Cys Arg Ala
                 5                  10                      15
Leu His Pro Arg Tyr Phe Tyr Asn Ala Lys Ala Gly Leu Cys Gln Thr
             20                  25                  30
Phe Trp Tyr Gly Gly Cys Tyr Ala Lys Arg Asn Asn Phe Glu Ser Ala
         35              40                  45
Glu Asp Cys Met Arg Thr Cys Gly Gly Ala
         50              55
```

( 2 ) INFORMATION FOR SEQ ID NO: 227:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 227:

```
Arg Pro Asp Phe Cys Leu Glu Pro Pro Tyr Asp Gly Pro Cys Arg Ala
                 5                  10                      15
Leu His Pro Arg Tyr Phe Tyr Asn Ala Lys Ala Gly Leu Cys Gln Thr
             20                  25                  30
Phe Trp Tyr Gly Gly Cys Leu Ala Lys Arg Asn Asn Phe Glu Ser Ala
         35              40                  45
Glu Asp Cys Met Arg Thr Cys Gly Gly Ala
         50              55
```

( 2 ) INFORMATION FOR SEQ ID NO: 228:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 228:

```
Arg Pro Asp Phe Cys Leu Glu Pro Pro Tyr Asp Gly Pro Cys Arg Ala
                 5                  10                      15
Leu His His Arg Tyr Phe Tyr Asn Ala Lys Ala Gly Leu Cys Gln Thr
             20                  25                  30
Phe Tyr Tyr Gly Gly Cys Arg Ala Lys Arg Asn Asn Phe Glu Ser Ala
         35              40                  45
Glu Asp Cys Met Arg Thr Cys Gly Gly Ala
         50              55
```

( 2 ) INFORMATION FOR SEQ ID NO: 229:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 229:

| Arg | Pro | Asp | Phe | Cys | Leu | Glu | Pro | Pro | Tyr | Glu | Gly | Trp | Cys | Arg | Ala |
|---|---|---|---|---|---|---|---|---|---|---|---|---|---|---|---|
| | | | | 5 | | | | | 10 | | | | | 15 | |
| Leu | His | His | Arg | Tyr | Phe | Tyr | Asn | Ala | Lys | Ala | Gly | Leu | Cys | Gln | Thr |
| | | | 20 | | | | 25 | | | | | | 30 | | |
| Phe | Ile | Tyr | Gly | Gly | Cys | Gly | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 230:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 230:

| Arg | Pro | Asp | Phe | Cys | Leu | Glu | Pro | Pro | Tyr | Thr | Gly | Pro | Cys | Arg | Ala |
|---|---|---|---|---|---|---|---|---|---|---|---|---|---|---|---|
| | | | | 5 | | | | | 10 | | | | | 15 | |
| Leu | His | His | Arg | Tyr | Phe | Tyr | Asn | Ala | Lys | Ala | Gly | Leu | Cys | Gln | Thr |
| | | | 20 | | | | 25 | | | | | | 30 | | |
| Phe | Phe | Tyr | Gly | Gly | Cys | Phe | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 231:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 231:

| Arg | Pro | Asp | Phe | Cys | Leu | Glu | Pro | Pro | Tyr | Ser | Gly | Leu | Cys | Arg | Ala |
|---|---|---|---|---|---|---|---|---|---|---|---|---|---|---|---|
| | | | | 5 | | | | | 10 | | | | | 15 | |
| Leu | His | Lys | Arg | Tyr | Phe | Tyr | Asn | Ala | Lys | Ala | Gly | Leu | Cys | Gln | Thr |
| | | | 20 | | | | 25 | | | | | | 30 | | |
| Phe | Tyr | Tyr | Gly | Gly | Cys | Tyr | Ala | Lys | Arg | Asn | Asn | Phe | Glu | Ser | Ala |
| | | 35 | | | | | 40 | | | | | 45 | | | |
| Glu | Asp | Cys | Met | Arg | Thr | Cys | Gly | Gly | Ala | | | | | | |
| | 50 | | | | | 55 | | | | | | | | | |

(2) INFORMATION FOR SEQ ID NO: 232:

(i) SEQUENCE CHARACTERISTICS:
(A) LENGTH: 58 amino acids
(B) TYPE: amino acid
(C) STRANDEDNESS: single
(D) TOPOLOGY: linear (  i  i  ) MOLECULE TYPE: peptide (  x  i  ) SEQUENCE DESCRIPTION: SEQ ID NO: 232:

Arg Pro Asp Phe Cys Leu Glu Pro Pro Tyr Pro Gly Ile Cys Arg Ala
                  5                   10                  15

Leu His Lys Arg Tyr Phe Tyr Asn Ala Lys Ala Gly Leu Cys Gln Thr
            20                  25                  30

Phe His Tyr Gly Gly Cys Phe Ala Lys Arg Asn Asn Phe Glu Ser Ala
            35              40                  45

Glu Asp Cys Met Arg Thr Cys Gly Gly Ala
        50                  55

( 2 ) INFORMATION FOR SEQ ID NO: 233:

(  i  ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear (  i  i  ) MOLECULE TYPE: peptide (  x  i  ) SEQUENCE DESCRIPTION: SEQ ID NO: 233:

Arg Pro Asp Phe Cys Leu Glu Pro Pro Tyr Ser Gly Leu Cys Arg Ala
                  5                   10                  15

Leu His Lys Arg Tyr Phe Tyr Asn Ala Lys Ala Gly Leu Cys Gln Thr
            20                  25                  30

Phe Tyr Tyr Gly Gly Cys Phe Ala Lys Arg Asn Asn Phe Glu Ser Ala
            35              40                  45

Glu Asp Cys Met Arg Thr Cys Gly Gly Ala
        50                  55

( 2 ) INFORMATION FOR SEQ ID NO: 234:

(  i  ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear (  i  i  ) MOLECULE TYPE: peptide (  x  i  ) SEQUENCE DESCRIPTION: SEQ ID NO: 234:

Arg Pro Asp Phe Cys Leu Glu Pro Pro Tyr Pro Gly Ile Cys Arg Ala
                  5                   10                  15

Leu His Lys Arg Tyr Phe Tyr Asn Ala Lys Ala Gly Leu Cys Gln Thr
            20                  25                  30

Phe Tyr Tyr Gly Gly Cys Met Ala Lys Arg Asn Asn Phe Glu Ser Ala
            35              40                  45

Glu Asp Cys Met Arg Thr Cys Gly Gly Ala
        50                  55

( 2 ) INFORMATION FOR SEQ ID NO: 235:

(  i  ) SEQUENCE CHARACTERISTICS:
         ( A ) LENGTH: 58 amino acids
         ( B ) TYPE: amino acid
         ( C ) STRANDEDNESS: single
         ( D ) TOPOLOGY: linear (  i  i  ) MOLECULE TYPE: peptide (  x  i  ) SEQUENCE DESCRIPTION: SEQ ID NO: 235:

Arg Pro Asp Phe Cys Leu Glu Pro Pro Tyr Glu Gly Met Cys Arg Ala

```
                        5                              10                             15
Ile  His  Lys  Arg  Tyr  Phe  Tyr  Asn  Ala  Lys  Ala  Gly  Leu  Cys  Gln  Thr
               20                       25                       30

Phe  Thr  Tyr  Gly  Gly  Cys  Met  Ala  Lys  Arg  Asn  Asn  Phe  Glu  Ser  Ala
               35                       40                       45

Glu  Asp  Cys  Met  Arg  Thr  Cys  Gly  Gly  Ala
          50                   55
```

( 2 ) INFORMATION FOR SEQ ID NO: 236:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 236:

```
Arg  Pro  Asp  Phe  Cys  Leu  Glu  Pro  Pro  Tyr  Pro  Gly  Val  Cys  Arg  Ala
                    5                       10                       15

Leu  His  Lys  Arg  Tyr  Phe  Tyr  Asn  Ala  Lys  Ala  Gly  Leu  Cys  Gln  Thr
               20                       25                       30

Phe  Ser  Tyr  Gly  Gly  Cys  Gln  Ala  Lys  Arg  Asn  Asn  Phe  Glu  Ser  Ala
               35                       40                       45

Glu  Asp  Cys  Met  Arg  Thr  Cys  Gly  Gly  Ala
          50                   55
```

( 2 ) INFORMATION FOR SEQ ID NO: 237:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 237:

```
Arg  Pro  Asp  Phe  Cys  Leu  Glu  Pro  Pro  Tyr  Glu  Gly  Leu  Cys  Arg  Ala
                    5                       10                       15

Leu  His  Lys  Arg  Tyr  Phe  Tyr  Asn  Ala  Lys  Ala  Gly  Leu  Cys  Gln  Thr
               20                       25                       30

Phe  Tyr  Tyr  Gly  Gly  Cys  Phe  Ala  Lys  Arg  Asn  Asn  Phe  Glu  Ser  Ala
               35                       40                       45

Glu  Asp  Cys  Met  Arg  Thr  Cys  Gly  Gly  Ala
          50                   55
```

( 2 ) INFORMATION FOR SEQ ID NO: 238:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 238:

```
Arg  Pro  Asp  Phe  Cys  Leu  Glu  Pro  Pro  Tyr  Pro  Gly  Leu  Cys  Arg  Ala
                    5                       10                       15

Leu  His  Lys  Arg  Tyr  Phe  Tyr  Asn  Ala  Lys  Ala  Gly  Leu  Cys  Gln  Thr
               20                       25                       30
```

```
Phe Tyr Tyr Gly Gly Cys Tyr Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 239:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 239:

```
Arg Pro Asp Phe Cys Leu Glu Pro Pro Tyr Asp Gly Pro Cys Arg Ala
                5                   10                  15

Leu His Gln Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 240:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 240:

```
Arg Pro Asp Phe Cys Leu Glu Pro Ala Tyr Asp Gly Pro Cys Arg Ala
                5                   10                  15

Leu His Gln Arg Tyr Leu Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 241:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 241:

```
Arg Pro Asp Phe Cys Leu Glu Pro Pro Tyr Thr Gly Ile Cys Arg Ala
                5                   10                  15

Ala Phe Asn Arg Tyr Phe Tyr Asn Ala Lys Ala Gly Leu Cys Gln Thr
            20                  25                  30

Phe Val Tyr Gly Gly Cys Leu Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 242:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 242:

```
Arg Pro Asp Phe Cys Leu Glu Pro Pro Tyr Thr Gly Ile Cys Arg Ala
                 5                  10                      15
Phe Tyr Lys Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 243:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 243:

```
Arg Pro Asp Phe Cys Leu Glu Pro Pro Tyr Thr Gly Ile Cys Arg Ala
                 5                  10                      15
Tyr Tyr Lys Arg Tyr Phe Tyr Asn Ala Lys Ala Gly Leu Cys Gln Thr
            20                  25                  30
Phe Val Tyr Gly Gly Cys Leu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 244:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 244:

```
Ala Pro Asp Phe Cys Leu Glu Pro Pro Tyr Asp Gly Pro Cys Arg Ala
                 5                  10                      15
Ile Ile Lys Arg Tyr Phe Tyr Asn Ala Lys Ala Gly Leu Cys Gln Thr
            20                  25                  30
Phe Val Tyr Gly Gly Cys Glu Ala Lys Arg Asn Asn Phe Glu Ser Ala
        35                  40                  45
Glu Asp Cys Met Arg Thr Cys Gly Gly Ala
    50                  55
```

( 2 ) INFORMATION FOR SEQ ID NO: 245:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 245:

```
Ala Pro Asp Phe Cys Leu Glu Pro Pro Tyr Asp Gly Pro Cys Lys Ala
                 5                  10                 15
Ile Ile Lys Arg Tyr Phe Tyr Asn Ala Lys Ala Gly Leu Cys Gln Thr
                20              25                  30
Phe Val Tyr Gly Gly Cys Phe Ala Lys Arg Asn Asn Phe Glu Ser Ala
            35              40                  45
Glu Asp Cys Met Arg Thr Cys Gly Gly Ala
        50              55
```

(2) INFORMATION FOR SEQ ID NO: 246:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 246:

```
Ala Pro Asp Phe Cys Leu Glu Pro Pro Tyr Asp Gly Pro Cys Lys Ala
                 5                  10                 15
Ile Ile Lys Arg Tyr Phe Tyr Asn Ala Lys Ala Gly Leu Cys Gln Thr
                20              25                  30
Phe Val Tyr Gly Gly Cys Tyr Ala Lys Arg Asn Asn Phe Glu Ser Ala
            35              40                  45
Glu Asp Cys Met Arg Thr Cys Gly Gly Ala
        50              55
```

(2) INFORMATION FOR SEQ ID NO: 247:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 247:

```
Ala Pro Asp Phe Cys Leu Glu Pro Pro Tyr Asp Gly Pro Cys Arg Ala
                 5                  10                 15
Ile Ile Lys Arg Tyr Phe Tyr Asn Ala Lys Ala Gly Leu Cys Gln Thr
                20              25                  30
Phe Val Tyr Gly Gly Cys Phe Ala Lys Arg Asn Asn Phe Glu Ser Ala
            35              40                  45
Glu Asp Cys Met Arg Thr Cys Gly Gly Ala
        50              55
```

(2) INFORMATION FOR SEQ ID NO: 248:

(i) SEQUENCE CHARACTERISTICS:
(A) LENGTH: 58 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO: 248:

Ala Pro Asp Phe Cys Leu Glu Pro Pro Tyr Asp Gly Pro Cys Arg Ala
                 5                   10                  15

Ile Ile Lys Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 249:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 249:

Ala Pro Asp Phe Cys Leu Glu Pro Pro Tyr Thr Gly Pro Cys Arg Ala
                 5                   10                  15

Ile Ile Lys Arg Tyr Phe Tyr Asn Ala Lys Ala Gly Leu Cys Gln Thr
            20                  25                  30

Phe Val Tyr Gly Gly Cys Phe Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 250:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 250:

Ala Pro Asp Phe Cys Leu Glu Pro Pro Tyr Glu Gly Pro Cys Arg Ala
                 5                   10                  15

Tyr Ile Thr Arg Tyr Phe Tyr Asn Ala Lys Ala Gly Leu Cys Gln Thr
            20                  25                  30

Phe Val Tyr Gly Gly Cys Tyr Ala Lys Arg Asn Asn Phe Glu Ser Ala
            35              40                  45

Glu Asp Cys Met Arg Thr Cys Gly Gly Ala
50                      55

( 2 ) INFORMATION FOR SEQ ID NO: 251:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 251:

Ala Pro Asp Phe Cys Leu Glu Pro Pro Tyr Thr Gly Pro Cys Arg Ala

```
                          5                              10                              15
Met  His  His  Arg  Tyr  Phe  Tyr  Asn  Ala  Lys  Ala  Gly  Leu  Cys  Gln  Thr
               20                       25                            30

Phe  Val  Tyr  Gly  Gly  Cys  Phe  Ala  Lys  Arg  Asn  Asn  Phe  Glu  Ser  Ala
               35                       40                            45

Glu  Asp  Cys  Met  Arg  Thr  Cys  Gly  Gly  Ala
               50                       55
```

( 2 ) INFORMATION FOR SEQ ID NO: 252:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 252:

```
Ala  Pro  Asp  Phe  Cys  Leu  Glu  Pro  Pro  Tyr  Asp  Gly  Pro  Cys  Arg  Ala
                    5                        10                       15

Leu  His  Leu  Arg  Tyr  Phe  Tyr  Asn  Ala  Lys  Ala  Gly  Leu  Cys  Gln  Thr
               20                       25                            30

Phe  Tyr  Tyr  Gly  Gly  Cys  Leu  Ala  Lys  Arg  Asn  Asn  Phe  Glu  Ser  Ala
               35                       40                            45

Glu  Asp  Cys  Met  Arg  Thr  Cys  Gly  Gly  Ala
               50                       55
```

( 2 ) INFORMATION FOR SEQ ID NO: 253:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 253:

```
Ala  Pro  Asp  Phe  Cys  Leu  Glu  Pro  Pro  Tyr  Glu  Gly  Tyr  Cys  Arg  Ala
                    5                        10                       15

Leu  His  Ile  Arg  Tyr  Phe  Tyr  Asn  Ala  Lys  Ala  Gly  Leu  Cys  Gln  Thr
               20                       25                            30

Phe  Tyr  Tyr  Gly  Gly  Cys  His  Ala  Lys  Arg  Asn  Asn  Phe  Glu  Ser  Ala
               35                       40                            45

Glu  Asp  Cys  Met  Arg  Thr  Cys  Gly  Gly  Ala
               50                       55
```

( 2 ) INFORMATION FOR SEQ ID NO: 254:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 254:

```
Ala  Pro  Asp  Phe  Cys  Leu  Glu  Pro  Pro  Tyr  Glu  Gly  Ala  Cys  Arg  Ala
                    5                        10                       15

Leu  His  Leu  Arg  Tyr  Phe  Tyr  Asn  Ala  Lys  Ala  Gly  Leu  Cys  Gln  Thr
               20                       25                            30
```

```
Phe Tyr Tyr Gly Gly Cys Tyr Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 255:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 255:

```
Ala Pro Asp Phe Cys Leu Glu Pro Pro Tyr Glu Gly Phe Cys Arg Ala
                5                   10                  15

Leu His Pro Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 256:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 256:

```
Ala Pro Asp Phe Cys Leu Glu Pro Pro Tyr Glu Gly Phe Cys Arg Ala
                5                   10                  15

Leu His Thr Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 257:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 257:

```
Ala Pro Asp Phe Cys Leu Glu Pro Pro Tyr Asp Gly Pro Cys Arg Ala
                5                   10                  15

Leu His Thr Arg Tyr Phe Tyr Asn Ala Lys Ala Gly Leu Cys Gln Thr
            20                  25                  30

Phe Thr Tyr Gly Gly Cys Phe Ala Lys Arg Asn Asn Phe Glu Ser Ala
            35                  40                  45

Glu Asp Cys Met Arg Thr Cys Gly Gly Ala
    50                  55
```

( 2 ) INFORMATION FOR SEQ ID NO: 258:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 258:

```
Ala Pro Asp Phe Cys Leu Glu Pro Pro Tyr Pro Gly Tyr Cys Arg Ala
                 5                  10                      15
Leu His Leu Arg Tyr Phe Tyr Asn Ala Lys Ala Gly Leu Cys Gln Thr
                20              25                  30
Phe Thr Tyr Gly Gly Cys His Ala Lys Arg Asn Asn Phe Glu Ser Ala
            35          40                  45
Glu Asp Cys Met Arg Thr Cys Gly Gly Ala
        50              55
```

( 2 ) INFORMATION FOR SEQ ID NO: 259:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 259:

```
Ala Pro Asp Phe Cys Leu Glu Pro Pro Tyr Asp Gly Pro Cys Arg Ala
                 5                  10                      15
Leu His Gln Arg Tyr Phe Tyr Asn Ala Lys Ala Gly Leu Cys Gln Thr
                20              25                  30
Phe Thr Tyr Gly Gly Cys Arg Ala Lys Arg Asn Asn Phe Glu Ser Ala
            35          40                  45
Glu Asp Cys Met Arg Thr Cys Gly Gly Ala
        50              55
```

( 2 ) INFORMATION FOR SEQ ID NO: 260:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 260:

```
Ala Pro Asp Phe Cys Leu Glu Pro Pro Tyr Glu Gly Pro Cys Arg Ala
                 5                  10                      15
Ile His Pro Arg Tyr Phe Tyr Asn Ala Lys Ala Gly Leu Cys Gln Thr
                20              25                  30
Phe Leu Tyr Gly Gly Cys Tyr Ala Lys Arg Asn Asn Phe Glu Ser Ala
            35          40                  45
Glu Asp Cys Met Arg Thr Cys Gly Gly Ala
        50              55
```

( 2 ) INFORMATION FOR SEQ ID NO: 261:

( i ) SEQUENCE CHARACTERISTICS:

(A) LENGTH: 58 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO: 261:

Arg Pro Asp Phe Cys Leu Glu Pro Pro Tyr Thr Gly Ile Cys Arg Ala
                  5                   10                  15
Leu His Ile Arg Tyr Phe Tyr Asn Ala Lys Ala Gly Leu Cys Gln Thr
              20                  25                  30
Phe Val Tyr Gly Gly Cys Leu Ala Lys Arg Asn Asn Phe Glu Ser Ala
              35                  40                  45
Glu Asp Cys Met Arg Thr Cys Gly Gly Ala
         50                  55

(2) INFORMATION FOR SEQ ID NO: 262:

(i) SEQUENCE CHARACTERISTICS:
    (A) LENGTH: 58 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 262:

Arg Pro Asp Phe Cys Leu Glu Pro Pro Tyr Asp Gly Pro Cys Arg Ala
                  5                   10                  15
Leu His Thr Arg Tyr Phe Tyr Asn Ala Lys Ala Gly Leu Cys Gln Thr
              20                  25                  30
Phe Thr Tyr Gly Gly Cys Phe Ala Lys Arg Asn Asn Phe Glu Ser Ala
              35                  40                  45
Glu Asp Cys Met Arg Thr Cys Gly Gly Ala
         50                  55

(2) INFORMATION FOR SEQ ID NO: 263:

(i) SEQUENCE CHARACTERISTICS:
    (A) LENGTH: 58 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO: 263:

Arg Pro Asp Phe Cys Leu Glu Pro Pro Tyr Gly Gly Val Cys Arg Ala
                  5                   10                  15
Ile His Leu Arg Tyr Phe Tyr Asn Ala Lys Ala Gly Leu Cys Gln Thr
              20                  25                  30
Phe Ile Tyr Gly Gly Cys Tyr Ala Lys Arg Asn Asn Phe Glu Ser Ala
              35                  40                  45
Glu Asp Cys Met Arg Thr Cys Gly Gly Ala
         50                  55

(2) INFORMATION FOR SEQ ID NO: 264:

(i) SEQUENCE CHARACTERISTICS:
    (A) LENGTH: 58 amino acids
    (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO: 264:

Arg Pro Asp Phe Cys Leu Glu Pro Pro Tyr Glu Gly Pro Cys Arg Ala
                 5                   10                  15

Ile His Pro Arg Tyr Phe Tyr Asn Ala Lys Ala Gly Leu Cys Gln Thr
            20                  25                  30

Phe Leu Tyr Gly Gly Cys Tyr Ala Lys Arg Asn Asn Phe Glu Ser Ala
        35                  40                  45

Glu Asp Cys Met Arg Thr Cys Gly Gly Ala
50                       55

( 2 ) INFORMATION FOR SEQ ID NO: 265:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 265:

Arg Pro Asp Phe Cys Leu Glu Pro Pro Tyr Asp Gly Pro Cys Arg Ala
                 5                   10                  15

Leu His Gln Arg Tyr Phe Tyr Asn Ala Lys Ala Gly Leu Cys Gln Thr
            20                  25                  30

Phe Thr Tyr Gly Gly Cys Arg Ala Lys Arg Asn Asn Phe Glu Ser Ala
        35                  40                  45

Glu Asp Cys Met Arg Thr Cys Gly Gly Ala
50                       55

( 2 ) INFORMATION FOR SEQ ID NO: 266:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 266:

Arg Pro Asp Phe Cys Leu Glu Pro Pro Tyr Glu Gly Phe Cys Arg Ala
                 5                   10                  15

Leu His Thr Arg Tyr Phe Tyr Asn Ala Lys Ala Gly Leu Cys Gln Thr
            20                  25                  30

Phe Tyr Tyr Gly Gly Cys His Ala Lys Arg Asn Asn Phe Glu Ser Ala
        35                  40                  45

Glu Asp Cys Met Arg Thr Cys Gly Gly Ala
50                       55

( 2 ) INFORMATION FOR SEQ ID NO: 267:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 267:

Arg Pro Asp Phe Cys Leu Glu Pro Pro Tyr Glu Gly Ala Cys Arg Ala

```
                         5                            10                           15
Leu  His  Leu  Arg  Tyr  Phe  Tyr  Asn  Ala  Lys  Ala  Gly  Leu  Cys  Gln  Thr
               20                       25                           30

Phe  Tyr  Tyr  Gly  Gly  Cys  Tyr  Ala  Lys  Arg  Asn  Asn  Phe  Glu  Ser  Ala
               35                       40                           45

Glu  Asp  Cys  Met  Arg  Thr  Cys  Gly  Gly  Ala
          50                        55
```

( 2 ) INFORMATION FOR SEQ ID NO: 268:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 268:

```
Arg  Pro  Asp  Phe  Cys  Leu  Glu  Pro  Pro  Tyr  Asp  Gly  Pro  Cys  Arg  Ala
                    5                       10                       15

Leu  His  Leu  Arg  Tyr  Phe  Tyr  Asn  Ala  Lys  Ala  Gly  Leu  Cys  Gln  Thr
               20                       25                           30

Phe  Tyr  Tyr  Gly  Gly  Cys  Leu  Ala  Lys  Arg  Asn  Asn  Phe  Glu  Ser  Ala
               35                       40                           45

Glu  Asp  Cys  Met  Arg  Thr  Cys  Gly  Gly  Ala
          50                        55
```

( 2 ) INFORMATION FOR SEQ ID NO: 269:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 269:

```
Arg  Pro  Asp  Phe  Cys  Leu  Glu  Pro  Pro  Tyr  Glu  Gly  Tyr  Cys  Arg  Ala
                    5                       10                       15

Leu  His  Ile  Arg  Tyr  Phe  Tyr  Asn  Ala  Lys  Ala  Gly  Leu  Cys  Gln  Thr
               20                       25                           30

Phe  Tyr  Tyr  Gly  Gly  Cys  His  Ala  Lys  Arg  Asn  Asn  Phe  Glu  Ser  Ala
               35                       40                           45

Glu  Asp  Cys  Met  Arg  Thr  Cys  Gly  Gly  Ala
          50                        55
```

( 2 ) INFORMATION FOR SEQ ID NO: 270:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 270:

```
Arg  Pro  Asp  Phe  Cys  Leu  Glu  Pro  Pro  Tyr  Pro  Gly  Tyr  Cys  Arg  Ala
                    5                       10                       15

Leu  His  Leu  Arg  Tyr  Phe  Tyr  Asn  Ala  Lys  Ala  Gly  Leu  Cys  Gln  Thr
               20                       25                           30
```

```
Phe  Thr  Tyr  Gly  Gly  Cys  His  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 271:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 271:

```
Arg  Pro  Asp  Phe  Cys  Leu  Glu  Pro  Pro  Tyr  Asp  Gly  Pro  Cys  Arg  Ala
                    5                        10                       15

Leu  His  Pro  Arg  Tyr  Phe  Tyr  Asn  Ala  Lys  Ala  Gly  Leu  Cys  Gln  Thr
               20                       25                       30

Phe  Trp  Tyr  Gly  Gly  Cys  Tyr  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 272:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 272:

```
Arg  Pro  Asp  Phe  Cys  Leu  Glu  Pro  Pro  Tyr  Asp  Gly  Pro  Cys  Arg  Ala
                    5                        10                       15

Leu  His  Pro  Arg  Tyr  Phe  Tyr  Asn  Ala  Lys  Ala  Gly  Leu  Cys  Gln  Thr
               20                       25                       30

Phe  Trp  Tyr  Gly  Gly  Cys  Leu  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 273:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 273:

```
Arg  Pro  Asp  Phe  Cys  Leu  Glu  Pro  Pro  Tyr  Asp  Gly  Pro  Cys  Arg  Ala
                    5                        10                       15

Leu  His  His  Arg  Tyr  Phe  Tyr  Asn  Ala  Lys  Ala  Gly  Leu  Cys  Gln  Thr
               20                       25                       30

Phe  Tyr  Tyr  Gly  Gly  Cys  Arg  Ala  Lys  Arg  Asn  Asn  Phe  Glu  Ser  Ala
          35                       40                       45

Glu  Asp  Cys  Met  Arg  Thr  Cys  Gly  Gly  Ala
     50                       55
```

( 2 ) INFORMATION FOR SEQ ID NO: 274:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 274:

```
Arg  Pro  Asp  Phe  Cys  Leu  Glu  Pro  Pro  Tyr  Glu  Gly  Trp  Cys  Arg  Ala
                    5                        10                       15
Leu  His  His  Arg  Tyr  Phe  Tyr  Asn  Ala  Lys  Ala  Gly  Leu  Cys  Gln  Thr
               20                       25                      30
Phe  Ile  Tyr  Gly  Gly  Cys  Gly  Ala  Lys  Arg  Asn  Asn  Phe  Glu  Ser  Ala
               35                  40                       45
Glu  Asp  Cys  Met  Arg  Thr  Cys  Gly  Gly  Ala
          50                   55
```

( 2 ) INFORMATION FOR SEQ ID NO: 275:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 275:

```
Arg  Pro  Asp  Phe  Cys  Leu  Glu  Pro  Pro  Tyr  Thr  Gly  Pro  Cys  Arg  Ala
                    5                        10                       15
Leu  His  His  Arg  Tyr  Phe  Tyr  Asn  Ala  Lys  Ala  Gly  Leu  Cys  Gln  Thr
               20                       25                      30
Phe  Phe  Tyr  Gly  Gly  Cys  Phe  Ala  Lys  Arg  Asn  Asn  Phe  Glu  Ser  Ala
               35                  40                       45
Glu  Asp  Cys  Met  Arg  Thr  Cys  Gly  Gly  Ala
          50                   55
```

( 2 ) INFORMATION FOR SEQ ID NO: 276:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 276:

```
Arg  Pro  Asp  Phe  Cys  Leu  Glu  Pro  Pro  Tyr  Ser  Gly  Leu  Cys  Arg  Ala
                    5                        10                       15
Leu  His  Lys  Arg  Tyr  Phe  Tyr  Asn  Ala  Lys  Ala  Gly  Leu  Cys  Gln  Thr
               20                       25                      30
Phe  Tyr  Tyr  Gly  Gly  Cys  Tyr  Ala  Lys  Arg  Asn  Asn  Phe  Glu  Ser  Ala
               35                  40                       45
Glu  Asp  Cys  Met  Arg  Thr  Cys  Gly  Gly  Ala
          50                   55
```

( 2 ) INFORMATION FOR SEQ ID NO: 277:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 277:

| Arg | Pro | Asp | Phe | Cys | Leu | Glu | Pro | Pro | Tyr | Pro | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | His | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 278:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 278:

| Arg | Pro | Asp | Phe | Cys | Leu | Glu | Pro | Pro | Tyr | Ser | Gly | Leu | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Tyr | Tyr | Gly | Gly | Cys | Phe | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 279:

(i) SEQUENCE CHARACTERISTICS:
(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 279:

| Arg | Pro | Asp | Phe | Cys | Leu | Glu | Pro | Pro | Tyr | Pro | Gly | Ile | Cys | Arg | Ala |
|-----|-----|-----|-----|-----|-----|-----|-----|-----|-----|-----|-----|-----|-----|-----|-----|
|     |     |     |     | 5   |     |     |     |     | 10  |     |     |     |     |     | 15  |
| Leu | His | Lys | Arg | Tyr | Phe | Tyr | Asn | Ala | Lys | Ala | Gly | Leu | Cys | Gln | Thr |
|     |     |     | 20  |     |     |     |     | 25  |     |     |     |     | 30  |     |     |
| Phe | Tyr | Tyr | Gly | Gly | Cys | Met | Ala | Lys | Arg | Asn | Asn | Phe | Glu | Ser | Ala |
|     |     | 35  |     |     |     |     | 40  |     |     |     |     | 45  |     |     |     |
| Glu | Asp | Cys | Met | Arg | Thr | Cys | Gly | Gly | Ala |
|     | 50  |     |     |     |     | 55  |     |     |     |

(2) INFORMATION FOR SEQ ID NO: 280:

(i) SEQUENCE CHARACTERISTICS:
(A) LENGTH: 58 amino acids
(B) TYPE: amino acid
(C) STRANDEDNESS: single
(D) TOPOLOGY: linear (  i i  ) MOLECULE TYPE: peptide (  x i  ) SEQUENCE DESCRIPTION: SEQ ID NO: 280:

| Arg | Pro | Asp | Phe | Cys | Leu | Glu | Pro | Pro | Tyr | Glu | Gly | Met | Cys | Arg | Ala |
|-----|-----|-----|-----|-----|-----|-----|-----|-----|-----|-----|-----|-----|-----|-----|-----|
|     |     |     |     | 5   |     |     |     |     | 1 0 |     |     |     |     | 1 5 |     |
| Ile | His | Lys | Arg | Tyr | Phe | Tyr | Asn | Ala | Lys | Ala | Gly | Leu | Cys | Gln | Thr |
|     |     |     | 2 0 |     |     |     |     | 2 5 |     |     |     |     | 3 0 |     |     |
| Phe | Thr | Tyr | Gly | Gly | Cys | Met | Ala | Lys | Arg | Asn | Asn | Phe | Glu | Ser | Ala |
|     |     | 3 5 |     |     |     |     | 4 0 |     |     |     |     | 4 5 |     |     |     |
| Glu | Asp | Cys | Met | Arg | Thr | Cys | Gly | Gly | Ala |
|     | 5 0 |     |     |     |     | 5 5 |     |     |     |

( 2 ) INFORMATION FOR SEQ ID NO: 281:

(  i  ) SEQUENCE CHARACTERISTICS:
( A ) LENGTH: 58 amino acids
( B ) TYPE: amino acid
( C ) STRANDEDNESS: single
( D ) TOPOLOGY: linear (  i i  ) MOLECULE TYPE: peptide (  x i  ) SEQUENCE DESCRIPTION: SEQ ID NO: 281:

| Arg | Pro | Asp | Phe | Cys | Leu | Glu | Pro | Pro | Tyr | Pro | Gly | Val | Cys | Arg | Ala |
|-----|-----|-----|-----|-----|-----|-----|-----|-----|-----|-----|-----|-----|-----|-----|-----|
|     |     |     |     | 5   |     |     |     |     | 1 0 |     |     |     |     | 1 5 |     |
| Leu | His | Lys | Arg | Tyr | Phe | Tyr | Asn | Ala | Lys | Ala | Gly | Leu | Cys | Gln | Thr |
|     |     |     | 2 0 |     |     |     |     | 2 5 |     |     |     |     | 3 0 |     |     |
| Phe | Ser | Tyr | Gly | Gly | Cys | Gln | Ala | Lys | Arg | Asn | Asn | Phe | Glu | Ser | Ala |
|     |     | 3 5 |     |     |     |     | 4 0 |     |     |     |     | 4 5 |     |     |     |
| Glu | Asp | Cys | Met | Arg | Thr | Cys | Gly | Gly | Ala |
|     | 5 0 |     |     |     |     | 5 5 |     |     |     |

( 2 ) INFORMATION FOR SEQ ID NO: 282:

(  i  ) SEQUENCE CHARACTERISTICS:
( A ) LENGTH: 58 amino acids
( B ) TYPE: amino acid
( C ) STRANDEDNESS: single
( D ) TOPOLOGY: linear (  i i  ) MOLECULE TYPE: peptide (  x i  ) SEQUENCE DESCRIPTION: SEQ ID NO: 282:

| Arg | Pro | Asp | Phe | Cys | Leu | Glu | Pro | Pro | Tyr | Glu | Gly | Leu | Cys | Arg | Ala |
|-----|-----|-----|-----|-----|-----|-----|-----|-----|-----|-----|-----|-----|-----|-----|-----|
|     |     |     |     | 5   |     |     |     |     | 1 0 |     |     |     |     | 1 5 |     |
| Leu | His | Lys | Arg | Tyr | Phe | Tyr | Asn | Ala | Lys | Ala | Gly | Leu | Cys | Gln | Thr |
|     |     |     | 2 0 |     |     |     |     | 2 5 |     |     |     |     | 3 0 |     |     |
| Phe | Tyr | Tyr | Gly | Gly | Cys | Phe | Ala | Lys | Arg | Asn | Asn | Phe | Glu | Ser | Ala |
|     |     | 3 5 |     |     |     |     | 4 0 |     |     |     |     | 4 5 |     |     |     |
| Glu | Asp | Cys | Met | Arg | Thr | Cys | Gly | Gly | Ala |
|     | 5 0 |     |     |     |     | 5 5 |     |     |     |

( 2 ) INFORMATION FOR SEQ ID NO: 283:

(  i  ) SEQUENCE CHARACTERISTICS:
( A ) LENGTH: 58 amino acids
( B ) TYPE: amino acid
( C ) STRANDEDNESS: single
( D ) TOPOLOGY: linear (  i i  ) MOLECULE TYPE: peptide (  x i  ) SEQUENCE DESCRIPTION: SEQ ID NO: 283:

| Arg | Pro | Asp | Phe | Cys | Leu | Glu | Pro | Pro | Tyr | Pro | Gly | Leu | Cys | Arg | Ala |
|-----|-----|-----|-----|-----|-----|-----|-----|-----|-----|-----|-----|-----|-----|-----|-----|

|  | 5 |  |  |  |  |  |  | 10 |  |  |  |  |  | 15 |  |
|---|---|---|---|---|---|---|---|---|---|---|---|---|---|---|---|
| Leu | His | Lys | Arg | Tyr | Phe | Tyr | Asn | Ala | Lys | Ala | Gly | Leu | Cys | Gln | Thr |
|  |  |  | 20 |  |  |  |  | 25 |  |  |  |  |  | 30 |  |
| Phe | Tyr | Tyr | Gly | Gly | Cys | Tyr | Ala | Lys | Arg | Asn | Asn | Phe | Glu | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  |  | 50 |  |  |  | 55 |  |  |  |

( 2 ) INFORMATION FOR SEQ ID NO: 284:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 284:

| Arg | Pro | Asp | Phe | Cys | Leu | Glu | Pro | Pro | Tyr | Asp | Gly | Pro | Cys | Arg | Ala |
|---|---|---|---|---|---|---|---|---|---|---|---|---|---|---|---|
|  |  |  |  | 5 |  |  |  |  | 10 |  |  |  |  | 15 |  |
| Leu | His | Gln | Arg | Tyr | Phe | Tyr | Asn | Ala | Lys | Ala | Gly | Leu | Cys | Gln | Thr |
|  |  |  | 20 |  |  |  |  | 25 |  |  |  |  |  | 30 |  |
| Phe | Val | Tyr | Gly | Gly | Cys | Phe | Ala | Lys | Arg | Asn | Asn | Phe | Glu | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  |  | 50 |  |  |  | 55 |  |  |  |

( 2 ) INFORMATION FOR SEQ ID NO: 285:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 285:

| Arg | Pro | Asp | Phe | Cys | Leu | Glu | Pro | Ala | Tyr | Asp | Gly | Pro | Cys | Arg | Ala |
|---|---|---|---|---|---|---|---|---|---|---|---|---|---|---|---|
|  |  |  |  | 5 |  |  |  |  | 10 |  |  |  |  | 15 |  |
| Leu | His | Gln | Arg | Tyr | Leu | Tyr | Asn | Ala | Lys | Ala | Gly | Leu | Cys | Gln | Thr |
|  |  |  | 20 |  |  |  |  | 25 |  |  |  |  |  | 30 |  |
| Phe | Val | Tyr | Gly | Gly | Cys | Phe | Ala | Lys | Arg | Asn | Asn | Phe | Glu | Ser | Ala |
|  |  | 35 |  |  |  |  | 40 |  |  |  |  | 45 |  |  |  |
| Glu | Asp | Cys | Met | Arg | Thr | Cys | Gly | Gly | Ala |
|  |  | 50 |  |  |  | 55 |  |  |  |

( 2 ) INFORMATION FOR SEQ ID NO: 286:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 286:

| Arg | Pro | Asp | Phe | Cys | Leu | Glu | Pro | Pro | Tyr | Asp | Gly | Pro | Cys | Arg | Ala |
|---|---|---|---|---|---|---|---|---|---|---|---|---|---|---|---|
|  |  |  |  | 5 |  |  |  |  | 10 |  |  |  |  | 15 |  |
| Leu | His | Gln | Arg | Tyr | Phe | Tyr | Asn | Ala | Lys | Ala | Gly | Leu | Cys | Gln | Thr |
|  |  |  | 20 |  |  |  |  | 25 |  |  |  |  |  | 30 |  |

```
Phe  Thr  Tyr  Gly  Gly  Cys  Arg  Ala  Lys  Arg  Asn  Asn  Phe  Glu  Ser  Ala
          35                  40                      45

Glu  Asp  Cys  Met  Arg  Thr  Cys  Gly  Gly  Ala
          50                  55
```

(2) INFORMATION FOR SEQ ID NO: 287:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 287:

```
Arg  Pro  Asp  Phe  Cys  Leu  Glu  Pro  Pro  Tyr  Asp  Gly  Pro  Cys  Arg  Ala
                    5                       10                      15

Leu  His  Leu  Arg  Tyr  Phe  Tyr  Asn  Ala  Lys  Ala  Gly  Leu  Cys  Gln  Thr
               20                       25                      30

Phe  Tyr  Tyr  Gly  Gly  Cys  Leu  Ala  Lys  Arg  Asn  Asn  Phe  Glu  Ser  Ala
          35                  40                      45

Glu  Asp  Cys  Met  Arg  Thr  Cys  Gly  Gly  Ala
          50                  55
```

(2) INFORMATION FOR SEQ ID NO: 288:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 288:

```
Arg  Pro  Asp  Phe  Cys  Leu  Glu  Pro  Pro  Tyr  Glu  Gly  Tyr  Cys  Arg  Ala
                    5                       10                      15

Leu  His  Ile  Arg  Tyr  Phe  Tyr  Asn  Ala  Lys  Ala  Gly  Leu  Cys  Gln  Thr
               20                       25                      30

Phe  Tyr  Tyr  Gly  Gly  Cys  His  Ala  Lys  Arg  Asn  Asn  Phe  Glu  Ser  Ala
          35                  40                      45

Glu  Asp  Cys  Met  Arg  Thr  Cys  Gly  Gly  Ala
          50                  55
```

(2) INFORMATION FOR SEQ ID NO: 289:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 289:

```
Arg  Pro  Asp  Phe  Cys  Leu  Glu  Pro  Pro  Tyr  Asp  Gly  Pro  Cys  Arg  Ala
                    5                       10                      15

Leu  His  Pro  Arg  Tyr  Phe  Tyr  Asn  Ala  Lys  Ala  Gly  Leu  Cys  Gln  Thr
               20                       25                      30

Phe  Trp  Tyr  Gly  Gly  Cys  Tyr  Ala  Lys  Arg  Asn  Asn  Phe  Glu  Ser  Ala
          35                  40                      45

Glu  Asp  Cys  Met  Arg  Thr  Cys  Gly  Gly  Ala
          50                  55
```

( 2 ) INFORMATION FOR SEQ ID NO: 290:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 290:

```
Arg Pro Asp Phe Cys Leu Glu Pro Pro Tyr Asp Gly Pro Cys Arg Ala
                 5                  10                    15
Leu His Pro Arg Tyr Phe Tyr Asn Ala Lys Ala Gly Leu Cys Gln Thr
            20                  25              30
Phe Trp Tyr Gly Gly Cys Leu Ala Lys Arg Asn Asn Phe Glu Ser Ala
        35              40                  45
Glu Asp Cys Met Arg Thr Cys Gly Gly Ala
    50              55
```

( 2 ) INFORMATION FOR SEQ ID NO: 291:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 291:

```
Arg Pro Asp Phe Cys Leu Glu Pro Pro Tyr Asp Gly Pro Cys Arg Ala
                 5                  10                    15
Leu His His Arg Tyr Phe Tyr Asn Ala Lys Ala Gly Leu Cys Gln Thr
            20                  25              30
Phe Tyr Tyr Gly Gly Cys Arg Ala Lys Arg Asn Asn Phe Glu Ser Ala
        35              40                  45
Glu Asp Cys Met Arg Thr Cys Gly Gly Ala
    50              55
```

( 2 ) INFORMATION FOR SEQ ID NO: 292:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 292:

```
Arg Pro Asp Phe Cys Leu Glu Pro Pro Tyr Ser Gly Leu Cys Arg Ala
                 5                  10                    15
Leu His Lys Arg Tyr Phe Tyr Asn Ala Lys Ala Gly Leu Cys Gln Thr
            20                  25              30
Phe Tyr Tyr Gly Gly Cys Phe Ala Lys Arg Asn Asn Phe Glu Ser Ala
        35              40                  45
Glu Asp Cys Met Arg Thr Cys Gly Gly Ala
    50              55
```

( 2 ) INFORMATION FOR SEQ ID NO: 293:

( i ) SEQUENCE CHARACTERISTICS:

(A) LENGTH: 58 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 293:

Arg Pro Asp Phe Cys Leu Glu Pro Pro Tyr Glu Gly Leu Cys Arg Ala
                  5                   10                      15
Leu His Lys Arg Tyr Phe Tyr Asn Ala Lys Ala Gly Leu Cys Gln Thr
            20              25                      30
Phe Tyr Tyr Gly Gly Cys Phe Ala Lys Arg Asn Asn Phe Glu Ser Ala
        35              40                      45
Glu Asp Cys Met Arg Thr Cys Gly Gly Ala
    50                  55

(2) INFORMATION FOR SEQ ID NO: 294:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 294:

Arg Pro Asp Phe Cys Leu Glu Pro Ala Tyr Asp Gly Pro Cys Arg Ala
                  5                   10                      15
Leu His Gln Arg Tyr Leu Tyr Asn Ala Lys Ala Gly Leu Cys Gln Thr
            20              25                      30
Phe Val Tyr Gly Gly Cys Phe Ala Lys Arg Asn Asn Phe Glu Ser Ala
        35              40                      45
Glu Asp Cys Met Arg Thr Cys Gly Gly Ala
    50                  55

Other embodiments are within the following claims.

We claim:

1. A compound derived from bovine pancreatic trypsin inhibitor which inhibits the biological activity of factor VIIa-tissue factor complex with an inhibition constant less than 500 nM selected from the group consisting of:

BPTI(1Ala 11Asp 17Ile 19Lys 39Glu 46Glu)
BPTI(1Ala 11Glu 17Ile 19Lys 39Glu 46Glu)
BPTI(1Ala 13Ile 15Arg 17Tyr 19Lys 39Leu 46Glu)
BPTI(1Ala 11Asp 15Arg 17Ile 19Glu 39Glu 46Glu)
BPTI(1Ala 11Asp 15Arg 17Ile 19Lys 34Asp 39Leu)
BPTI(1Ala 15Arg 17Tyr 19Thr 39Phe 46Glu)
BPTI(1Ala 11Asp 17Ile 19Lys 39Phe 46Glu)
BPTI(1Ala 11Asp 17Ile 19Lys 39Tyr 46Glu)
BPTI(1Ala 11Asp 15Arg 17Ile 19Lys 39Phe 46Glu)
BPTI(1Ala 11Asp 15Arg 17Ile 19Lys 39Tyr 46Glu)
BPTI(1Ala 15Arg 17Ile 19Lys 39Phe 46Glu)
BPTI(1Ala 15Arg 17Tyr 19Thr 39Tyr 46Tyr)
BPTI(1Ala 11Glu 15Arg 17Tyr 19Thr 39Tyr 46Glu)
BPTI(1Ala 15Arg 17Met 18His 19His 39Phe 46Glu)
BPTI(1Ala 11Asp 15Arg 17Leu 18His 19Leu 34Tyr 39Leu 46Glu)
BPTI(1Ala 11Glu 13Tyr 15Arg 17Leu 18His 34Tyr 39His 46Glu
BPTI(1Ala 11Glu 13Ala 15Arg 17Leu 18His 19Leu 34Tyr 39Tyr 46Glu)
BPTI(1Ala 11Glu 13Phe 15Arg 17Leu 18His 19Pro 34Tyr 39His 46Glu)
BPTI(1Ala 11Glu 13Phe 15Arg 17Leu 18His 19Thr 34Tyr 39His 46Glu)
BPTI(1Ala 11Asp 15Arg 17Leu 18His 19Thr 34Thr 39Phe 46Glu)
BPTI(1Ala 11Pro 13Tyr 15Arg 17Leu 18His 19Leu 34Thr 39His 46Glu)
BPTI(1Ala 11Asp 15Arg 17Leu 18His 19Gln 34Thr 46Glu)

BPTI(1Ala 11Glu 15Arg 17Ile 18His 19Pro 34Leu 39Tyr 46Glu)
BPTI(1Ala 11Gly 13Val 15Arg 17Ile 18His 19Leu 34Ile 39Tyr 46Glu)
BPTI(1Ala 11Ala 15Arg 17Leu 18His 19Gln 34His 39Phe 46Glu)
BPTI(1Ala 11Pro 13Tyr 15Arg 17Leu 18His 19Leu 34His 39His 46Glu)
BPTI(1Ala 11Gly 15Arg 17Leu 18His 19Pro 34Phe 39Phe 46Glu)
BPTI(1Ala 11Gly 13Val 15Arg 17Leu 18His 34Tyr 39Asn 46Glu)
BPTI(1Ala 11Glu 13Gln 15Arg 17Leu 18His 19Leu 34Ser 39Tyr 46Glu)
BPTI(1Ala 11Ala 13Tyr 15Arg 17Ile 18His 19His 39Tyr 46Glu)
BPTI(1Ala 13Ile 15Arg 17Ile 18His 19His 39Leu 46Glu)
BPTI(1Ala 11Pro 15Arg 17Leu 18His 19Thr 34Phe 39Tyr 46Glu)
BPTI(1Ala 11Val 13His 15Arg 17Leu 18His 19Leu 34Leu 39His 46Glu)
BPTI(1Ala 13Ile 15Arg 17Leu 18His 19Gln 39Leu 46Glu)
BPTI(1Ala 13Ile 15Arg 17Leu 18His 39Leu 46Glu)
BPTI(1Ala 13Ile 15Arg 17Leu 18His 19Thr 39Leu 46Glu)
BPTI(1Ala 13Ile 15Arg 17Leu 18His 19Lys 39Leu 46Glu)
BPTI(1Ala 13Ile 15Arg 17Ile 18His 19Leu 39Leu 46Glu)
BPTI(1Ala 13Ile 15Arg 17Ile 18His 19Val 39Leu 46Glu)
BPTI(1Ala 13Ile 15Arg 17Met 18His 19Leu 39Leu 46Glu)
BPTI(1Ala 13Ile 15Arg 17Tyr 18Tyr 19Lys 39Leu 46Glu)
BPTI(1Ala 11Pro 13Phe 15Arg 17Leu 18His 19Lys 34His 39Phe 46Glu)
BPTI(11Asp 15Arg 17Leu 18His 19Pro 34Trp 39Tyr 46Glu)
BPTI(11Asp 15Arg 17Leu 18His 19Pro 34Trp 39Leu 46Glu)
BPTI(11Asp 15Arg 17Leu 18His 19His 34Tyr 46Glu)
BPTI(11Glu 13Trp 15Arg 17Leu 18His 19His 34Ile 39Gly 46Glu)
BPTI(15Arg 17Leu 18His 19His 34Phe 39Phe 46Glu)
BPTI(11Ser 13Leu 15Arg 17Leu 18His 19Lys 34Tyr 39Tyr 46Glu)
BPTI(11Pro 13Ile 15Arg 17Leu 18His 19Lys 34His 39Phe 46Glu)
BPTI(11Ser 13Leu 15Arg 17Leu 18His 19Lys 34Tyr 39Phe 46Glu)
BPTI(11Pro 13Ile 15Arg 17Leu 18His 19Lys 34Tyr 39Met 46Glu)

BPTI(11Glu 13Met 15Arg 17Ile 18His 19Lys 34Thr 39Met 46Glu)
BPTI(11Pro 13Val 15Arg 17Leu 18His 19Lys 34Ser 39Gln 46Glu)
BPTI(11Glu 13Leu 15Arg 17Leu 18His 19Lys 34Tyr 39Phe 46Glu)
BPTI(11Pro 13Leu 15Arg 17Leu 18His 19Lys 34Tyr 39Tyr 46Glu)
BPTI(11Asp 15Arg 17Leu 18His 19Gln 39Phe 46Glu)
BPTI(9Ala 11Asp 15Arg 17Leu 18His 19Gln 22Leu 39Phe 46Glu)
BPTI(13Ile 15Arg 17Ala 18Phe 19Asn 39Leu 46Glu)
BPTI(13Ile 15Arg 17Phe 18Tyr 19Lys 39Leu 46Glu)
BPTI(13Ile 15Arg 17Tyr 18Tyr 19Lys 39Leu 46Glu).

2. A compound derived from bovine pancreatic trypsin inhibitor which inhibits the biological activity of factor VIIa-tissue factor complex with an inhibition constant less than 50 nM selected from the group consisting of:

BPTI(1Ala 11Asp 15Arg 17Ile 19Lys 39Glu 46Glu)
BPTI(1Ala 11Asp 17Ile 19Lys 39Phe 46Glu)
BPTI(1Ala 11Asp 17Ile 19Lys 39Tyr 46Glu
BPTI(1Ala 11Asp 15Arg 17Ile 19Lys 39Phe 46Glu)
BPTI(1Ala 11Asp 15Arg 17Ile 19Lys 39Tyr 46Glu)
BPTI(1Ala 15Arg 17Ile 19Lys 39Phe 46Glu)
BPTI(1Ala 11Glu 15Arg 17Tyr 19Thr 39Tyr 46Glu)
BPTI(1Ala 15Arg 17Met 18His 19His 39Phe 46Glu)
BPTI(1Ala 11Asp 15Arg 17Leu 18His 19Leu 34Tyr 39Leu 46Glu)
BPTI(1Ala 11Glu 13Tyr 15Arg 17Leu 18His 34Tyr 39His 46Glu
BPTI(1Ala 11Glu 13Ala 15Arg 17Leu 18His 19Leu 34Tyr 39Tyr 46Glu)
BPTI(1Ala 11Glu 13Phe 15Arg 17Leu 18His 19Pro 34Tyr 39His 46Glu)
BPTI(1Ala 11Glu 13Phe 15Arg 17Leu 18His 19Thr 34Tyr 39His 46Glu)
BPTI(1Ala 11Asp 15Arg 17Leu 18His 19Thr 34Thr 39Phe 46Glu)
BPTI(1Ala 11Pro 13Tyr 15Arg 17Leu 18His 19Leu 34Thr 39His 46Glu)
BPTI(1Ala 11Asp 15Arg 17Leu 18His 19Gln 34Thr 46Glu)
BPTI(1Ala 11Glu 15Arg 17Ile 18His 19Pro 34Leu 39Tyr 46Glu)
BPTI(13Ile 15Arg 17Leu 18His 39Leu 46Glu)
BPTI(11Asp 15Arg 17Leu 18His 19Thr 34Thr 39Phe 46Glu)
BPTI(11Gly 13Val 15Arg 17Ile 18His 19Leu 34Ile 39Tyr 46Glu)
BPTI(11Glu 15Arg 17Ile 18His 19Pro 34Leu 39Tyr 46Glu)
BPTI(11Asp 15Arg 17Leu 18His 19Gln 34Thr 46Glu)
BPTI(11Glu 13Phe 15Arg 17Leu 18His 19Thr 34Tyr 39His 46Glu)
BPTI(11Glu 13Ala 15Arg 17Leu 18His 19Leu 34Tyr 39Tyr 46Glu)
BPTI(11Asp 15Arg 17Leu 18His 19Leu 34Tyr 39Leu 46Glu)
BPTI(11Glu 13Tyr 15Arg 17Leu 18His 34Tyr 39His 46Glu)
BPTI(11Pro 13Tyr 15Arg 17Leu 18His 19Leu 34Thr 39His 46Glu)
BPTI(11Asp 15Arg 17Leu 18His 19Pro 34Trp 39Tyr 46Glu)
BPTI(11Asp 15Arg 17Leu 18His 19Pro 34Trp 39Leu 46Glu)
BPTI(11Asp 15Arg 17Leu 18His 19His 34Tyr 46Glu)
BPTI(11Glu 13Trp 15Arg 17Leu 18His 19His 34Ile 39Gly 46Glu)
BPTI(15Arg 17Leu 18His 19His 34Phe 39Phe 46Glu)
BPTI(11Ser 13Leu 15Arg 17Leu 18His 19Lys 34Tyr 39Tyr 46Glu)
BPTI(11Pro 13Ile 15Arg 17Leu 18His 19Lys 34His 39Phe 46Glu)
BPTI(11Ser 13Leu 15Arg 17Leu 18His 19Lys 34Tyr 39Phe 46Glu)
BPTI(11Pro 13Ile 15Arg 17Leu 18His 19Lys 34Tyr 39Met 46Glu)
BPTI(11Glu 13Met 15Arg 17Ile 18His 19Lys 34Thr 39Met 46Glu)
BPTI(11Pro 13Val 15Arg 17Leu 18His 19Lys 34Ser 39Gln 46Glu)
BPTI(11Glu 13Leu 15Arg 17Leu 18His 19Lys 34Tyr 39Phe 46Glu)
BPTI(11Pro 13Leu 15Arg 17Leu 18His 19Lys 34Tyr 39Tyr 46Glu)
BPTI(11Asp 15Arg 17Leu 18His 19Gln 39Phe 46Glu)
BPTI(9Ala 11Asp 15Arg 17Leu 18His 19Gln 22Leu 39Phe 46Glu).

3. A compound derived from bovine pancreatic trypsin inhibitor which inhibits the biological activity of factor VIIa-tissue factor complex with an inhibition constant less than 5 nM selected from the group consisting of:

BPTI(11Asp 15Arg 17Leu 18His 19Gln 34Thr 46Glu)
BPTI(11Asp 15Arg 17Leu 18His 19Leu 34Tyr 39Leu 46Glu)
BPTI(11Glu 13Tyr 15Arg 17Leu 18His 34Tyr 39His 46Glu)
BPTI(11Asp 15Arg 17Leu 18His 19Pro 34Trp 39Tyr 46Glu)
BPTI(11Asp 15Arg 17Leu 18His 19Pro 34Trp 39Leu 46Glu)
BPTI(11Asp 15Arg 17Leu 18His 19His 34Tyr 46Glu)
BPTI(11Ser 13Leu 15Arg 17Leu 18His 19Lys 34Tyr 39Phe 46Glu)
BPTI(11Glu 13Leu 15Arg 17Leu 18His 19Lys 34Tyr 39Phe 46Glu)
BPTI(9Ala 11Asp 15Arg 17Leu 18His 19Gln 22Leu 39Phe 46Glu)

4. A pharmaceutical composition comprising a pharmaceutically acceptable carrier and pharmaceutically effective amount of compound of claim 1, 2, or 3.

* * * * *